US011396522B2

(12) United States Patent
Vocadlo et al.

(10) Patent No.: US 11,396,522 B2
(45) Date of Patent: Jul. 26, 2022

(54) BIS-ACETAL-BASED SUBSTRATES FOR IMAGING EXO-GLYCOSIDASE ACTIVITY

(71) Applicant: ALECTOS THERAPEUTICS INC., Burnaby (CA)

(72) Inventors: David J. Vocadlo, Burnaby (CA); Samy Cecioni, Burnaby (CA); Roger Ashmus, Burnaby (CA)

(73) Assignee: ALECTOS THERAPEUTICS INC., Burnaby (CA)

( * ) Notice: Subject to any disclaimer, the term of this patent is extended or adjusted under 35 U.S.C. 154(b) by 371 days.

(21) Appl. No.: 16/622,870

(22) PCT Filed: Jun. 12, 2018

(86) PCT No.: PCT/IB2018/054273
§ 371 (c)(1),
(2) Date: Dec. 13, 2019

(87) PCT Pub. No.: WO2018/229663
PCT Pub. Date: Dec. 20, 2018

(65) Prior Publication Data
US 2020/0207800 A1    Jul. 2, 2020

Related U.S. Application Data

(60) Provisional application No. 62/519,487, filed on Jun. 14, 2017.

(51) Int. Cl.
*G01N 33/58* (2006.01)
*G01N 33/542* (2006.01)
*G01N 21/64* (2006.01)
*C07H 15/26* (2006.01)

(52) U.S. Cl.
CPC .......... *C07H 15/26* (2013.01); *G01N 21/6428* (2013.01); *G01N 33/542* (2013.01); *G01N 33/582* (2013.01); *G01N 2021/6432* (2013.01); *G01N 2333/924* (2013.01)

(58) Field of Classification Search
CPC ...... C12Q 1/34; G01N 33/542; G01N 33/582; G01N 21/6428; G01N 2021/6432; G01N 2333/924; C07H 15/26
See application file for complete search history.

(56) References Cited

FOREIGN PATENT DOCUMENTS

WO    2018/229663    12/2018

OTHER PUBLICATIONS

Komatsu et al. Design and synthesis of an enzyme activity-based labeling molecule with fluorescence spectral change. J. Am. Chem. Soc. 2006, vol. 128, p. 15946-15947. (Year: 2006).*

Yadav et al. Fluorescence-quenched substrates for live cell imaging of human glucocerebrosidase activity. J. Am. Chem. Soc. 2015, vol. 137, pp. 1181-1189. (Year: 2015).*
Boyd, Robert E. et al., "Pharmacological Chaperones as Therapeutics for Lysosomal Storage Diseases," Journal of Medicinal Chemistry 2013, 56, 2705-2725.
Brady, R.O. et al., "Demonstration of a deficiency of glucocerebroside-cleaving enzyme in Gaucher's disease," The Journal of Clinical Investigation 1966, 45(7): 1112-1115.
Burke, Helen M., et al., "Recent advances in the development of synthetic chemical probes for glycosidase anzymes," Chemical Communications 2015, 51, 10576-10588.
Cecioni et al, "Carbohydrate Bis-acetal-Based Substrates as Tunable Fluorescence-Quenched Probes for Monitoring exo-Glycosidase Activity", J. Am. Chem. Soc. Jun. 20, 2017 139:8392-9395.
Cox, Timothy, et al., "Novel oral treatment of Gaucher's disease with N-butyldeoxynojirimycin (OGT 918) to decrease substrate biosynthesis," Lancet 2000, 355, 1481-5.
Edington, Laura et al., "Functional imaging of proteases: recent advances in the design and application of substrate-based and activity-based probes," Curr Opin Chem Biol 2011, 15, 798-805.
Evans, Michael J., et al., "Mechanism-Based Profiling of Enzyme Families," Chemical Reviews 2006, 106, 3279-3301.
Fan, Jian-Qiang et al., "Accelerated transport and maturation of lysosomal," Nat Med 1999, 5, 112-5.
Fan, Jian-Qiang, "A contradictory treatment for lysosomal storage disorders: inhibitors enhance mutant enzyme activity," Trends in Pharmacological Sciences 2003, 24, 355-360.
Folk, Drew S. Folk, et al., "Monitoring B-Secretase Activity in Living Cells with a Membrane-Anchored FRET Probe," Angew Chem Int Ed Engl 2012, 51, 10795-9.
Garland, Megan et al., "A Bright Future for Precision Medicine: Advances in Fluorescent Chemical Proble Design and Their Clinical Application," Cell Chemical Biology 2016, 23, 122-136.
Gillies, Elizabeth R., et al., "Acetals as pH-Sensitive Linkages for Drug Delivery," Bioconjugate Chemistry 2004, 15, 1254-1263.
Gloster, Tracey M. et al., "Developing inhibitors of glycan processing enzymes as tools for enabling glycobiology," Nature Chemical Biology 2012, 8, 683-694.
Greig, Ian R., et al., "Probinig Synergy between Two Catalytic Strategies in the Glycoside Hydrolase O-GlcNAcase Using Multiple Linear Free Energy Relationships," Journal of the American Chemical Society 2009, 131, 13415-13422.
Han, Junyan et al., "A fluorogenic probe for B-galactosidase activity imaging in living cells," Molecular BioSystems 2013, 9, 3001-3008.
Harlan, Fiona Karen, et al., "Fluorogenic Substrates for Visualizing Acidic Organelle Enzyme Activities," PLoS One 2016, 11, e0156312.
He, Lizhi et al., "a-Mannosidase 2C1 attenuates PTEN function in prostate cancer cells," Nat. Commun. 2011, 2, 307.
Ho, Nan-Hui Ho et al., "A Self-Immolative Reporter For B-Galactosidase Sensing," ChemBioChem 2007, 8, 560-566.
Hu, Hai-Yu, et al., "In Vivo Imaging of Mouse Tumors by a Lipidated Cathepsin S Substrate," Angew. Chem., International Edition in English 2014, 53, 7669-7673.

(Continued)

*Primary Examiner* — Shafiqul Haq
(74) *Attorney, Agent, or Firm* — Lewis Roca Rothgerber Christie LLP

(57) ABSTRACT

The invention provides fluorescence-quenched substrates of exo-glycosidase enzymes. The invention also provides methods for imaging exo-glycosidase enzymes activity within cells.

19 Claims, 12 Drawing Sheets

(56) References Cited

OTHER PUBLICATIONS

Kamiya Mako, et al., "B-Galactosidase Fluorescence Probe with Improved Cellular Accumulation Based on a Spirocyclized Rhodol Scaffold," Journal of the American Chemical Society 2011, 133, 12960-12963.
Komatsu, Toru et al., "Design and Synthesis of an Enzyme Activity-Based Labeling Molecule with Fluorescence Spectral Change," Journal of the American Chemical Society 2006, 128, 15946-15947.
Kornhaber, Gregory J. et al., "Isofagomine Induced Stabilization of Glucocerebrosidase," Chembiochem 2008, 9, 2643-9.
Lombard, Vincent et al., "The carbohydrate-active enzymes database (CAZy) in 2013," Nucleic Acids Research 2014, 42, D490-D495.
Liu, Bin et al. "Substituent Effects on the pH Sensitivity of Acetals and Ketals and Their Correlation with Encapsulation Stability in Polymeric Nanogels," Journal of the American Chemical Society 2017, 139, 2306-2317.
McCarter, John D. et al, "Binding energy and catalysis," Biochemical Journal 1992, 286, 721-727.
McNeill, Alisdair et al., "Ambroxol improves lysosomal biochemistry in glucocerebrosidase mutation-linked Parkinson disease cells," Brain 2014, 137, 1481-95.
Namchuk, Mark N. et al, "Mechanism of Agrobacterium B-Glucosidase: Kinetic Analysis of the Role of Noncovalent Enzyme/Substrate Interactions," Biochemistry 1995, 34, 16194-16202.
Parenti, Giancarlo et al., "Treating lysosomal storage diseases with pharmacological chaperones: from concept to clinics," Embo Molecular Medicine 2009, 1, 268-279.
Patnaik, Samarjit et al., "Discovery, Structure-Activity Relationship, and Biological Evaluation of Noninhibitory Small Molecule Chaperones of Glucocerebrosidase," Journal of Medicinal Chemistry 2012, 55, 5734-5748.
Richter, Franziska et al., "A GCase Chaperone Improves Motor Function in a Mouse Model of Synucleinopathy," Neurotherapeutics 2014, 11, 843-856.
Sakabe, Masayo, et al., "Rational Design of High Sensitive Fluorescence Probes for Protease and Glycosidase Based on Precisely Controlled Spirocyclization," Journal of the American Chemical Society 2013, 135, 409-414.
Sawkar, Anu R., et al., "Chemical chaperones increase the cellular activity of N370S B-glucosidase: A therapeutic strategy for Gaucher disease," Proc Natl Acad Sci U S A 2002, 99, 15428-33.
Sidransky, Ellen et al, "The link between the GBA gene and parkinsonism," The Lancet Neurology 2012, 11, 986-998.
Shen, David L., et al., "Insights into O-Linked N-Acetylglucosamine (O-GlcNAc) Processing and Dynamics through Kinetic Analysis of O-GlcNAc Transferase and O-GlcNAcase Activity on Protein Substrates," Journal of Biological Chemistry 2012, 287, 15395-15408.
Tropak, Michael B., et al., "Identification of Pharmacological Chaperones for Gaucher Disease and Characterization of Their Effects on B-Glucocerebrosidase by Hydrogen/Deuterium Exchange Mass Spectrometry," Chembiochem 2008, 9, 2650-62.
Trapero, Ana, et al., "Glucocerebrosidase inhibitors: future drugs for the treatment of Gaucher disease?" Future Medicinal Chemistry 2014, 6, 975-978.
Vocadlo, David J., "O-GlcNAc processing enzymes: catalytic mechanisms, substrate specificity, and enzyme regulation," Current Opinion in Chemical Biology 2012, 16, 488-497.
Watzke, Anja et al., "Selective Activity-Based Probes for Cysteine Cathepsins," Angew Chem Int Ed Engl 2008, 47, 406-9.
Whitney, Michael et al., "Ratiometric Activatable Cell-Penetrating Peptides Provide Rapid In Vivo Readout of Thrombin Activation," Angew. Chem., International Edition in English 2013, 52, 325-330.
Witte, Martin D. et al., "Ultrasensitive in situ visulation of active glucocerebrosidase molecules," Nat Chem Biol 2010, 6, 907-13.
Yadav, Anuj K. et al, "Fluorescence-Quenched Substrates for Live Cell Imaging of Human Glucocerebrosidase Activity", J. Am Chem. Soc. 2015, 137:1181-1189.
Yuzwa, Scott A. et al., "O-GlcNAc and neurodegeneration: biochemical mechanisms and potential roles in Alzheimer's disease and beyond," Chemical Society Reviews 2014, 43, 6839-6858.
International Search Report and Written Opinion issued in corresponding International Application No. PCT/IB2018/054273 dated Sep. 12, 2018.
Cortez-Retamozo, Virna et al., "Real-time assessment of inflammation and treatment response in a mouse model of allergic airway inflammation," The Journal of Clinical Investigation, 2008; 118(12):4058-4066.

* cited by examiner

BIS-ACETAL-BASED SUBSTRATES FOR IMAGING EXO-GLYCOSIDASE ACTIVITY

CROSS-REFERENCE TO RELATED APPLICATION(S)

This application is a National Phase Patent Application and claims priority to and the benefit of International Application Number PCT/IB2018/054273, filed on Jun. 12, 2018, which claims priority to and the benefit of U.S. Provisional Patent Application No. 62/519,487, filed on Jun. 14, 2017, the entire contents of all of which are incorporated herein by reference.

FIELD OF THE INVENTION

The application relates to fluorescence-quenched substrates of exo-glycosidase enzymes and uses thereof.

BACKGROUND OF THE INVENTION

Among the glycoside hydrolases encoded by the human genome,[1] most are exo-glycosidases which remove the terminal glycoside residues from oligosaccharides, proteins and glycolipids. Exo-glycosidases are receiving increasing interest owing to their emerging roles in human health. Deficiencies in the activities of several exo-glycosidases found in lysosomes have been implicated in lysosomal storage diseases.[2] Exo-glycosidases have also emerged as therapeutic targets for diseases such as Parkinson's disease (PD)[3], Alzheimer's disease (AD)[4] as well as cancers.[5]

The decreased activities of lysosomal exo-glycosidases in humans can result in detrimental accumulation of their natural substrates within the lysosomes of affected tissues. The set of lysosomal storage disorders that arises from the deficiencies of lysosomal exo-glycosidase activities notably include Gaucher (acid β-glucosidase, exo-glycosidase, EC 3.2.1.45), Fabry (acid α-galactosidase, GALA, EC 3.2.1.22), Tay-Sachs (hexosaminidase A, HexA, EC 3.2.1.52), and Krabbe diseases (galactosylceramidase, GALC, EC 3.2.1.46). These diseases arise from mutations of the exo-glycosidase genes that result in decreased activity, trafficking and/or stability of the resulting enzymes.

Treatments for exo-glycosidase-related lysosomal storage disorders include enzyme replacement therapy (ERT),[6] which is based on chronic intravenous administration of recombinant wild-type enzymes. Another is substrate reduction therapy (SRT),[7] which is based on chronic oral administration of inhibitors for the upstream enzymes that synthesize exo-glycosidase substrates. Over the past decade, an alternative experimental approach called pharmacological chaperone therapy has gained attention.[8,9,10] The latter is based on the use of chemical chaperones that can stabilize the mutant exo-glycosidase and improve their trafficking to the lysosomes. Generally, the efficiency of inhibitory chaperones for lysosomal exo-glycosidase is established by monitoring increases in the levels of these enzymes by immunoblotting of cell lysates.[9,11-13] There are however few existing methods to visualize and quantify the effects of pharmacological chaperones directly in living cells.

Other non-lysosomal exo-glycosidases such as O-GlcNAcase (OGA, EC 3.2.1.169) are gaining interest as therapeutic targets for neurodenerative diseases including Alzheimer's disease and other tauopathies. OGA cleaves O-linked β-N-acetylglucosamine (O-GlcNAc) units from serine and threonine residues of nuclear and cytoplasmic proteins.[14]

Various enzyme classes including most notably proteases, have had fluorescence-quenched substrates deployed for a range of applications. These are powerful tools to study their function in live cells.[15-22] However, the design of fluorescence-quenched substrates for exo-glycoside hydrolase probes is more problematic than for proteases and is lagging behind. Successful targeting of proteases likely stems from their cleft-like active site architecture, which accommodate positioning the requisite pair of fluorochromes at the N- and C-terminus of peptide-based substrates. More problematic has been the creation of such substrate probes for exo-acting glycoside hydrolases which have pocket-shaped active sites that are sterically demanding.[18] Existing substrate probes for exo-glycosidases (fluorogenic phenolate-based glycosides[23,24], reactive quinone methide-based probes[25-27] or spirocyclic rhodol and rhodamine-based glycosides[28,29]) show limitations for studying the regulation of enzyme activity in a cellular context. For example, the pH-dependent fluorescence of spirocyclic fluorochromes and phenolate-based substrates may be problematic when targeting various cellular compartments that show a range of pH values. Also, the potential irreversible inactivation of enzymes by reactive electrophiles may also present challenges for quantitating enzyme activity. Other approaches include the functionalization of the primary hydroxyl of the carbohydrate residue in order to generate fluorescence-quenched probes.[30,31] While effective for the limited number of exo-glycosidases that tolerate such a bulky functionalization, this approach has not proven generally applicable since hydroxyl groups are often critical recognition elements for various glycoside hydrolases.[32,33] Despite the critical importance of monitoring the activity of exo-glycosidases in live cells or in tissues, no generally applicable strategy has prevailed for the development of substrate probes for exo-glycosidases.

SUMMARY OF THE INVENTION

The present disclosure provides, in part, fluorescence-quenched substrate compounds for exo-glycosidases, uses of the compounds, methods for monitoring exo-glycosidase activity within cells or tissue, methods for localization of exo-glycosidase activity within cytosol or cellular compartments, methods for monitoring the effects of an exo-glycosidase inhibitor in cells or tissue, methods for monitoring the effects of an exo-glycosidase chaperone in cells or tissue, methods for monitoring the effects of an exo-glycosidase activator in cells or tissue, methods for monitoring an exo-glycosidase activity within cells or tissue as a biomarker for an exo-glycosidase-directed therapy, or methods for conducting a cell-based library screen to identify an exo-glycosidase activity enhancer or an exo-glycosidase inhibitor.

In one aspect, the invention provides a compound of Formula (I), or an acceptable salt thereof:

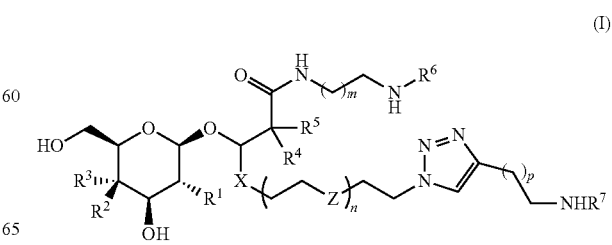

(I)

where X may be O or S; Z may be O or CH$_2$; R$^1$ may be OH or NHC(O)CH$_3$; R$^2$ may be OH and R$^3$ may be H, or R$^2$ may be H and R$^3$ may be OH; R$^4$ may be H or CH$_3$; R$^5$ may be H, OH, or halo; R$^6$ may be a suitable fluorophore and R$^7$ may be a suitable quencher, or R$^6$ may be a suitable quencher and R$^7$ may be a suitable fluorophore; m may be an integer from 1 to 5; n may be an integer from 0 to 2; and p may be an integer from 0 to 5.

In alternative embodiments, X may be O or S; Z may be O or CH$_2$; R$^1$ may be OH or NHC(O)CH$_3$; R$^2$ may be OH and R$^3$ may be H, or R$^2$ may be H and R$^3$ may be OH; R$^4$ may be H or CH$_3$; R$^5$ may be H, OH, or halo; R$^6$ may be a suitable fluorophore; R$^7$ may be (E)-4-((4-(dimethylamino)phenyl)diazenyl)benzoyl or 4-((4-((E)-(2,5-dimethoxy-4-((E)-(4-nitrophenyl)diazenyl)phenyl)diazenyl)phenyl)(methyl)amino)-butanoyl; m may be an integer from 1 to 5; n may be an integer from 0 to 2; and p may be an integer from 0 to 5.

In alternative embodiments, X may be O or S; Z may be O or CH$_2$; R$^1$ may be OH or NHC(O)CH$_3$; R$^2$ may be OH and R$^3$ may be H, or R$^2$ may be H and R$^3$ may be OH; R$^4$ may be H or CH$_3$; R$^5$ may be H, OH, or halo; R$^6$ may be 5-sulfonaphthalen-1-yl or (2-(6-(dimethylamino)-3-(dimethyliminio)-3H-xanthen-9-yl)benzoate)-5-carbonyl; R$^7$ may be a suitable quencher; m may be an integer from 1 to 5; n may be an integer from 0 to 2; and p may be an integer from 0 to 5.

In alternative embodiments, X may be O or S; Z may be O or CH$_2$; R$^1$ may be OH or NHC(O)CH$_3$; R$^2$ may be OH and R$^3$ may be H, or R$^2$ may be H and R$^3$ may be OH; R$^4$ may be H or CH$_3$; R$^5$ may be H, OH, or halo; R$^6$ may be 5-sulfonaphthalen-1-yl or (2-(6-(dimethylamino)-3-(dimethyliminio)-3H-xanthen-9-yl)benzoate)-5-carbonyl; R$^7$ may be (E)-4-((4-(dimethylamino)phenyl)diazenyl)benzoyl or 4-((4-((E)-(2,5-dimethoxy-4-((E)-(4-nitrophenyl)diazenyl)phenyl)diazenyl)phenyl)(methyl)amino)-butanoyl; m may be an integer from 1 to 5; n may be an integer from 0 to 2; and p may be an integer from 0 to 5.

In alternative embodiments, the invention provides a compound of Formula (Ia), or an acceptable salt thereof:

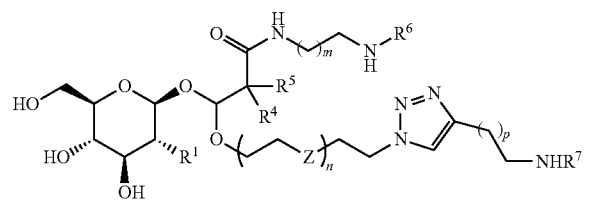

(Ia)

where Z may be O or CH$_2$; R$^1$ may be OH or NHC(O)CH$_3$; R$^4$ may be H or CH$_3$; R$^5$ may be H, OH, or halo; R$^6$ may be a suitable fluorophore and R$^7$ may be a suitable quencher, or R$^6$ may be a suitable quencher and R$^7$ may be a suitable fluorophore; m may be an integer from 1 to 5; n may be an integer from 0 to 2; and p may be an integer from 0 to 5.

In alternative embodiments, the invention provides a compound of Formula (Ib), or an acceptable salt thereof:

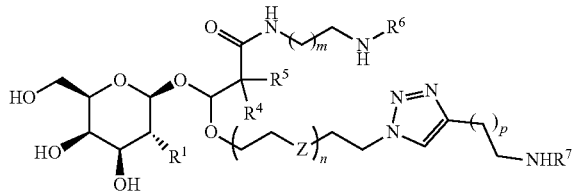

(Ib)

where Z may be O or CH$_2$; R$^1$ may be OH or NHC(O)CH$_3$; R$^4$ may be H or CH$_3$; R$^5$ may be H, OH, or halo; R$^6$ may be a suitable fluorophore and R$^7$ may be a suitable quencher, or R$^6$ may be a suitable quencher and R$^7$ may be a suitable fluorophore; m may be an integer from 1 to 5; n may be an integer from 0 to 2; and p may be an integer from 0 to 5.

In alternative embodiments, the invention provides a compound of Formula (Ic), or an acceptable salt thereof:

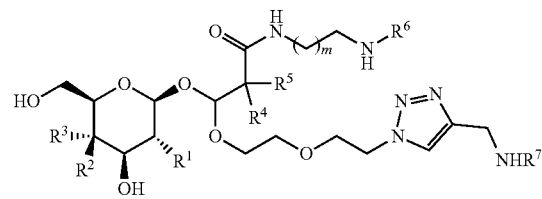

(Ic)

where R$^1$ may be OH or NHC(O)CH$_3$; R$^2$ may be OH and R$^3$ may be H, or R$^2$ may be H and R$^3$ may be OH; R$^4$ may be H or CH$_3$; R$^5$ may be H, OH, or halo; R$^6$ may be a suitable fluorophore and R$^7$ may be a suitable quencher, or R$^6$ may be a suitable quencher and R$^7$ may be a suitable fluorophore; and m may be an integer from 1 to 5.

In alternative embodiments, the invention provides a compound of Formula (Id), or an acceptable salt thereof:

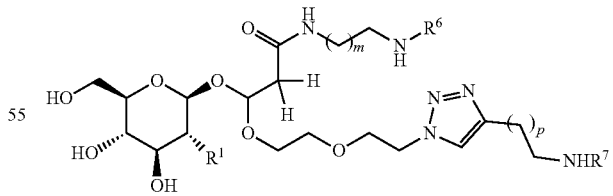

(Id)

where R$^1$ may be OH or NHC(O)CH$_3$; R$^6$ may be a suitable fluorophore and R$^7$ may be a suitable quencher, or R$^6$ may be a suitable quencher and R$^7$ may be a suitable fluorophore; m may be an integer from 1 to 5; and p may be an integer from 0 to 5.

In alternative embodiments, the invention provides a compound of Formula (Ie), or an acceptable salt thereof:

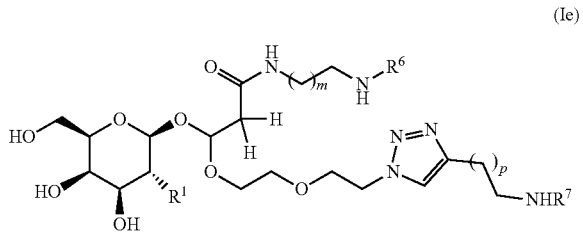 (Ie)

where R¹ may be OH or NHC(O)CH₃; R⁶ may be a suitable fluorophore and R⁷ may be a suitable quencher, or R⁶ may be a suitable quencher and R⁷ may be a suitable fluorophore; m may be an integer from 1 to 5; and p may be an integer from 0 to 5.

In alternative embodiments, the invention provides a compound of Formula (If), or an acceptable salt thereof:

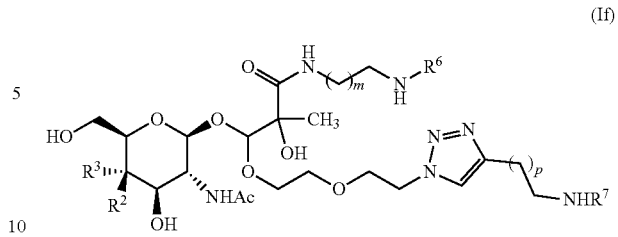 (If)

where R² may be OH and R³ may be H, or R² may be H and R³ may be OH; R⁶ may be a suitable fluorophore and R⁷ may be a suitable quencher, or R⁶ may be a suitable quencher and R⁷ may be a suitable fluorophore; m may be an integer from 1 to 5; and p may be an integer from 0 to 5.

In alternative embodiments, the invention provides a compound of Formula (Ig), or an acceptable salt thereof:

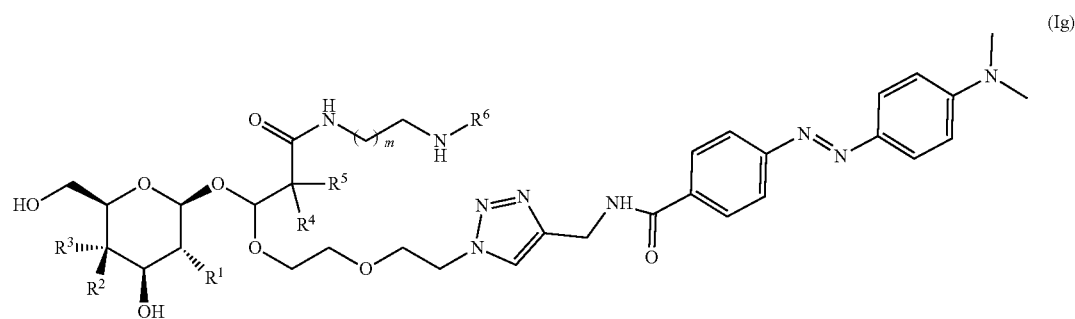 (Ig)

where R¹ may be OH or NHC(O)CH₃; R² may be OH and R³ may be H, or R² may be H and R³ may be OH; R⁴ may be H or CH₃; R⁵ may be H, OH, or halo; R⁶ may be a suitable fluorophore; m may be an integer from 1 to 5.

In alternative embodiments, the invention provides a compound of Formula (Ih), or an acceptable salt thereof:

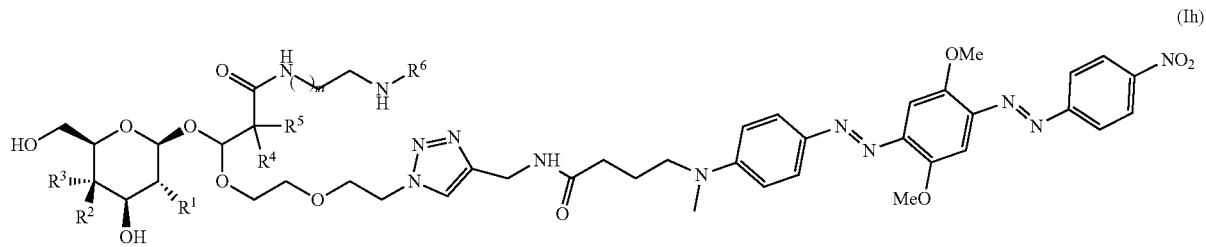 (Ih)

where R¹ may be OH or NHC(O)CH₃; R² may be OH and R³ may be H, or R² may be H and R³ may be OH; R⁴ may be H or CH₃; R⁵ may be H, OH, or halo; R⁶ may be a suitable fluorophore; m may be an integer from 1 to 5.

In alternative embodiments, the invention provides a compound of Formula (Ii), or an acceptable salt thereof:

(Ii)

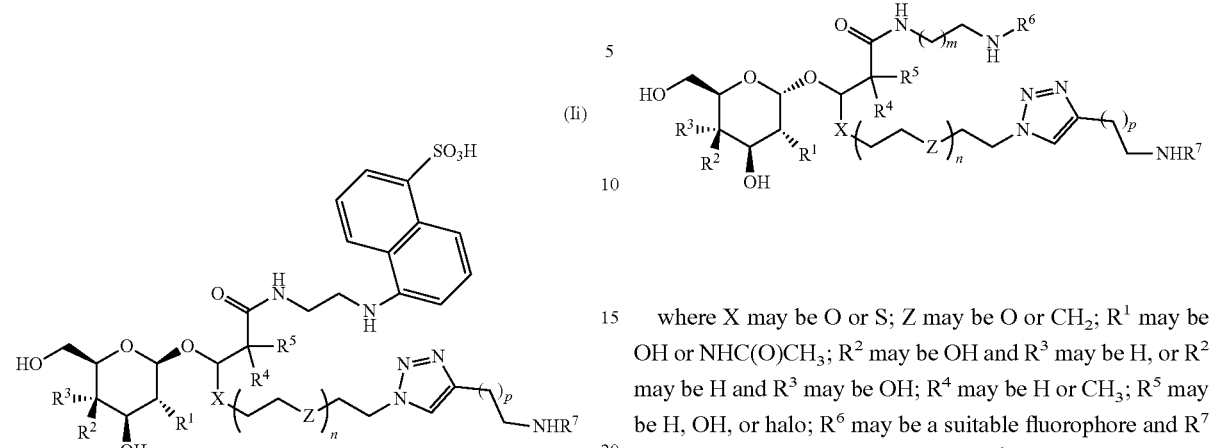

where X may be O or S; Z may be O or CH$_2$; R$^1$ may be OH or NHC(O)CH$_3$; R$^2$ may be OH and R$^3$ may be H, or R$^2$ may be H and R$^3$ may be OH; R$^4$ may be H or CH$_3$; R$^5$ may be H, OH, or halo; R$^7$ may be a suitable quencher; n may be an integer from 0 to 2; and p may be an integer from 0 to 5.

In alternative embodiments, the invention provides a compound of Formula (Ij), or an acceptable salt thereof:

(Ij)

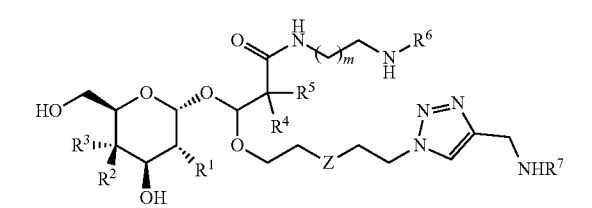

where X may be O or S; Z may be O or CH$_2$; R$^1$ may be OH or NHC(O)CH$_3$; R$^2$ may be OH and R$^3$ may be H, or R$^2$ may be H and R$^3$ may be OH; R$^4$ may be H or CH$_3$; R$^5$ may be H, OH, or halo; R$^7$ may be a suitable quencher; n may be an integer from 0 to 2; and p may be an integer from 0 to 5.

In alternative embodiments, the invention provides a compound of Formula (II), or an acceptable salt thereof:

(II)

where X may be O or S; Z may be O or CH$_2$; R$^1$ may be OH or NHC(O)CH$_3$; R$^2$ may be OH and R$^3$ may be H, or R$^2$ may be H and R$^3$ may be OH; R$^4$ may be H or CH$_3$; R$^5$ may be H, OH, or halo; R$^6$ may be a suitable fluorophore and R$^7$ may be a suitable quencher, or R$^6$ may be a suitable quencher and R$^7$ may be a suitable fluorophore; m may be an integer from 1 to 5; n may be an integer from 0 to 2; and p may be an integer from 0 to 5.

In alternative embodiments, the invention provides a compound of Formula (IIa), or an acceptable salt thereof:

(IIa)

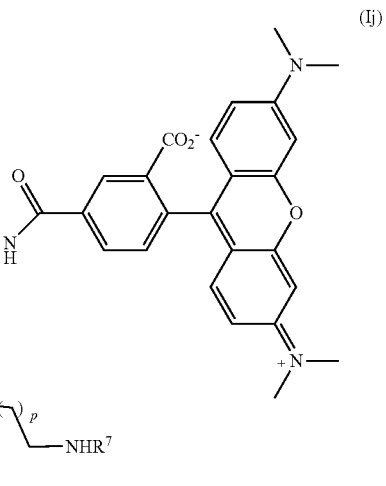

where Z may be O or $CH_2$; $R^1$ may be OH or $NHC(O)CH_3$; $R^2$ may be OH and $R^3$ may be H, or $R^2$ may be H and $R^3$ may be OH; $R^4$ may be H or $CH_3$; $R^5$ may be H, OH, or halo; $R^6$ may be a suitable fluorophore and $R^7$ may be a suitable quencher, or $R^6$ may be a suitable quencher and $R^7$ may be a suitable fluorophore; m may be an integer from 1 to 5.

In alternative embodiments, the invention provides a compound of Formula (III), or an acceptable salt thereof:

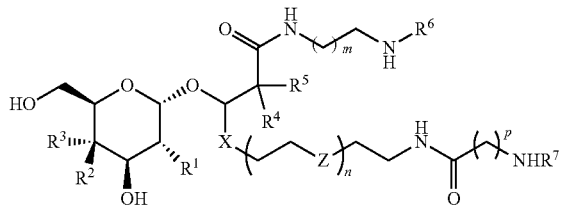

(III)

where X may be O or S; Z may be O or $CH_2$; $R^1$ may be OH or $NHC(O)CH_3$; $R^2$ may be OH and $R^3$ may be H, or $R^2$ may be H and $R^3$ may be OH; $R^4$ may be H or $CH_3$; $R^5$ may be H, OH, or halo; $R^6$ may be a suitable fluorophore and $R^7$ may be a suitable quencher, or $R^6$ may be a suitable quencher and $R^7$ may be a suitable fluorophore; m may be an integer from 1 to 5; n may be an integer from 0 to 2; and p may be an integer from 0 to 5.

In alternative embodiments, the invention provides a compound of Formula (IIIa), or an acceptable salt thereof:

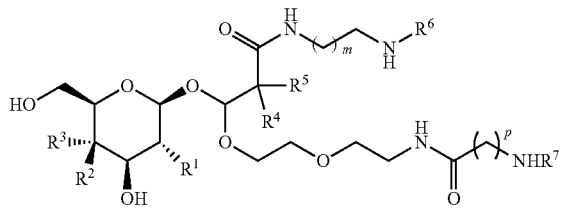

(IIIa)

where $R^1$ may be OH or $NHC(O)CH_3$; $R^2$ may be OH and $R^3$ may be H, or $R^2$ may be H and $R^3$ may be OH; $R^4$ may be H or $CH_3$; $R^5$ may be H, OH, or halo; $R^6$ may be a suitable fluorophore and $R^7$ may be a suitable quencher, or $R^6$ may be a suitable quencher and $R^7$ may be a suitable fluorophore; m may be an integer from 1 to 5; and p may be an integer from 0 to 5.

In alternative embodiments, the invention provides a compound of Formula (IIIb), or an acceptable salt thereof:

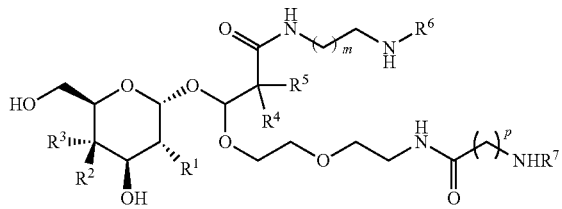

(IIIb)

where $R^1$ may be OH or $NHC(O)CH_3$; $R^2$ may be OH and $R^3$ may be H, or $R^2$ may be H and $R^3$ may be OH; $R^4$ may be H or $CH_3$; $R^5$ may be H or $CH_3$; $R^5$ may be H, OH, or halo; $R^6$ may be a suitable fluorophore and $R^7$ may be a suitable quencher, or $R^6$ may be a suitable quencher and $R^7$ may be a suitable fluorophore; m may be an integer from 1 to 5; and p may be an integer from 0 to 5.

In alternative aspects, the invention provides a method for determining exo-glycosidase activity within a cell, the method comprising: (i) providing a test cell and a control cell; (ii) contacting the test cell with a compound of Formula (I), or an acceptable salt thereof:

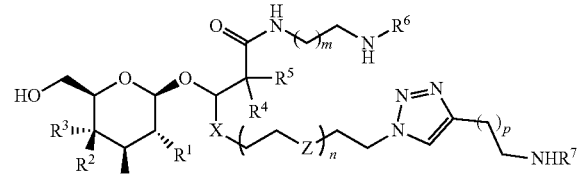

(I)

where X may be O or S; Z may be O or $CH_2$; $R^1$ may be OH or $NHC(O)CH_3$; $R^2$ may be OH and $R^3$ may be H, or $R^2$ may be H and $R^3$ may be OH; $R^4$ may be H or $CH_3$; $R^5$ may be H, OH, or halo; $R^6$ may be a suitable fluorophore and $R^7$ may be a suitable quencher, or $R^6$ may be a suitable quencher and $R^7$ may be a suitable fluorophore; m may be an integer from 1 to 5; n may be an integer from 0 to 2; and p may be an integer from 0 to 5; and (iii) determining fluorescence intensity in the test cell and the control cell, wherein an increase in fluorescence intensity of the test cell when compared to the control cell is indicative of exo-glycosidase activity. In this aspect, the difference in fluorescence intensity between the test cell and the control cell, due to either the compound of Formula (V) or the compound of Formula (VI) in the test cell (Scheme J), is indicative of exo-glycosidase activity. The cells may be derived from a tissue. The tissue may be a skin punch.

In alternative aspects, the invention provides a method for localizing exo-glycosidase activity within a cell, the method comprising: (i) providing a test cell and a control cell; (ii) contacting the test cell with a compound of Formula (I), or an acceptable salt thereof:

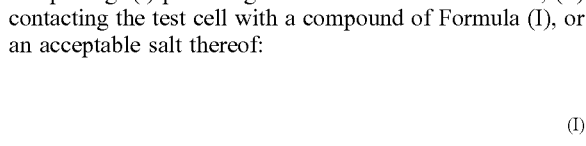

(I)

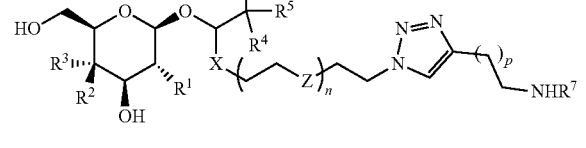

where X may be O or S; Z may be O or $CH_2$; $R^1$ may be OH or $NHC(O)CH_3$; $R^2$ may be OH and $R^3$ may be H, or $R^2$ may be H and $R^3$ may be OH; $R^4$ may be H or $CH_3$; $R^5$ may be H, OH, or halo; $R^6$ may be a suitable fluorophore and $R^7$ may be a suitable quencher, or $R^6$ may be a suitable quencher and $R^7$ may be a suitable fluorophore; m may be an integer from 1 to 5; n may be an integer from 0 to 2; and p may be an integer from 0 to 5; and (iii) visualizing fluorescence intensity in the test cell and the control cell, wherein an increase in fluorescence intensity in a location in the test cell when compared to the fluorescence intensity in a corresponding location in the control cell is indicative of exo-glycosidase activity. In this aspect, the increased fluorescence intensity in a location in the test cell when compared to the fluorescence intensity in a corresponding location in the control cell, due to either the compound of Formula (V) or the compound of Formula (VI) in the test cell (Scheme J), is indicative of exo-glycosidase activity. The location may be the cytosol, nucleus, endoplasmic reticulicum, Golgi apparatus or lysosomal compartments. The cells may be derived from a tissue. The tissue may be a skin punch.

In alternative aspects, the invention provides a method for determining the effect of an exo-glycosidase modulator within a cell, the method comprising: (i) providing a test cell and a control cell; (ii) contacting the test cell with an exo-glycosidase modulator; (iii) contacting the test cell and the control cell with a compound of Formula (I), or an acceptable salt thereof:

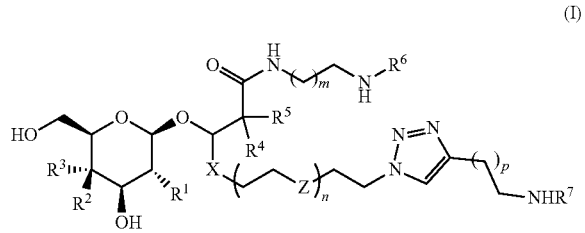

(I)

where X may be O or S; Z may be O or $CH_2$; $R^1$ may be OH or $NHC(O)CH_3$; $R^2$ may be OH and $R^3$ may be H, or $R^2$ may be H and $R^3$ may be OH; $R^4$ may be H or $CH_3$; $R^5$ may be H, OH, or halo; $R^6$ may be a suitable fluorophore and $R^7$ may be a suitable quencher, or $R^6$ may be a suitable quencher and $R^7$ may be a suitable fluorophore; m may be an integer from 1 to 5; n may be an integer from 0 to 2; and p may be an integer from 0 to 5; and (iv) determining fluorescence intensity in the test cell and the control cell, wherein a difference in fluorescence intensity of the test cell when compared to the control cell is indicative of exo-glycosidase modulation. In this aspect, the difference in fluorescence intensity between the test cell and the control cell, due to a difference in concentration of either the compound of Formula (V) or the compound of Formula (VI) between the test cell and the control cell (Scheme J), is indicative of exo-glycosidase modulation. The exo-glycosidase modulator may be an exo-glycosidase inhibitor, or an exo-glycosidase activator, or an exo-glycosidase chaperone. The cells may be derived from a tissue. The tissue may be a skin punch.

In alternative aspects, the invention provides a method for determining the efficacy of an exo-glycosidase-directed therapy, the method comprising: (i) providing a test cell, wherein the test cell is obtained from a subject treated with an exo-glycosidase-directed therapy, and a control cell, wherein the control cell is obtained from a subject not treated with an exo-glycosidase-directed therapy; (ii) contacting the test cell and the control cell with a compound of Formula (I), or an acceptable salt thereof:

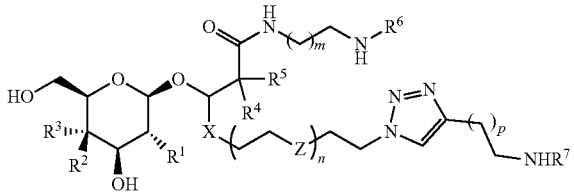

(I)

where X may be O or S; Z may be O or $CH_2$; $R^1$ may be OH or $NHC(O)CH_3$; $R^2$ may be OH and $R^3$ may be H, or $R^2$ may be H and $R^3$ may be OH; $R^4$ may be H or $CH_3$; $R^5$ may be H, OH, or halo; $R^6$ may be a suitable fluorophore and $R^7$ may be a suitable quencher, or $R^6$ may be a suitable quencher and $R^7$ may be a suitable fluorophore; m may be an integer from 1 to 5; n may be an integer from 0 to 2; and p may be an integer from 0 to 5; and (iii) measuring fluorescence intensity in the test cell and the control cell, wherein a difference in fluorescence intensity of the test cell when compared to the control cell is representative of the efficacy of the exo-glycosidase-directed therapy. In this aspect, the difference in fluorescence intensity between the test cell and the control cell, due to a difference in concentration of either the compound of Formula (V) or the compound of Formula (VI) between the test cell and the control cell (Scheme J), is representative of the efficacy of the exo-glycosidase-directed therapy. The cells may be derived from a tissue. The tissue may be a skin punch.

In alternative aspects, the invention provides a method for screening for an exo-glycosidase inhibitor, the method comprising: (i) providing a test cell and a control cell; (ii) contacting the test cell with a test compound; (iii) contacting the test cell and the control cell with a compound of Formula (I), or an acceptable salt thereof:

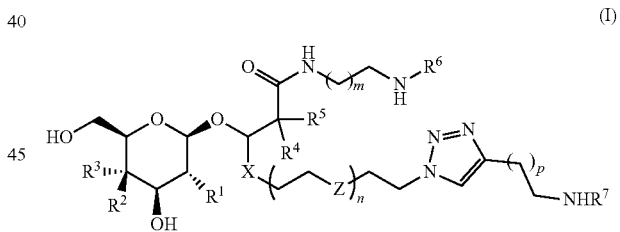

(I)

where X may be O or S; Z may be O or $CH_2$; $R^1$ may be OH or $NHC(O)CH_3$; $R^2$ may be OH and $R^3$ may be H, or $R^2$ may be H and $R^3$ may be OH; $R^4$ may be H or $CH_3$; $R^5$ may be H, OH, or halo; $R^6$ may be a suitable fluorophore and $R^7$ may be a suitable quencher, or $R^6$ may be a suitable quencher and $R^7$ may be a suitable fluorophore; m may be an integer from 1 to 5; n may be an integer from 0 to 2; and p may be an integer from 0 to 5; and (iv) determining fluorescence intensity in the test cell and the control cell, wherein a decrease in fluorescence intensity in the test cell when compared to the control cell indicates that the test compound is an exo-glycosidase inhibitor. In this aspect, a decrease in fluorescence intensity in the test cell compared to the control cell, due to a decrease in concentration of either the compound of Formula (V) or the compound of Formula (VI) in the test cell compared to the control cell (Scheme J), indicates that the test compound is an exo-glycosidase inhibitor.

In alternative aspects, the invention provides a method for screening for an exo-glycosidase activity enhancer, the method comprising: (i) providing a test cell and a control cell; (ii) contacting the test cell with a test compound; (iii) contacting the test cell and the control cell with a compound of Formula (I), or an acceptable salt thereof:

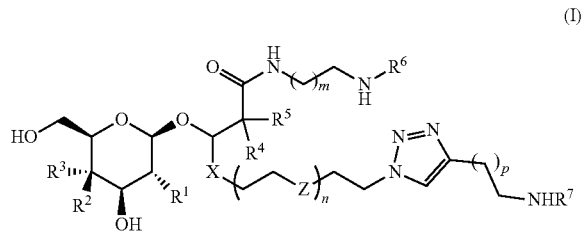

(I)

where X may be O or S; Z may be O or $CH_2$; $R^1$ may be OH or $NHC(O)CH_3$; $R^2$ may be OH and $R^3$ may be H, or $R^2$ may be H and $R^3$ may be OH; $R^4$ may be H or $CH_3$; $R^5$ may be H, OH, or halo; $R^6$ may be a suitable fluorophore and $R^7$ may be a suitable quencher, or $R^6$ may be a suitable quencher and $R^7$ may be a suitable fluorophore; m may be an integer from 1 to 5; n may be an integer from 0 to 2; and p may be an integer from 0 to 5; and (iv) determining fluorescence intensity in the test cell and the control cell, wherein an increase in fluorescence intensity in the test cell when compared to the control cell indicates that the test compound is an exo-glycosidase activity enhancer. In this aspect, an increase in fluorescence intensity in the test cell compared to the control cell, due to an increase in concentration of either the compound of Formula (V) or the compound of Formula (VI) in the test cell compared to the control cell (Scheme J), indicates that the test compound is an exo-glycosidase activity enhancer.

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION OF THE INVENTION

Figure 1:
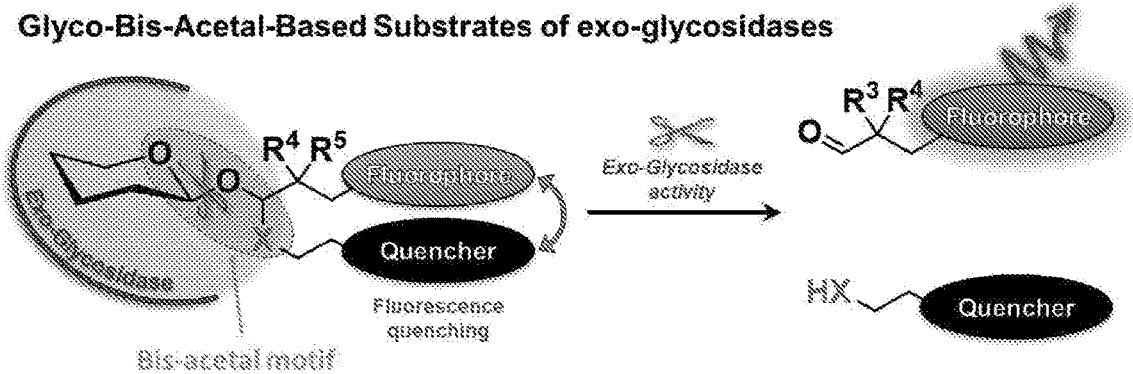
FIG. 1 describes the principle of the Glyco-BABS approach.
Figure 2:
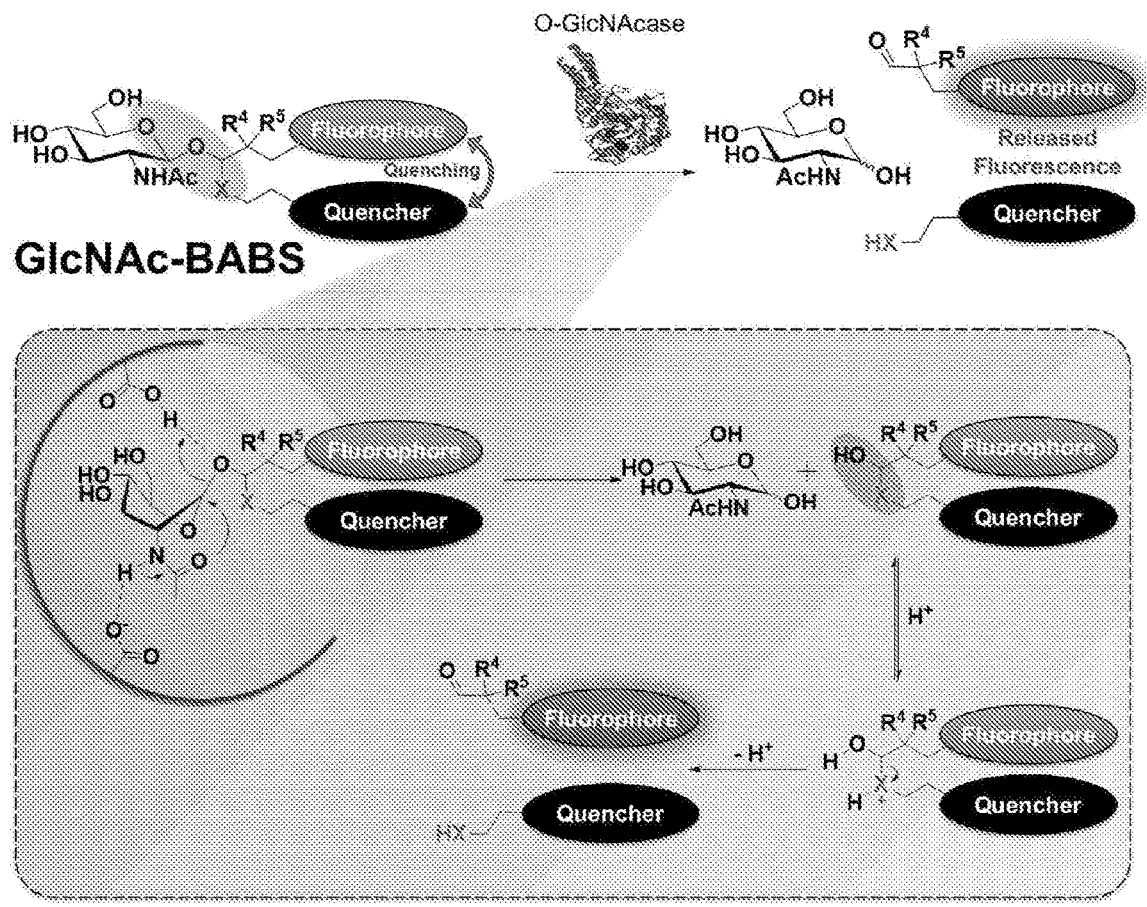
FIG. 2 describes how GlcNAc-BABS are processed by the human O-GlcNAcase (hOGA)

The invention provides, in part, fluorescence-quenched substrates of exo-glycosidase enzymes and uses thereof. In some aspects, such compounds may be useful in methods for monitoring exo-glycosidase activity within cells or tissue, methods for localization of exo-glycosidase activity within different cell compartments including lysosomes, methods for monitoring the effects of an exo-glycosidase inhibitor in cells or tissue, methods for monitoring the effects of an exo-glycosidase chaperone in cells or tissue, methods for monitoring the effects of an exo-glycosidase activator in cells or tissue, methods for monitoring exo-glycosidase activity within cells or tissue as a biomarker for an exo-glycosidase-directed therapy, or methods for conducting a cell-based library screen to identify an exo-glycosidase activity enhancer. In alternative aspects, such compounds may be useful in identifying exo-glycosidase chaperones, studying the trafficking and regulation of exo-glycosidase within cells, screening for endogenous protein modifiers of exo-glycosidase activity, as well as screening for activators that function within cells to influence exo-glycosidase activity.

Exo-Glycosidases and Substrates Thereof

By an "exo-glycosidase" or "exo-glycoside hydrolase" is meant an enzyme with glycosidase activity (EC 3.2.1.x) that catalyzes the hydrolytic cleavage of the beta- or alpha-glycosidic linkage of the terminal glycoside of a glycoprotein, a glyco-lipid, an oligosaccharide or a polysaccharide. In some embodiments, the exo-glycosidase may be a mammalian exo-glycosidase, such as a rat, mouse or human exo-glycosidase. In some embodiments, the exo-glycosidase may be a bacterial exo-glycosidase. The exo-glycosidase may be a wild-type exo-glycosidase or a mutant exo-glycosidase. In some embodiments, the exo-glycosidase may be a wild-type mammalian exo-glycosidase, such as a rat, mouse or human wild-type exo-glycosidase. In some embodiments, the exo-glycosidase may be a mutant mammalian exo-glycosidase, such as a rat, mouse or human mutant exo-glycosidase. In some embodiments, the exo-glycosidase may be a human lysosomal exo-glycosidase. In some embodiments, the exo-glycosidase may be a human non-lysosomal exo-glycosidase. In some embodiments, the exo-glycosidase may be a human cytosolic exo-glycosidase. Examples of human exo-glycosidases include but are not limited to the β-glucocerebrosidase (GBA1 or GCase, EC 3.2.1.45), the non-lysosomal β-glucosylceramidase (GBA2, EC 3.2.1.45), the cytosolic beta-glucosidase (GBA3, EC 3.2.1.21), the acid α-galactosidase (GALA, EC 3.2.1.22), the hexosaminidases A/B (HexA/B, EC 3.2.1.52), the galactosylceramidase (GALC, EC 3.2.1.46), the β-galactosidase (GLB1, EC 3.2.1.23), the hexosaminidase D (HexD, EC 3.2.1.52) or the protein O-GlcNAcase (OGA, EC 3.2.1.169).

By a "substrate" or an "exo-glycosidase substrate" or an "exo-glycosidase substrate molecule" is meant a molecule containing a beta- or alpha-glucosidic linkage that can be hydrolytically cleaved by an exo-glycosidase. By "hydrolytically cleaved" or "hydrolytic cleavage" is meant enzymatic hydrolysis of an $OR_A$ group at the anomeric position of an exo-glycosidase substrate molecule, for example as shown in Scheme A, where $OR_A$ is an organic group that may be enzymatically hydrolyzed by an exo-glycosidase, $R^1$ is OH or $NHC(O)CH_3$, $R^2$ is OH and $R^3$ is H, or $R^2$ is H and $R^3$ is OH.

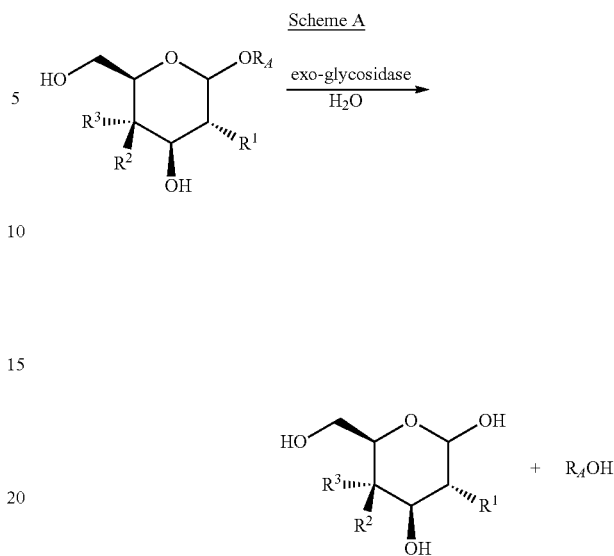

Scheme A

Fluorescence-Quenched Substrates

A "fluorescence-quenched substrate" or a "quenched substrate" is an exo-glycosidase substrate molecule containing a fluorophore and a quencher, such that the initial, intact substrate molecule is not substantially fluorescent due to internal quenching of the fluorophore by the quencher but, upon hydrolytic cleavage by an exo-glycosidase, a cleavage product molecule that contains the fluorophore and exhibits fluorescence is released.

A "Bis-Acetal-Based Substrate" or "BABS" or "Glyco-BABS" is a fluorescence-quenched substrate of an exo-glycosidase in which the fluorophore and quencher are tethered together and linked to the anomeric position through an acetal or a thioacetal group as shown in Scheme B. When considering the presence of the endocyclic oxygen of the pyranose ring, the motif depicted in the oval, indicated at the "bis-acetal motif," in Scheme B can be regarded as a bis-acetal or "hemi-acetal anhydride".

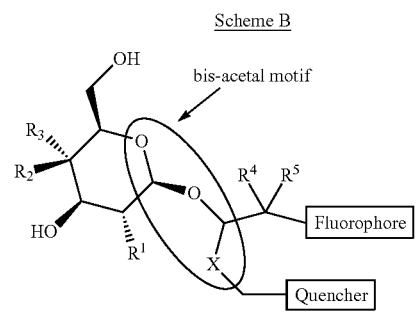

Scheme B where X may be O or S; $R^1$ may be OH or $NHC(O)CH_3$; $R^2$ may be OH and $R^3$ may be H, or $R^2$ may be H and $R^3$ may be OH; $R^4$ may be H or $CH_3$; $R^5$ may be H, OH, or halo.

Accordingly, in some embodiments, by "hydrolytically cleaved" is meant enzymatic hydrolysis of an exo-glycosidase Glyco-BABS molecule as for example shown in Scheme C:

Scheme C

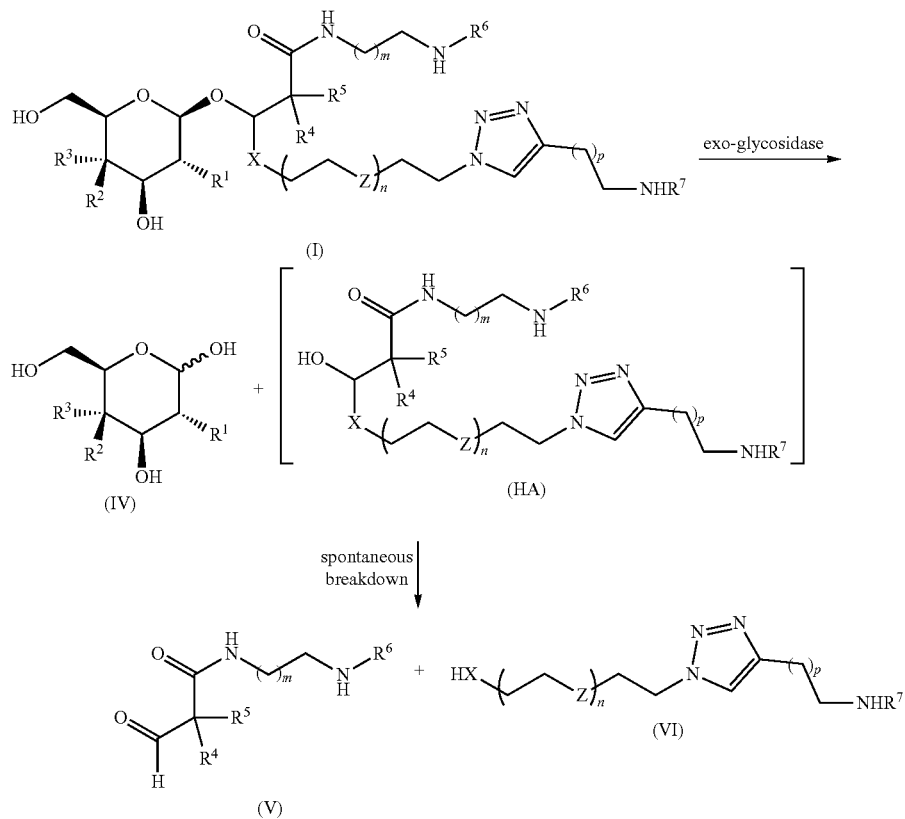

where X may be O or S; Z may be O or $CH_2$; $R^1$ may be OH or $NHC(O)CH_3$; $R^2$ may be OH and $R^3$ may be H, or $R^2$ may be H and $R^3$ may be OH; $R^4$ may be H or $CH_3$; $R^5$ may be H, OH, or halo; $R^6$ may be a suitable fluorophore and $R^7$ may be a suitable quencher, or $R^6$ may be a suitable quencher and $R^7$ may be a suitable fluorophore; m may be an integer from 1 to 5; n may be an integer from 0 to 2; and p may be an integer from 0 to 5. In this aspect, cells or tissue are treated with the fluorescence quenched substrate of Formula (I) (which is not fluorescent, due to internal quenching), and an exo-glycosidase enzyme hydrolytically cleaves the Glyco-BABS of Formula (I) to generate the sugar of Formula (IV) and the unstable hemiacetal intermediate (IIA) which spontaneously breaks down to generate the aldehyde of Formula (V), and the alcohol of Formula (VI). When $R^6$ is a suitable fluorophore, the aldehyde of Formula (V) will be fluorescent, as the fluorophore $R^6$ is no longer internally quenched by the quencher $R^7$. When $R^7$ is a suitable fluorophore, the alcohol of Formula (VI) will be fluorescent, as the fluorophore $R^7$ is no longer internally quenched by the quencher $R^6$. Measuring the fluorescence intensity due to the compound of Formula (V) or the compound of Formula (VI) thus provides a method for monitoring exo-glycosidase activity within cells or tissue.

By a "fluorophore" is meant a chemical group that exhibits fluorescence. By "exhibits fluorescence" is meant that the chemical group absorbs light of a specific wavelength (the excitation or absorption wavelength) and re-emits light at a longer wavelength (the emission wavelength). A fluorophore may exhibit an absorption (or excitation) spectrum and an emission spectrum. The wavelength of maximum excitation or absorption for a fluorophore may be any value between about 150 nm to about 800 nm, or in the range of about 300 nm to about 600 nm, or in the range of about 400 to about 600 nm, or any specific value within any of these ranges, such as 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, or 600 nm. In some embodiments, the excitation or absorption wavelength may be 350 nm. In some embodiments, the excitation or absorption wavelength may be 482 nm. In some embodiments, the excitation or absorption wavelength may be 543 nm. In some embodiments, the excitation or absorption wavelength may be 565 nm. The wavelength of maximum emission for a fluorophore may be any value between about 200 nm to about 900 nm, or in the range of about 300 nm to about 700 nm, or in the range of about 400 to about 600 nm, or any specific value within any of these ranges, such as 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630, nm, 640 nm, 650 nm, 660 nm, 670 nm, 680 nm, 690, or 700 nm. In some embodiments, the emission wavelength may be 490 nm. In some embodiments, the emission wavelength may be 536 nm. In some embodiments, the emission wavelength may be 593 nm. In some embodiments, the emission wavelength may be 610 nm.

In some embodiments, a "suitable" fluorophore may be a fluorophore that can be conjugated to an exo-glycosidase substrate, for example as indicated in Scheme D, Scheme E or Scheme F:

Scheme D

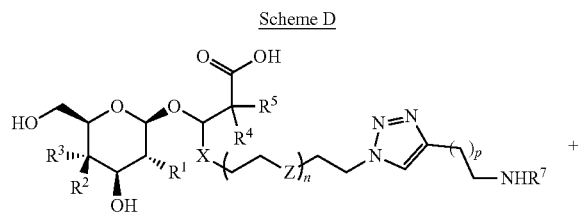

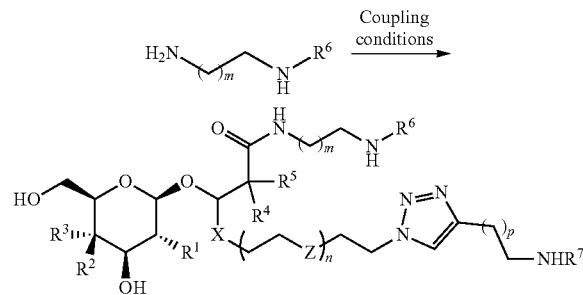

Scheme E

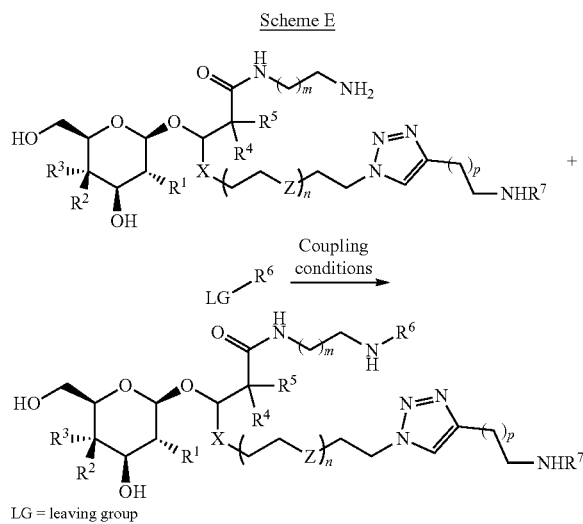

LG = leaving group

Scheme F

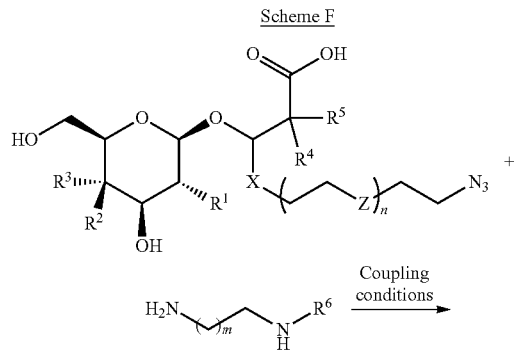

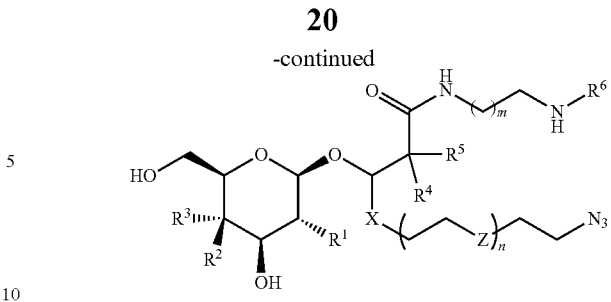

where X may be O or S; Z may be O or $CH_2$; $R^1$ may be OH or $NHC(O)CH_3$; $R^2$ may be OH and $R^3$ may be H, or $R^2$ may be H and $R^3$ may be OH; $R^4$ may be H or $CH_3$; $R^5$ may be H, OH, or halo; $R^6$ may be a fluorophore and $R^7$ may be a quencher or a protecting group; m may be an integer from 1 to 5; n may be an integer from 0 to 2; and p may be an integer from 0 to 5.

In some embodiments, a "suitable" fluorophore may be a fluorophore having a boron-dipyrromethene (BODIPY®), a carboxytetramethylrhodamine (TAMRA) or a 5-sulfonaphthalen-1-yl group at either the $R^6$ or the $R^7$ position as indicated in Scheme C.

In some embodiments, a suitable fluorophore may include one or more of the following: 5-sulfonaphthalen-1-yl, 5-[(2-azidoethyl)amino]naphthalene-1-sulfonic acid (EDANS), 3-(5,5-difluoro-7-(1H-pyrrol-2-yl)-5H-dipyrrolo[1,2-c:2',1'-f][1,3,2]diazaborinin-4-ium-5-uid-3-yl)propanoyl, Carboxytetramethylrhodamine (TAMRA), boron-dipyrromethene (BODIPY®) 576/589, BODIPY® FL, BODIPY® R6G, BODIPY® TMR-X, BODIPY® 581/591, BODIPY® TR-X, BODIPY® 630/665-X, FAM, TET, HEX, JOE, VIC, NED, TMR, ROX, TAMRA, CAL Fluor Gold 540, CAL Fluor Orange 560, CAL Red, CAL Orange, CAL Gold, Cy3, Cy3.5, Cy5, Cy5.5, Quasar 570, Quasar 670, Pulsar-650, Oyster 556, Oyster 645, CAL Fluor Red 590, CAL Fluor Red 635, CAL Fluor Red 610, CAL Fluor Red 610, Texas red, LC red 610, LC red 610, LC red 640, LC red 670, LC red 705, Oregon Green 488, Oregon Green 514, Rhodamine Green, Yakima Yellow, Rhodamine Red-X, or Redmond Red, including fluorophores described herein or known in the art.

By a "quencher" is meant a chemical group that absorbs light at, or close to, the emission wavelength of the fluorophore in the fluorescence-quenched substrate, as described herein. In some embodiments, a quencher may be a complementary quencher, that is, a quencher that absorbs energy at, or close to, the emission wavelength of the fluorophore. In some embodiments, a quencher may be a dark quencher, that is, a chemical group that absorbs energy at, or close to, the emission wavelength of the fluorophore and dissipates the energy as heat (i.e. nonradiatively). In some embodiments, a quencher may be a fluorescent quencher, that is, a chemical group that absorbs energy at, or close to, the emission wavelength of the fluorophore and dissipates the energy as light (i.e. the fluorescent quencher absorbs light at the emission wavelength of a suitable fluorophore and re-emits light at a longer wavelength). In some embodiments, a "suitable" quencher may be a quencher that can be conjugated to an exo-glycosidase substrate, for example as indicated in Scheme G, Scheme H or Scheme I:

Scheme G

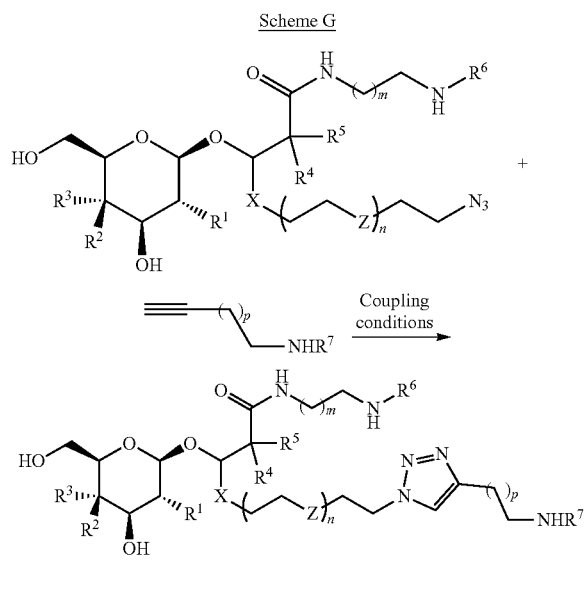

Scheme H

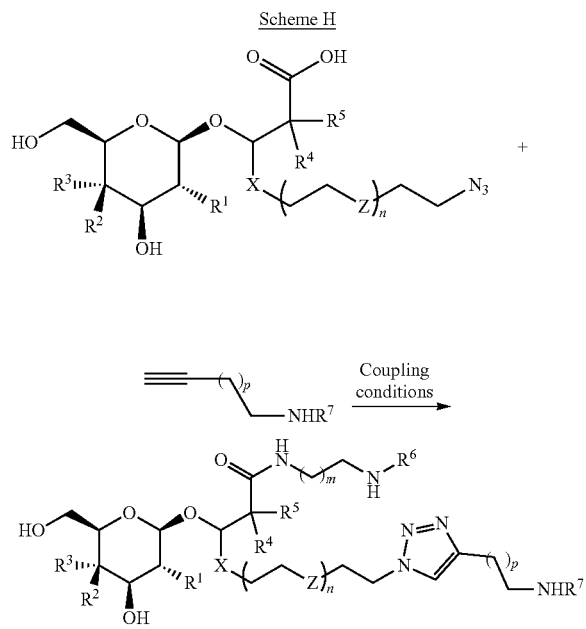

Scheme I

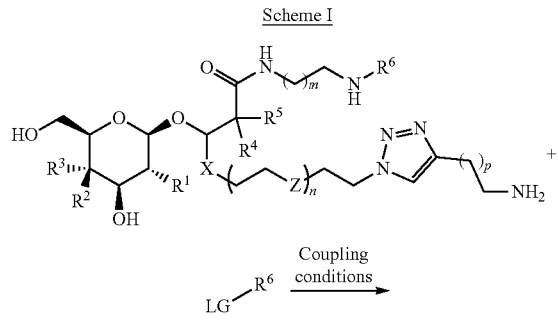

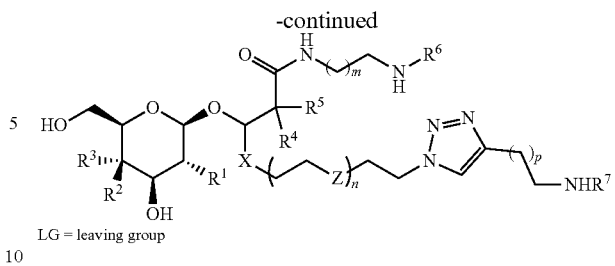

LG = leaving group where X may be O or S; Z may be O or CH$_2$; R$^1$ may be OH or NHC(O)CH$_3$; R$^2$ may be OH and R$^3$ may be H, or R$^2$ may be H and R$^3$ may be OH; R$^4$ may be H or CH$_3$; R$^5$ may be H, OH, or halo; R$^6$ may be a fluorophore or a protecting group and R$^7$ may be a quencher; m may be an integer from 1 to 5; n may be an integer from 0 to 2; and p may be an integer from 0 to 5.

In some embodiments, a "suitable" quencher may be a quencher having a dimethylaminoazobenzenesulfonic acid (DABCYL) or 4-((4-((E)-(2,5-dimethoxy-4-((E)-(4-nitrophenyl)diazenyl)phenyl)diazenyl)phenyl)(methyl)amino)-butanoyl (BHQ®2) group at the R$^7$ position, as indicated in Scheme C.

In some embodiments, a suitable quencher may be DABSYL (dimethylaminoazobenzenesulfonic acid). In some embodiments, a suitable quencher may be Black Hole Quencher® 2 (BHQ®2, 4-((4-((E)-(2,5-dimethoxy-4-((E)-(4-nitrophenyl)diazenyl)phenyl)diazenyl)phenyl)(methyl) amino)-butanoic acid). In some embodiments, a "suitable quencher" may include one or more of the following: 4-([4-(dimethylamino)phenyl]azo)-benzoic acid (DABCYL), (E)-4-((4-(dimethylamino)phenyl)diazenyl) benzoyl, 4-((4-((E)-(2,5-dimethoxy-4-((E)-(4-nitrophenyl) diazenyl)phenyl)diazenyl)phenyl)(methyl)amino)-butanoyl, Black Hole Quencher® 2 (BHQ®2), DDQ-I, DDQ-II, Eclipse, ElleQuencher, Iowa Black FQ, Iowa Black RQ, BHQ®0, BHQ®1, BHQ®3, QSY-7, QSY 9, QSY-21, or QSY 35, including quenchers described herein or known in the art. A discussion of fluorophore and quencher groups may be found, for example, in "The Molecular Probes Handbook, A Guide to Fluorescent Probes and Labeling Technologies" I. Johnson and M. T. Z. Spence (eds.), Eleventh Edition (Life Technologies, 2010).

By "not substantially fluorescent" is meant a molecule that exhibits efficient internal quenching. By "efficient internal quenching" or "efficient quenching" or "internal quenching" is meant decreased intensity of fluorescent emission due to the presence of the quencher within the substrate molecule. The decrease in fluorescent emission may be a decrease by any value between about 10% and about 100%, or of any value between about 30% and about 60%, or about 100%, or a decrease by about 1-fold, 2-fold, 5-fold, 10-fold, 100-fold, 1000-fold, 10,000-fold, 100,000-fold, or more, or by about 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.99%, 99.999%, 99.9999%, or more in comparison to a reference sample or compound, or in comparison to a cleavage product molecule such as, for example, either a compound of Formula (V) or a compound of Formula (VI). It is to be understood that the decrease in fluorescent emission does not require full absence of fluorescent emission. Examples of suitable reference compounds or controls include, for example, EDANS, EDANS-azide, TAMRA, TAMRA-amine, BODIPY® 576/589, or BODIPY®-NHS.

A cleavage product molecule for a fluorescence-quenched substrate such as, for example, a compound of Formula (V) or a compound of Formula (VI) may exhibit significant fluorescent emission. By "significant fluorescent emission" is meant a fluorescent intensity in the range of about 0.1 to about 1×10$^9$ relative fluorescence units (RFU), or in the range of about 10 RFU to about 1×10$^8$ RFU, or in the range of about 100 RFU to about 1×10$^6$ RFU, or in the range of about 100 RFU to about 5,000 RFU, or any specific fluorescent intensity within any of these ranges, such as 50 RFU, 60 RFU, 70 RFU, 80 RFU, 90 RFU, 100 RFU, 110 RFU, 120 RFU, 130 RFU, 140 RFU, 150 RFU, 160 RFU, 170 RFU, 180 RFU, 190 RFU, 200 RFU, 300 RFU, 400 RFU, 500 RFU, 600 RFU, 700 RFU, 800 RFU, 900 RFU, 1,000 RFU, 2,000 RFU, 3,000 RFU, 4,000 RFU, 5,000 RFU, 10,000 RFU, 50,000 RFU, 100,000 RFU, 500,000 RFU, 1×10$^6$ RFU, 0.5×10$^7$ RFU, 1×10$^7$ RFU, 0.5×10$^8$ RFU, 1×10$^8$ RFU, 0.5×10$^9$ RFU, 1×10$^9$ RFU, or any value within or about the described range. The fluorescent intensity may be measured based on concentration of cleavage product molecule, number of cells, amount of tissue, or any other suitable unit for measuring fluorescent intensity.

In some embodiments, one or more of the compounds according to the invention may be a selective exo-glycosidase substrate. By a "selective exo-glycosidase substrate" is meant an exo-glycosidase substrate molecule containing a beta- or alpha-glucosidic linkage that may be specifically hydrolytically cleaved by an exo-glycosidase. In alternative embodiments, one or more of the compounds according to the invention may be specifically cleaved by one exo-glycosidase and not cleaved by other exo-glycosidases belonging to the same family. By "other exo-glycosidases belonging to the same family" is meant other exo-glycosidases that may be sharing the same Enzyme commission number (EC), that may belong to the same glycoside hydrolase (GH) family according to the CAZy database$^1$, or that may cleave the same terminal glycoside. In alternative embodiments, one or more of the compounds according to the invention may be specifically cleaved by one isoform of an exo-glycosidase, for example the human lysosomal GBA1 isoform. In alternative embodiments, one or more of the compounds according to the invention may be specifically cleaved by the human lysosomal GBA1 isoform over the human non-lysosomal GBA2 isoform and/or the human cytosolic GBA3 isoform. By "specifically hydrolytically cleaved" or "specifically cleaved" is meant a compound that is hydrolytically cleaved by an exo-glycosidase but is not substantially hydrolytically cleaved by other enzymes in a sample, such as a lactase, a sucrase, an isomaltase, an alpha-glucosidase II, a glycogen phosphorylase, an acid alpha-glucosidase, an alpha-galactosidase, a beta-galactosidase, a beta-hexosaminidase, an O-GlcNAcase, or another exo-glycosidase isoform. By "not substantially hydrolytically cleaved" is meant a substrate specificity in the range of about 2-fold to about 100,000-fold, or about 10-fold to about 100,000-fold, or in the range of about 100-fold to about 100,000-fold, or in the range of about 1000-fold to about 100,000-fold, or at least about 2-fold, 3-fold, 4-fold, 5-fold, 10-fold, 20-fold, 50-fold, 100-fold, 200-fold, 500-fold, 1000-fold, 1500-fold, 2000-fold, 2500-fold, 3000-fold, 3500-fold, 4000-fold, 4500-fold, 5000-fold, 6000-fold, 7000-fold, 10,000-fold, 25,000-fold, 50,000-fold, 75,000-fold, or any value within or about the described range, where "substrate specificity" means the ratio of the respective $k_{cat}/K_m$ constants, that is, $$[k_{cat(exo\text{-}glycosidase)}/K_{m(exo\text{-}glycosidase)}]/[k_{cat(other\ enzyme)}/K_{m(other\ enzyme)}]$$

where "$k_{cat(exo\text{-}glycosidase)}$" is the rate constant for cleavage of a substrate molecule by an exo-glycosidase, "$K_{m(exo\text{-}glycosidase)}$" is the Michaelis constant for a substrate molecule and an exo-glycosidase, "$k_{cat(other\ enzyme)}$" is the rate constant for cleavage of a substrate molecule by another enzyme, and "$K_{m(other\ enzyme)}$" is the Michaelis constant for a substrate molecule and another enzyme.

In specific embodiments, the invention provides compounds described generally by Formula (I) and salts thereof:

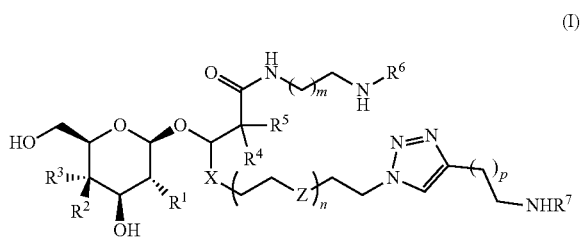

(I)

As set forth in Formula (I): where X may be O or S; Z may be O or CH$_2$; R$^1$ may be OH or NHC(O)CH$_3$; R$^2$ may be OH and R$^3$ may be H, or R$^2$ may be H and R$^3$ may be OH; R$^4$ may be H or CH$_3$; R$^5$ may be H, OH, or halo; R$^6$ may be a suitable fluorophore and R$^7$ may be a suitable quencher, or R$^6$ may be a suitable quencher and R$^7$ may be a suitable fluorophore; m may be an integer from 1 to 5; n may be an integer from 0 to 2; and p may be an integer from 0 to 5.

In some embodiments, X as set forth in Formula (I) may be O or S. In some embodiments, X may be O.

In some embodiments, Z as set forth in Formula (I) may be O or CH$_2$. In some embodiments, Z may be O.

In some embodiments, R$^1$ as set forth in Formula (I) may be OH or NHC(O)CH$_3$. In some embodiments, R$^1$ may be OH. In some embodiments, R$^1$ may be NHC(O)CH$_3$.

In some embodiments, R$^2$ as set forth in Formula (I) may be OH and R$^3$ as set forth in Formula (I) may be H. In some embodiments, R$^2$ may be H and R$^3$ may be OH.

In some embodiments, R$^4$ as set forth in Formula (I) may be H or CH$_3$. In some embodiments, R$^4$ may be H. In some embodiments, R$^4$ may be CH$_3$.

In some embodiments, R$^5$ as set forth in Formula (I) may be H, OH, or halo. In some embodiments, R$^5$ may be H. In some embodiments, R$^5$ may be OH. In some embodiments, R$^5$ may be Br.

In some embodiments, R$^6$ as set forth in Formula (I) may be a suitable fluorophore and R$^7$ as set forth in Formula (I) may be a suitable quencher.

In some embodiments, R$^6$ as set forth in Formula (I) may be a suitable quencher and R$^7$ as set forth in Formula (I) may be a suitable fluorophore.

In some embodiments, R$^6$ as set forth in Formula (I) may be 5-sulfonaphthalen-1-yl or (2-(6-(dimethylamino)-3-(dimethyliminio)-3H-xanthen-9-yl)benzoate)-5-carbonyl.

In some embodiments, R$^7$ as set forth in Formula (I) may be a be (E)-4-((4-(dimethylamino)phenyl)diazenyl)benzoyl or 4-((4-((E)-(2,5-dimethoxy-4-((E)-(4-nitrophenyl)diazenyl)phenyl)diazenyl)phenyl)(methyl)amino)-butanoyl.

In some embodiments, m as set forth in Formula (I) may be an integer from 1 to 5. In some embodiments, m may be 1, 2, 3, 4, or 5. In some embodiments, m may be 1. In some embodiments, m may be 5.

In some embodiments, n as set forth in Formula (I) may be an integer from 0 to 2. In some embodiments, n may be 0, 1, or 2. In some embodiments, n may be 1.

In some embodiments, p as set forth in Formula (I) may be an integer from 0 to 5. In some embodiments, p may be 0, 1, 2, 3, 4, or 5. In some embodiments, p may be 0.

In specific embodiments of the invention, compounds according to Formula (I) include the compounds described in Table 1.

TABLE 1

| Example | Structure/Name |
|---|---|
| 1 | 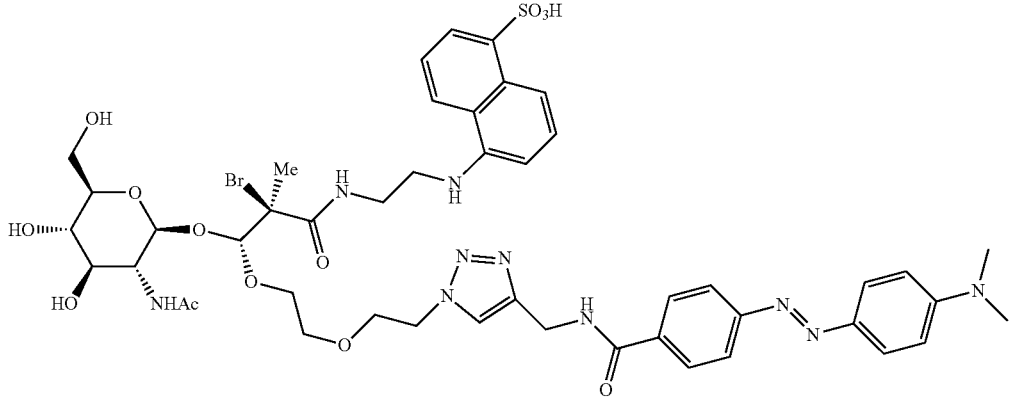 GlcNAc-Br-BABS(EDANS/DABCYL), 5-((2-((2R,3R)-3-(((2S,3R,4R,5S,6R)-3-acetamido-4,5-dihydroxy-6-(hydroxymethyl)tetrahydro-2H-pyran-2-yl)oxy)-2-bromo-3-(2-(2-(4-((4-((E)-(4-(dimethylamino)phenyl)diazenyl)benzamido)methyl)-1H-1,2,3-triazol-1-yl)ethoxy)ethoxy)-2-methylpropanamido)ethyl)amino)naphthalene-1-sulfonic acid; Compound 1 |
| 2 | 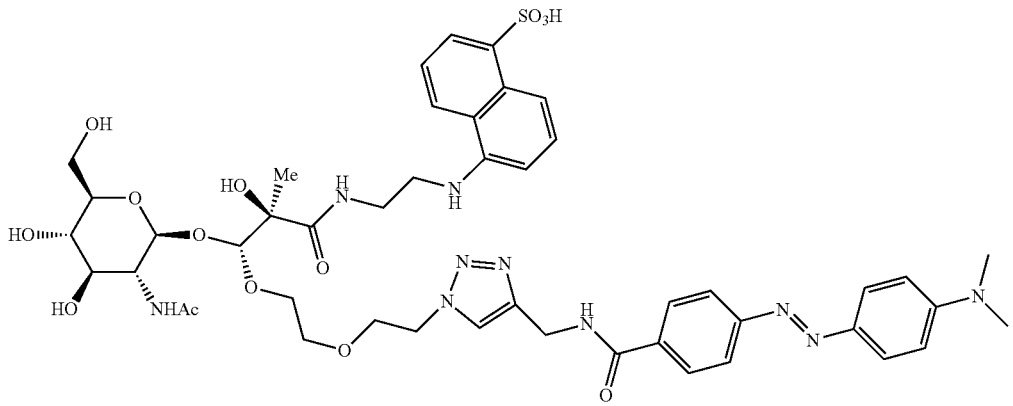 GlcNAc-OH-BABS(EDANS/DABCYL), 5-((2-((2R,3R)-3-(((2S,3R,4R,5S,6R)-3-acetamido-4,5-dihydroxy-6-(hydroxymethyl)tetrahydro-2H-pyran-2-yl)oxy)-3-(2-(2-(4-((4-((E)-(4-(dimethylamino)phenyl)diazenyl)benzamido)methyl)-1H-1,2,3-triazol-1-yl)ethoxy)ethoxy)-2-hydroxy-2-methylpropanamido)ethyl)amino)naphthalene-1-sulfonic acid; Compound 2 |

TABLE 1-continued

| Example | Structure/Name |
|---|---|
| 3 | 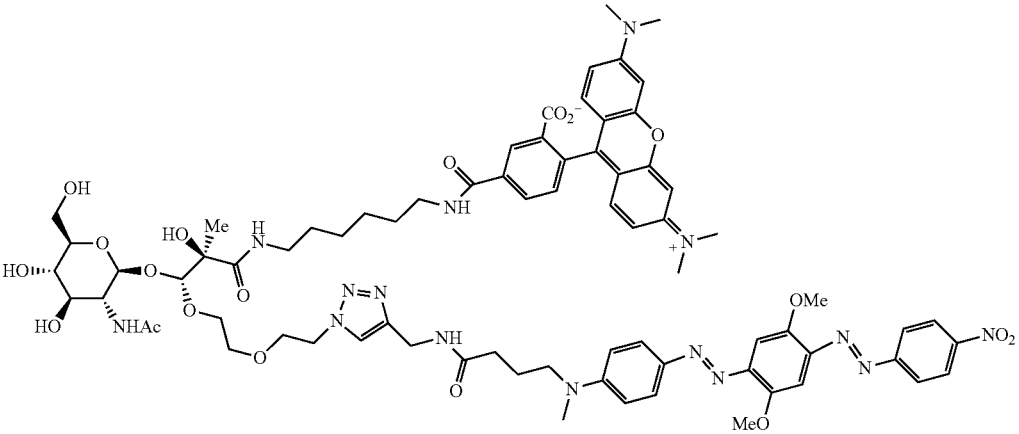<br>GlcNAc-OH-BABS(TAMRA/BHQ2), 5-((6-(((2R,3R)-3-(((2S,3R,4R,5S,6R)-3-acetamido-4,5-dihydroxy-6-(hydroxymethyl)tetrahydro-2H-pyran-2-yl)oxy)-3-(2-(2-(4-((4-((4-((E)-(2,5-dimethoxy-4-((E)-(4-nitrophenyl)diazenyl)phenyl)diazenyl)phenyl)(methyl)amino)butanamido)methyl)-1H-1,2,3-triazol-1-yl)ethoxy)ethoxy)-2-hydroxy-2-methylpropanamido)hexyl)carbamoyl)-2-(6-(dimethylamino)-3-(dimethyliminio)-3H-xanthen-9-yl)benzoate; Compound 3 |
| 4 | 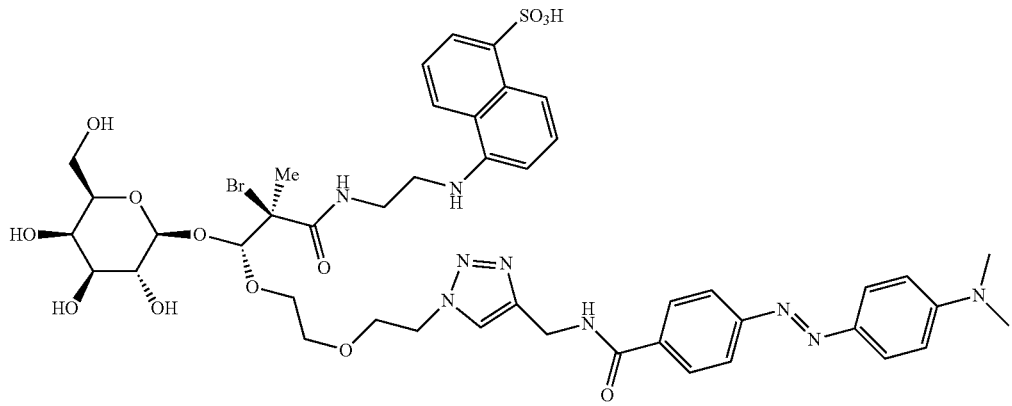<br>Gal-Br-BABS(EDANS/DABCYL), 5-((2-((2R,3R)-2-bromo-3-(2-(2-(4-((4-((E)-(4-(dimethylamino)phenyl)diazenyl)benzamido)methyl)-1H-1,2,3-triazol-1-yl)ethoxy)ethoxy)-2-methyl-3-(((2S,3R,4S,5R,6R)-3,4,5-trihydroxy-6-(hydroxymethyl)tetrahydro-2H-pyran-2-yl)oxy)propanamido)ethyl)amino)naphthalene-1-sulfonic acid; Compound 4 |

TABLE 1-continued

| Example | Structure/Name |
|---|---|
| 5 | 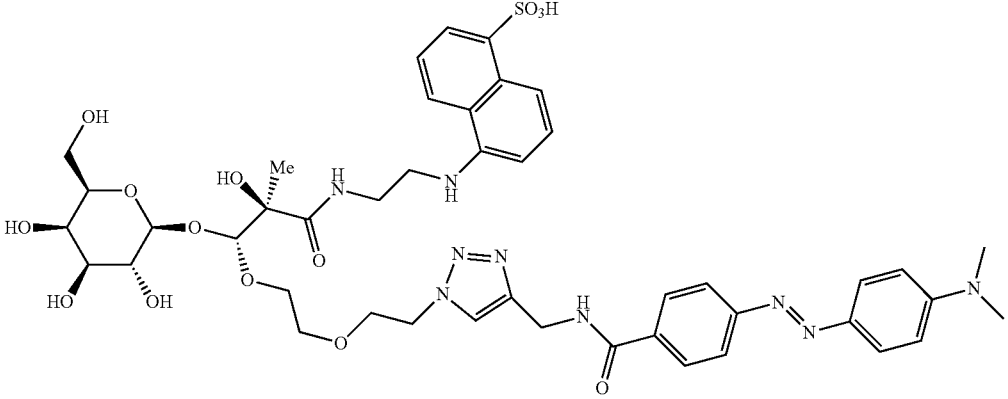<br>Gal-OH-BABS(EDANS/DABCYL), 5-((2-((2R,3R)-3-(2-(2-(4-((4-(E)-(4-(dimethylamino)phenyl)diazenyl)benzamido)methyl)-1H-1,2,3-triazol-1-yl)ethoxy)ethoxy)-2-hydroxy-2-methyl-3-(((2S,3R,4S,5R,6R)-3,4,5-trihydroxy-6-(hydroxymethyl)tetrahydro-2H-pyran-2-yl)oxy)propanamido)ethyl)amino)naphthalene-1-sulfonic acid; Compound 5 |
| 6 | 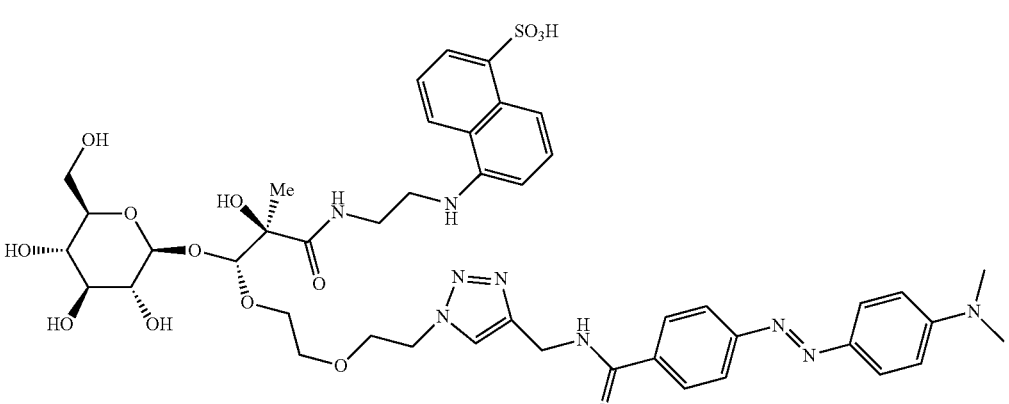<br>Glc-OH-BABS(EDANS/DABCYL), 5-((2-((2R,3R)-3-(2-(2-(4-((4-((E)-(4-(dimethylamino)phenyl)diazenyl)benzamido)methyl)-1H-1,2,3-triazol-1-yl)ethoxy)ethoxy)-2-hydroxy-2-methyl-3-(((2S,3R,4S,5S,6R)-3,4,5-trihydroxy-6-(hydroxymethyl)tetrahydro-2H-pyran-2-yl)oxy)propanamido)ethyl)amino)naphthalene-1-sulfonic acid; Compound 6 |
| 7 | 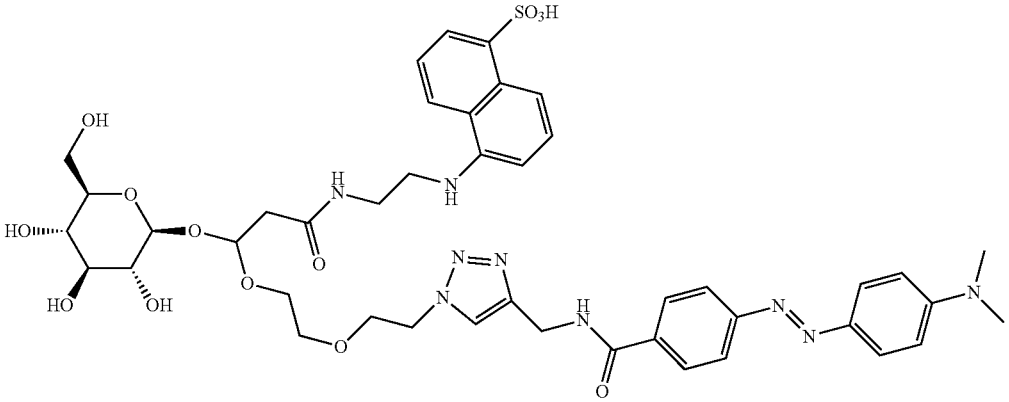<br>Glc-H-BABS(EDANS/DABCYL), 5-((2-(3-(2-(2-(4-((4-((E)-(4-(dimethylamino)phenyl)diazenyl)benzamido)methyl)-1H-1,2,3-triazol-1-yl)ethoxy)ethoxy)-3-(((2S,3R,4S,5S,6R)-3,4,5-trihydroxy-6-(hydroxymethyl)tetrahydro-2H-pyran-2-yl)oxy)propanamido)ethyl)amino)naphthalene-1-sulfonic acid; Compound 7 |

TABLE 1-continued

| Example | Structure/Name |
|---|---|
| 8 | 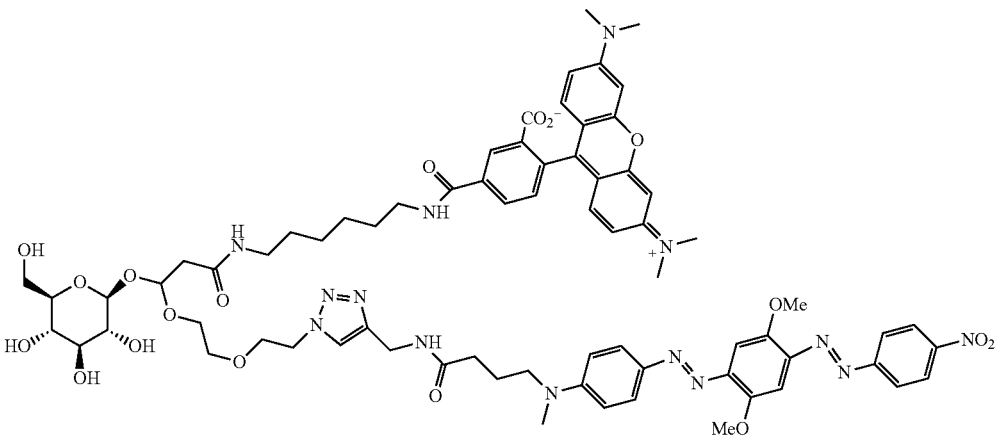<br>Glc-H-BABS(TAMRA/BHQ2), 5-((6-(3-(2-(2-(4-((4-((4-((E)-(2,5-dimethoxy-4-((E)-(4-nitrophenyl)diazenyl)phenyl)diazenyl)phenyl)(methyl)amino)butanamido)methyl)-1H-1,2,3-triazol-1-yl)ethoxy)ethoxy)-3-(((2S,3R,4S,5S,6R)-3,4,5-trihydroxy-6-(hydroxymethyl)tetrahydro-2H-pyran-2-yl)oxy)propanamido)hexyl)carbamoyl)-2-(6-(dimethylamino)-3-(dimethyliminio)-3H-xanthen-9-yl)benzoate; Compound 8 |
| 9 | 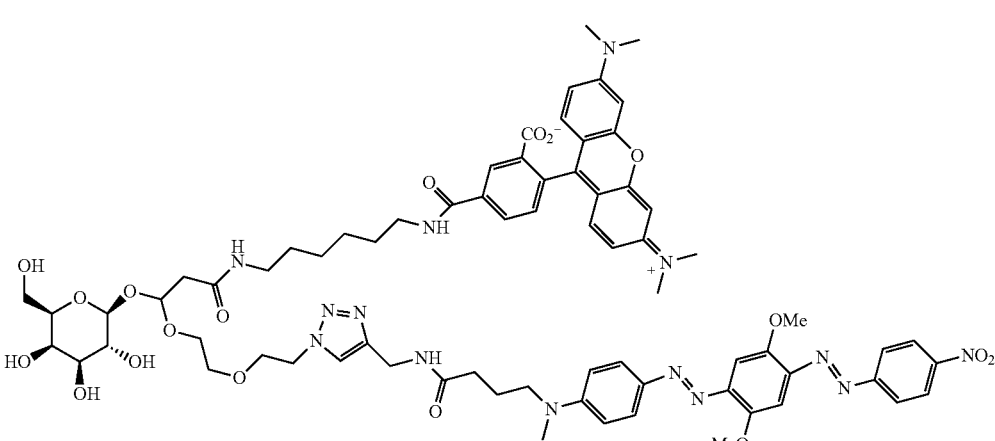<br>Gal-H-BABS(TAMRA/BHQ2), 5-((6-(3-(2-(2-(4-((4-((4-((E)-(2,5-dimethoxy-4-((E)-(4-nitrophenyl)diazenyl)phenyl)diazenyl)phenyl)(methyl)amino)butanamido)methyl)-1H-1,2,3-triazol-1-yl)ethoxy)ethoxy)-3-(((2S,3R,4S,5R,6R)-3,4,5-trihydroxy-6-(hydroxymethyl)tetrahydro-2H-pyran-2-yl)oxy)propanamido)hexyl)carbamoyl)-2-(6-(dimethylamino)-3-(dimethyliminio)-3H-xanthen-9-yl)benzoate; Compound 9 |

TABLE 1-continued

| Example | Structure/Name |
|---|---|
| 10 | 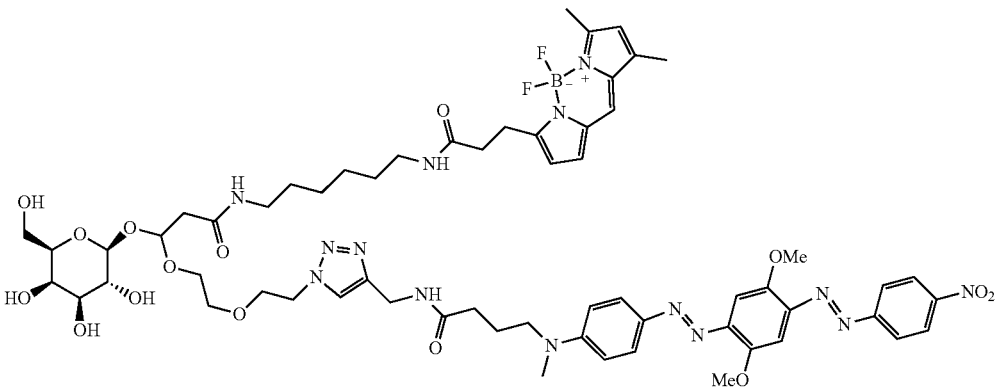 Gal-H-BABS(BDPFL/BHQ2), N-((1-(20-(5,5-difluoro-7,9-dimethyl-5H-5l4,6l4-dipyrrolo[1,2-c:2′,1′-f][1,3,2]diazaborinin-3-yl)-9,18-dioxo-7-(((2S,3R,4S,5R,6R)-3,4,5-trihydroxy-6-(hydroxymethyl)tetrahydro-2H-pyran-2-yl)oxy)-3,6-dioxa-10,17-diazaicosyl)-1H-1,2,3-triazol-4-yl)methyl)-4-((4-((E)-(2,5-dimethoxy-4-((E)-(4-nitrophenyl)diazenyl)phenyl)diazenyl)phenyl)(methyl)amino)butanamide; Compound 10 |
| 11 | 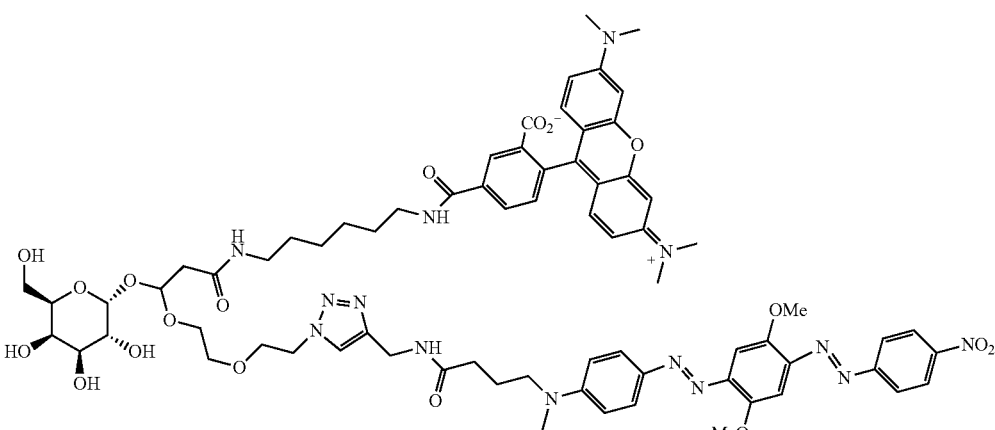 α-Gal-H-BABS(TAMRA/BHQ2), 5-((6-(3-(2-(2-(4-((4-((4-((E)-(2,5-dimethoxy-4-((E)-(4-nitrophenyl)diazenyl)phenyl)diazenyl)phenyl)(methyl)amino)butanamido)methyl)-1H-1,2,3-triazol-1-yl)ethoxy)ethoxy)-3-(((2R,3R,4S,5R,6R)-3,4,5-trihydroxy-6-(hydroxymethyl)tetrahydro-2H-pyran-2-yl)oxy)propanamido)hexyl)carbamoyl)-2-(6-(dimethylamino)-3-(dimethyliminio)-3H-xanthen-9-yl)benzoate; Compound 11 |

TABLE 1-continued

| Example | Structure/Name |
|---|---|
| 12 | 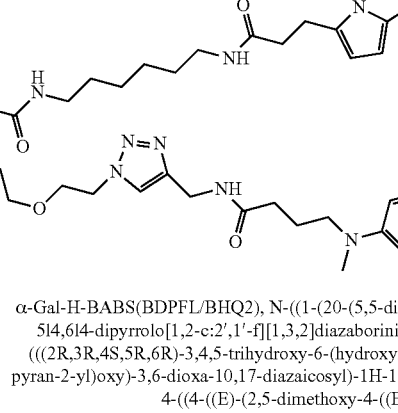
α-Gal-H-BABS(BDPFL/BHQ2), N-((1-(20-(5,5-difluoro-7,9-dimethyl-5H-5l4,6l4-dipyrrolo[1,2-c:2′,1′-f][1,3,2]diazaborinin-3-yl)-9,18-dioxo-7-(((2R,3R,4S,5R,6R)-3,4,5-trihydroxy-6-(hydroxymethyl)tetrahydro-2H-pyran-2-yl)oxy)-3,6-dioxa-10,17-diazaicosyl)-1H-1,2,3-triazol-4-yl)methyl)-4-((4-((E)-(2,5-dimethoxy-4-((E)-(4-nitrophenyl)diazenyl)phenyl)diazenyl)phenyl)(methyl)amino)butanamide; Compound 12 |
| 13 | 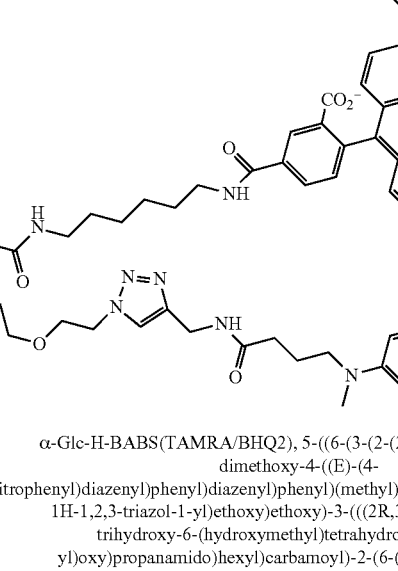
α-Glc-H-BABS(TAMRA/BHQ2), 5-((6-(3-(2-(2-(4-((4-((E)-(2,5-dimethoxy-4-((E)-(4-nitrophenyl)diazenyl)phenyl)diazenyl)phenyl)(methyl)amino)butanamido)methyl)-1H-1,2,3-triazol-1-yl)ethoxy)ethoxy)-3-(((2R,3R,4S,5S,6R)-3,4,5-trihydroxy-6-(hydroxymethyl)tetrahydro-2H-pyran-2-yl)oxy)propanamido)hexyl)carbamoyl)-2-(6-(dimethylamino)-3-(dimethyliminio)-3H-xanthen-9-yl)benzoate; Compound 13 |

TABLE 1-continued

| Example | Structure/Name |
|---|---|
| 14 | 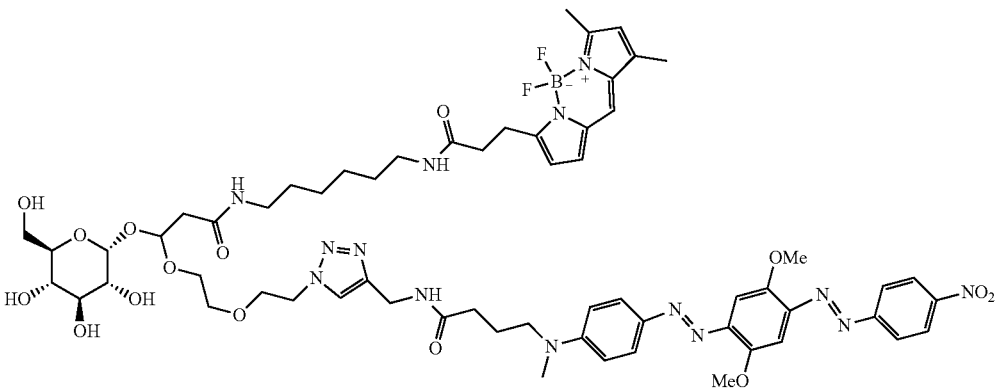<br>α-Glc-H-BABS(BDPFL/BHQ2), N-((1-(20-(5,5-difluoro-7,9-dimethyl-5H-5l4,6l4-dipyrrolo[1,2-c:2',1'-f][1,3,2]diazaborinin-3-yl)-9,18-dioxo-7-(((2R,3R,4S,5S,6R)-3,4,5-trihydroxy-6-(hydroxymethyl)tetrahydro-2H-pyran-2-yl)oxy)-3,6-dioxa-10,17-diazaicosyl)-1H-1,2,3-triazol-4-yl)methyl)-4-((4-((E)-(2,5-dimethoxy-4-((E)-(4-nitrophenyl)diazenyl)phenyl)diazenyl)phenyl)(methyl)amino)butanamide; Compound 14 |

A compound of the present invention may be used in the form of a salt. In such cases, compositions in accordance with this invention may comprise a salt of such a compound, preferably a physiologically-acceptable salt, which are known in the art. In some embodiments, an "acceptable salt" as used herein means an active ingredient comprising compounds of Formula (I) used in the form of a salt thereof, particularly where the salt form confers on the active ingredient improved solubility, bioavailability or cell permeability properties as compared to the free form of the active ingredient or other previously disclosed salt form.

An "acceptable salt" may include both acid and base addition salts. An "acceptable acid addition salt" refers to those salts which retain the biological effectiveness and properties of the free bases, which are not biologically or otherwise undesirable, and which may be formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

An "acceptable base addition salt" refers to those salts which may retain the biological effectiveness and properties of the free acids, which may not be biologically or otherwise undesirable. These salts may be prepared from addition of an inorganic base or an organic base to the free acid. Salts derived from inorganic bases may include, but are not limited to, the sodium, potassium, lithium, ammonium, calcium, magnesium, iron, zinc, copper, manganese, aluminum salts and the like. Preferred inorganic salts may be the ammonium, sodium, potassium, calcium, and magnesium salts. Salts derived from organic bases may include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases may be isopropylamine, diethylamine, ethanolamine, trimethylamine, dicyclohexylamine, choline and caffeine.

Thus, the term "acceptable salt" encompasses all acceptable salts including but not limited to acetate, lactobionate, benzenesulfonate, laurate, benzoate, malate, bicarbonate, maleate, bisulfate, mandelate, bitartrate, mesylate, borate, methylbromide, bromide, methylnitrite, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutame, stearate, glycollylarsanilate, sulfate, hexylresorcinate, subacetate, hydradamine, succinate, hydrobromide, tannate, hydrochloride, tartrate, hydroxynaphthoate, teoclate, iodide, tosylate, isothionate, triethiodide, lactate, panoate, valerate, and the like.

Acceptable salts of a compound of the present invention may be used for modifying solubility or hydrolysis characteristics. Also, salts of a compound of this invention may include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

"Halo" refers to bromo, chloro, fluoro, iodo, etc. In some embodiments, suitable halogens include bromine, fluorine or chlorine.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

Fluorescence-quenched Bis-Acetal-Based substrates, such as compounds according to the invention, may be prepared using standard techniques as described herein or known in the art.

Methods for Use of Fluorescence-Quenched Substrates

A fluorescence-quenched exo-glycosidase Glyco-BABS, for example, an exo-glycosidase Glyco-BABS which could enable the enzyme to turn over multiple molecules, may be used to assess the enzymatic activity of an exo-glycosidase within a live cell or tissue. Accordingly, the current invention provides, in part, efficiently-quenched fluorescent exo-glycosidase Glyco-BABS compounds that enable localization and quantification of enzyme activity in a live cell or tissue by, for example, imaging.

In some aspects, a compound according to the present invention may be useful for determining an exo-glycosidase's activity within a cell. By "determining" is meant analysing the effect of a test compound on a system, such as a cell or tissue. The analysing may be performed, without limitation, using imaging techniques or any other methods described herein or known to those skilled in the art. For example, a test cell may be contacted with a compound according to the present invention (e.g., a fluorescence-quenched exo-glycosidase Glyco-BABS) under conditions suitable for hydrolytic cleavage of the fluorescence-quenched exo-glycosidase substrate by an exo-glycosidase. The intensity of the fluorescence emission (the "fluorescence intensity") of the test cell may be determined using standard techniques. The fluorescence intensity of the test cell may be compared to that of a control cell (e.g., a cell that has not been exposed to, or contacted with, a compound according to the present invention) to determine background or non-specific fluorescence. The difference between the fluorescence intensity of the test cell and that of the control cell may be an indicator of exo-glycosidase activity, where an increase in fluorescence intensity in the test cell when compared to the control cell indicates exo-glycosidase activity.

In some embodiments, an exo-glycosidase's activity may be determined at different time points e.g., to monitor an exo-glycosidase's activity. For example, the exo-glycosidase activity of a test cell may be determined at a time point from 1 min-60 min, 1 h-5 h, 1 h-12 h, 1 h-24 h, 24 h-48 h, or any specific time within any of these ranges, such as 1 min, 2 min, 3 min, 4 min, 5 min, 10 min, 15 min, 20 min, 25 min, 30 min, 35 min, 40 min, 45 min, 50 min, 55 min, 60 min, 70 min, 80 min, 90 min, 100 min, 110 min, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, or 48 h.

In some aspects, a compound according to the present invention may be useful for determining the location of an exo-glycosidase activity within a cell, such as within the ER, Golgi, cytosol, nucleus, mitochondria or lysosomal compartments. For example, a test cell may be contacted with a compound according to the present invention (e.g., a fluorescence-quenched exo-glycosidase Glyco-BABS) under conditions suitable for hydrolytic cleavage of the fluorescence-quenched exo-glycosidase substrate by an exo-glycosidase. The fluorescence intensity of the test cell may be visualized using standard techniques, such as fluorescence imaging techniques. The fluorescence intensity of the test cell may be compared to that of a control cell (e.g., a cell that has not been exposed to, or contacted with, a compound according to the present invention) to determine background or non-specific fluorescence. The difference between localization of the fluorescence intensity of the test cell and that of the control cell may be an indicator of an exo-glycosidase activity in different cell compartments, where an increase in fluorescence intensity in a particular compartment of the test cell when compared to the control cell indicates an exo-glycosidase activity in that cell compartment.

In some embodiments, such methods may further include determining the location of exo-glycosidase protein levels within a cell, such as within the ER, Golgi, cytosol, nucleus, mitochondria or lysosomal compartments. For example, the test cell and the control cell may be contacted with an antibody that specifically binds an exo-glycosidase (the "exo-glycosidase antibody") and visualized using standard techniques. The difference between localization of the exo-glycosidase antibody in the test cell and the control cell may be an indicator of an exo-glycosidase protein levels in different cell compartments.

In some aspects, a compound of the present invention may be useful for determining the effects of an exo-glycosidase modulator in a cell. For example, a test cell may be contacted with an exo-glycosidase modulator. The test cell and a control cell (e.g., a cell that has not been exposed to, or contacted with, the exo-glycosidase modulator) may be contacted with a compound according to the present invention (e.g., a fluorescence-quenched exo-glycosidase Glyco-BABS) under conditions suitable for hydrolytic cleavage of the fluorescence-quenched exo-glycosidase Glyco-BABS by an exo-glycosidase. The fluorescence intensity of the test cell and the control cell may be determined using standard techniques. The difference between the fluorescence intensity of the test cell and that of the control cell may be an indicator of the effect of an exo-glycosidase modulator on an exo-glycosidase activity, where a difference in fluorescence intensity of the test cell when compared to the control cell indicates an exo-glycosidase modulation.

An "exo-glycosidase modulator" may be any molecule that modulates the activity of an exo-glycosidase. By "modulate," "modulation" or "modulating" means an increase or decrease by any value between about 10% and about 90%, or of any value between about 30% and about 60%, or over about 100%, or an increase or decrease by about 1-fold, 2-fold, 5-fold, 10-fold or more, in comparison to a reference sample or compound, or in comparison to a wild type exo-glycosidase. An "exo-glycosidase modulator" may be an "exo-glycosidase inhibitor" or an "exo-glycosidase activator" or an "exo-glycosidase chaperone" or an "exo-glycosidase activity enhancer."

An "exo-glycosidase inhibitor" may be any molecule that inhibits the activity of an exo-glycosidase, for example, the ability to inhibit the hydrolytic cleavage of an exo-glycosidase nature or synthetic substrates, such as, for example for GBA1 enzyme, glucosylceramide or 4-methylumbelliferone-β-D glucopyranoside. By "inhibit," "inhibition" or "inhibiting" means a decrease by any value between about 10% and about 90%, or of any value between about 30% and about 60%, or over about 100%, or a decrease by about 1-fold, 2-fold, 5-fold, 10-fold or more, in comparison to a reference sample or compound, or in comparison to a wild type exo-glycosidase. It is to be understood that the inhibiting does not require full inhibition. In some embodiments, the inhibition may be transient. Examples of representative GBA1 exo-glycosidase inhibitors include: (3R,4R,5R)-5-(hydroxymethyl)piperidine-3,4-diol (isofagomine), and (3R, 4R,5S)-5-(difluoromethyl)piperidine-3,4-diol (AT3375). Examples of representative 0-GlcNAcase exo-glycosidase inhibitors include (3aR,5R,6S,7R,7aR)-2-(ethylamino)-3a, 6,7,7a-tetrahydro-5-(hydroxymethyl)-5H-Pyrano[3,2-d]thiazole-6,7-diol (Thiamet-G). For a discussion of inhibitors of exo-glycosidases such as GBA1 or OGA, see for example, Trapero et al.[34] or Gloster et al.[35]

An "exo-glycosidase activator" may be a small molecule that enhances the enzymatic activity of an exo-glycosidase by specifically binding to an allosteric site, a natural ligand binding site, or another site on an exo-glycosidase. By "enhance," "enhancement" or "enhancing" means an increase by any value between about 10% and about 90%, or of any value between about 30% and about 60%, or over about 100%, or an increase by about 1-fold, 2-fold, 5-fold, 10-fold or more, in comparison to a reference sample or compound, or in comparison to a wild type exo-glycosidase. For a discussion of exo-glycosidase activators, for example GBA1 activators, see Patnaik et al.[36]

An "exo-glycosidase chaperone" may be a molecule that acts as a pharmacological chaperone for an exo-glycosidase. A pharmacological chaperone, as used herein, is a small molecule that may be useful to increase enzyme levels in a cell or cellular compartment, as in for example pharmacological chaperone therapy or "PCT".[37,38] In PCT, a small molecule binds to an enzyme, such as an exo-glycosidase, in the endoplasmic reticulum (ER) or Golgi apparatus (Golgi) and enhances the ability of the enzyme to reach, and/or maintain, its proper fold. Compounds that are pharmacological chaperones may be active-site inhibitors, but may also bind to other sites on the enzyme such as allosteric sites, natural ligand binding sites, or other sites. Without being bound to any particular hypothesis, binding of the chaperone to the enzyme may enhance its trafficking through the secretory pathway to its proper cellular destination, to allow the enzyme to carry out its normal functions.

An "exo-glycosidase activity enhancer" may be a compound that increases an exo-glycosidase activity within cells. An exo-glycosidase activity enhancer may be an exo-glycosidase chaperone. An exo-glycosidase activity enhancer may be an exo-glycosidase activator. An exo-glycosidase activity enhancer may increase an exo-glycosidase activity within cells through a mechanism that is distinct from an exo-glycosidase chaperone or an exo-glycosidase activator.

In some aspects, a compound of the present invention may be useful for determining the efficacy of an exo-glycosidase-directed therapy. For example, a test cell, such as a cell obtained from a subject treated with or exposed to an exo-glycosidase-directed therapy, and a control cell (e.g., a cell from a subject not treated with or exposed to the exo-glycosidase-directed therapy) may be contacted with a compound according to the present invention (e.g., a fluorescence-quenched exo-glycosidase Glyco-BABS) under conditions suitable for hydrolytic cleavage of the fluorescence-quenched exo-glycosidase substrate by an exo-glycosidase. The fluorescence intensity of the test cell and the control cell may be determined using standard techniques. The difference between the fluorescence intensity of the test cell and that of the control cell may be an indicator of the efficacy of the exo-glycosidase-directed therapy. An "exo-glycosidase-directed therapy" may be, without limitation, one or more of: an exo-glycosidase enzyme replacement therapy (ERT),[6] an exo-glycosidase chaperone therapy, an exo-glycosidase activator therapy, or an exo-glycosidase activity enhancer therapy.

In some embodiments, a compound of the present invention may be useful for determining the efficacy of a preclinical exo-glycosidase-directed therapy. In alternative embodiments, a compound of the present invention may be useful for determining the efficacy of a clinical exo-glycosidase-directed therapy. In alternative embodiments, a compound of the present invention may be useful for determining the efficacy of an experimental exo-glycosidase-directed therapy. In some embodiments, the cells may be derived from a subject treated with an exo-glycosidase-directed therapy. In some embodiments, the cells may be from tissue derived from a subject treated with an exo-glycosidase-directed therapy. In some embodiments, the subject may be a human subject. In some embodiments, the subject may be a non-human subject. In some embodiments, the cells may be derived from a human subject treated with an exo-glycosidase-directed therapy. In some embodiments, the cells may be fibroblasts or PBMCs. In some embodiments, the tissue may be derived from a human subject treated with an exo-glycosidase-directed therapy. In some embodiments, the tissue may be a skin punch derived from a human subject treated with an exo-glycosidase-directed therapy.

In some aspects, a compound of the present invention may be useful for screening for an exo-glycosidase activity enhancer in for example a cell-based library screen. For example, a test cell may be contacted with a test compound, from, for example a compound library. The test cell and a control cell (e.g., a cell that has not been exposed to, or contacted with, a compound from the compound library) may be contacted with a compound according to the present invention (e.g., a fluorescence-quenched exo-glycosidase Glyco-BABS) under conditions suitable for hydrolytic cleavage of the fluorescence-quenched exo-glycosidase Glyco-BABS by an exo-glycosidase. The intensity of the fluorescence emission (the "fluorescence intensity") of the test cell and the control cell may be determined using standard techniques. The difference between the fluorescence intensity of the test cell and that of the control cell may determine whether the test compound is an exo-glycosidase activity enhancer, where an increase in fluorescence intensity in the test cell when compared to the control cell indicates that the test compound is an exo-glycosidase activity enhancer. In alternative embodiments, the cell-based library screen may be a high-throughput screen. In alternative embodiments, the cell-based library screen may be a phenotypic screen.

Any suitable cell (e.g., test cell and/or control cell) may be used in the methods according to the invention. In some embodiments, the cell may be a eukaryotic cell. In some embodiments, the cell may be a mammalian cell. In some embodiments, the cell may be a non-human cell. In some embodiments, the cell may be a human cell. In some embodiments, the cell may be an immortalized cell. In some embodiments, the cell may be a stem cell. In some embodiments, the cell may be a pluripotent stem cell. In some embodiments, the cell may be a transfected cell. In some embodiments, the cell may be an inducible transfected cell. In some embodiments, the cell may be an inducible transfected stem cell. In some embodiments, the cells may be cultured. In some embodiments, the cells may be a primary cell. In some embodiments, the cell may be derived from one of more of: primary cells, cultured cells, stem cells, pluripotent stem cells, transfected cells, inducible transfected cells, inducible transfected stem cells, human cells, non-human cells, and immortalized cells. In some embodiments, the cell may be non-human blood cells. In some embodiments, the cell may be a human blood cell. In some embodiments, the cell may be a live cell. In some embodiments, the cell may be an actively growing cell. In some embodiments, the cell may be a quiescent cell. In some embodiments, the cell may be at any phase of the cell cycle. In some embodiments, one or more of the compounds according to the present invention may be useful for monitoring an exo-glycosidase activity within a cell lysate. Examples of suitable cells include, for example: fibroblasts (e.g., human fibroblasts or non-human fibroblasts), peripheral blood mononuclear cells (PBMCs), such as human or non-human PBMCs, SK-N-SH cells, SK-SY5Y cells, SH-SY5Y cells, CHO cells, HEK cells, PC12 cells, glial cells, astrocytes, neuronal cells, or LUHMES cells, human induced pluripotent stem cells (iPSCs), human neural progenitor cells (NPCs), or human iPSC-derived dopaminergic neurons. In some embodiments, the cells may be derived from a subject treated with an exo-glycosidase-directed therapy.

In some embodiments, one or more of the compounds according to the present invention may be useful for monitoring an exo-glycosidase activity within a tissue. In some embodiments, the tissue may be mammalian tissue. In some embodiments, the tissue may be non-human tissue. In some embodiments, the tissue may be human tissue. In some embodiments, the tissue may be human biopsy tissue. In some embodiments, the tissue may be an organoid. Examples of suitable tissue include, for example: skin punch tissue, brain tissue, human organoid tissue, human cerebral organoid tissue, liver tissue, spleen tissue, kidney tissue, or any other biopsy tissue sample. In some embodiments, the cells may be from tissue derived from a subject treated with an exo-glycosidase-directed therapy. In some embodiments, the tissue may be derived from a human subject treated with an exo-glycosidase-directed therapy. In some embodiments, the tissue may be a skin punch derived from a human subject treated with an exo-glycosidase-directed therapy. In some embodiments, the cell or tissue may be provided in a sample. A "sample" can be any organ, tissue, cell, or cell extract isolated from a subject, such as a sample isolated from an animal, such as a mammal having a condition that is modulated by an exo-glycosidase. For example, a sample can include, without limitation, cells or tissue (e.g., from a biopsy or autopsy) from bone, brain, breast, colon, muscle, nerve, ovary, prostate, retina, skin, skeletal muscle, intestine, testes, heart, liver, lung, kidney, stomach, pancreas, uterus, adrenal gland, tonsil, spleen, soft tissue, peripheral blood, whole blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, urine, stool, saliva, placental extracts, amniotic fluid, a cryoprecipitate, a cryosupernatant, a cell lysate, mammalian cell culture or culture medium, products of fermentation, ascitic fluid, proteins present in blood cells, or any other specimen, or any extract thereof, obtained from a patient (human or animal), test subject, or experimental animal. A sample may also include, without limitation, products produced in cell culture by normal or transformed cells (e.g., via recombinant DNA or monoclonal antibody technology). A sample may also include, without limitation, any organ, tissue, cell, or cell extract isolated from a non-mammalian subject, such as an insect or a worm. A "sample" may also be a cell or cell line created under experimental conditions, that is not directly isolated from a subject. A sample can also be cell-free, artificially derived or synthesised. A "control" may include a sample obtained for use in determining base-line expression or activity. A control may also include a previously established standard. Accordingly, any test or assay conducted according to the invention may be compared with the established standard and it may not be necessary to obtain a control sample for comparison each time. As used herein, a subject may be a human, non-human primate, rat, mouse, cow, horse, pig, sheep, goat, dog, cat, etc. The subject may be a clinical patient, a clinical trial volunteer, an experimental animal, etc. The subject may be suspected of having or at risk for having a condition that is modulated by an exo-glycosidase, be diagnosed with a condition that is modulated by an exo-glycosidase, or be a control subject that is confirmed to not have a condition that is modulated by an exo-glycosidase. Diagnostic methods for conditions modulated by an exo-glycosidase, and the clinical delineation of such diagnoses, are known to those of ordinary skill in the art.

Suitable techniques to measure fluorescence intensity include, for example, fluorescence microscopy, confocal microscopy, use of a fluorescent plate reader, high content imaging, photoacoustic imaging, ratiometric imaging, flow cytometry, and fluorescence-activated cell sorting (FACS). Suitable techniques to measure fluorescence intensity with tissues include, for example, fluorescence microscopy, confocal microscopy, use of a fluorescent plate reader, high content imaging, photoacoustic imaging, and ratiometric imaging.

As will be appreciated by a person skilled in the art, the methods described herein for example for monitoring an exo-glycosidase activity within cells or tissue, or visualizing localization of an exo-glycosidase activity within cells, may also be represented, for example, as in Scheme J:

Scheme J

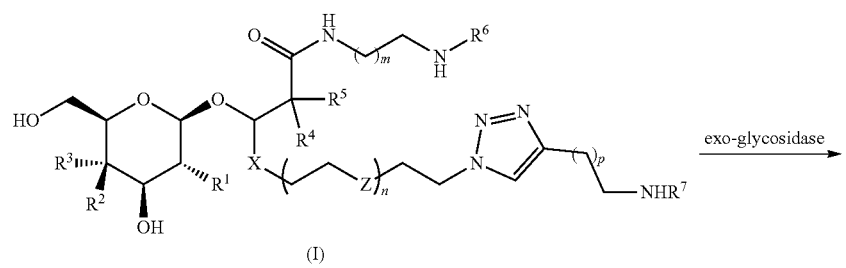

(I)

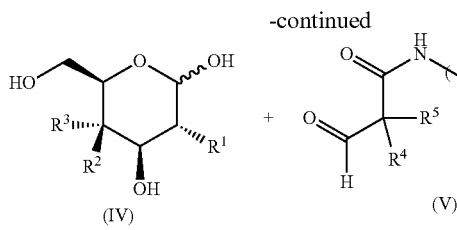

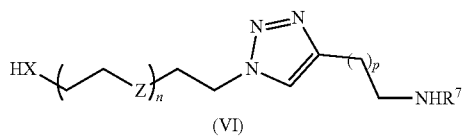

where X may be O or S; Z may be O or CH$_2$; R$^1$ may be OH or NHC(O)CH$_3$; R$^2$ may be OH and R$^3$ may be H, or R$^2$ may be H and R$^3$ may be OH; R$^4$ may be H or CH$_3$; R$^5$ may be H, OH, or halo; R$^6$ may be a suitable fluorophore and R$^7$ may be a suitable quencher, or R$^6$ may be a suitable quencher and R$^7$ may be a suitable fluorophore; m may be an integer from 1 to 5; n may be an integer from 0 to 2; and p may be an integer from 0 to 5. In this aspect, cells or tissue are treated with the fluorescence quenched substrate of Formula (I) (which is not fluorescent, due to internal quenching), and an exo-glycosidase enzyme hydrolytically cleaves the substrate of Formula (I) to generate the sugar of Formula (IV), the aldehyde of Formula (V), and the alcohol of Formula (VI). When R$^6$ is a suitable fluorophore, the compound of Formula (V) will be fluorescent, as the fluorophore R$^6$ is no longer internally quenched by the quencher R$^7$. When R$^7$ is a suitable fluorophore, the alcohol of Formula (VI) will be fluorescent, as the fluorophore R$^7$ is no longer internally quenched by the quencher R$^6$. Measuring the fluorescence intensity due to either the compound of Formula (V) or the compound of Formula (VI) thus provides a method for monitoring an exo-glycosidase activity within cells or tissue.

As will be appreciated by a person skilled in the art, the methods described herein for example for assessment of an exo-glycosidase inhibition in cells or tissue may also be represented, for example, as in Scheme K:

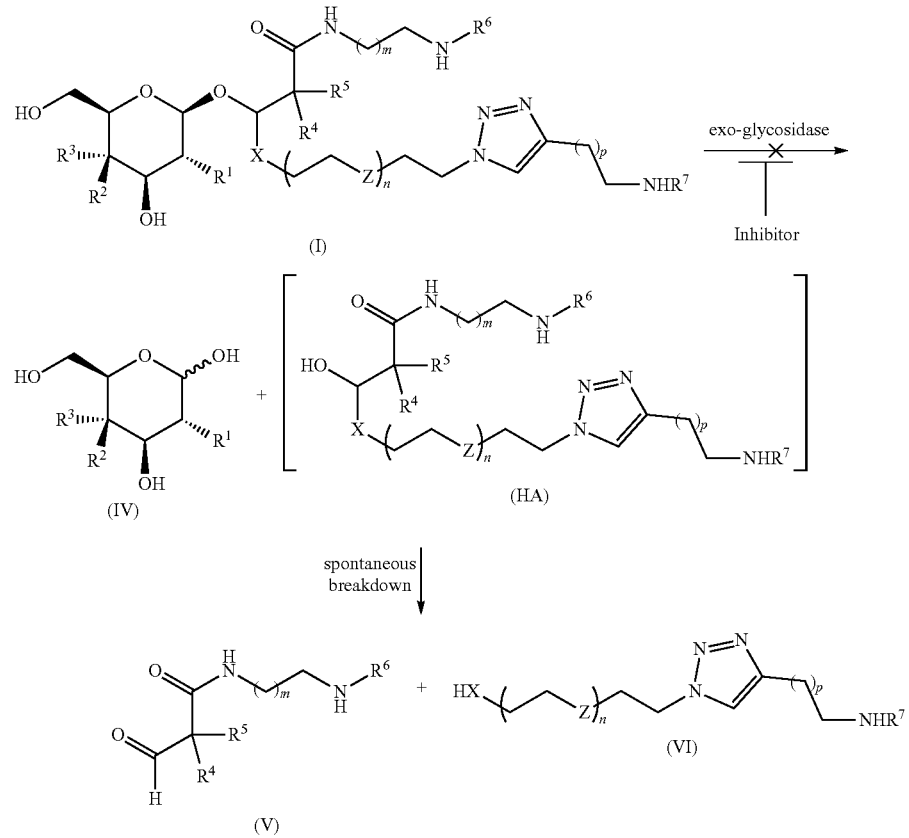

where X may be O or S; Z may be O or $CH_2$; $R^1$ may be OH or $NHC(O)CH_3$; $R^2$ may be OH and $R^3$ may be H, or $R^2$ may be H and $R^3$ may be OH; $R^4$ may be H or $CH_3$; $R^5$ may be H, OH, or halo; $R^6$ may be a suitable fluorophore and $R^7$ may be a suitable quencher, or $R^6$ may be a suitable quencher and $R^7$ may be a suitable fluorophore; m may be an integer from 1 to 5; n may be an integer from 0 to 2; and p may be an integer from 0 to 5. In this aspect, cells or tissue are treated with an exo-glycosidase inhibitor and the fluorescence quenched Glyco-BABS of Formula (I), and the exo-glycosidase inhibitor prevents the exo-glycosidase enzyme from hydrolytically cleaving the substrate of Formula (I) to generate either the sugar of Formula (IV) or the hemiacetal intermediate (HA), thereby preventing the generation of aldehyde of Formula (V) and the alcohol of Formula (VI) through breakdown of intermediate (HA). Carrying out this procedure using, for example, varying concentrations of an exo-glycosidase inhibitor and measuring the fluorescence intensity due to either the compound of Formula (V) or the compound of Formula (VI) thus gives a measurement of the extent to which an exo-glycosidase enzyme is blocked by an exo-glycosidase inhibitor, and provides a method for assessment of an exo-glycosidase inhibition in cells or tissue.

A suitable concentration for use of a compound according to the invention, such as a compound of Formula (I), to monitor an exo-glycosidase activity within cells or tissue may be any concentration from 0.1 nM-0.1 M, 0.1 nM-0.05 M, 0.05 nM-15 µM, 0.01 nM-100 µM, or 1-500 µM, or any specific concentration within any of these ranges, such as 10 nM, 20 nM, 30 nM, 40 nM, 50 nM, 0.1 µM, 0.2 µM, 0.3 µM, 0.4 µM, 0.5 µM, 0.6 µM, 0.7 µM, 0.8 µM, 0.9 µM, 1 µM, 2 µM, 3 µM, 4 µM, 5 µM, 6 µM, 7 µM, 8 µM, 9 µM, 10 µM, 11 µM, 12 µM, 13 µM, 14 µM, 15 µM, 16 µM, 17 µM, 18 µM, 19 µM, 20 µM, 30 µM, 40 µM, 50 µM, 60 µM, 70 µM, 80 µM, 90 µM, 100 µM, 150 µM, 200 µM, 250 µM, 300 µM, 350 µM, 400 µM, 450 µM, or 500 µM.

A suitable incubation time for use of a compound according to the invention, such as a compound of Formula (I), to monitor an exo-glycosidase activity within cells or tissue may be any incubation time from 1 min-60 min, 1 h-5 h, 1 h-12 h, 1 h-24 h, 24 h-48 h, 1 day-2 days, 1 day-5 days, 1 day-7 days, 1 day-14 days, 1 day-28 days, or any specific time within any of these ranges, such as 5 min, 10 min, 15 min, 20 min, 25 min, 30 min, 60 min, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 1.5 days, 2 days, 2.5 days, 3 days, 3.5 days, 4 days, 4.5 days, 5 days, 6 days, 7 days, 8 days, 9 days, 10 days, 11 days, 12 days, 13 days, or 14 days.

As used herein the singular forms "a", "an", and "the" include plural referents unless the context clearly dictates otherwise. For example, "a compound" refers to one or more of such compounds, "a cell" refers to a plurality of cells, "an exo-glycosidase" refers to one or more of such enzymes, while "the enzyme" includes a particular enzyme as well as other family member equivalents thereof as known to those skilled in the art.

Various alternative embodiments and examples of the invention are described herein. These embodiments and examples are illustrative and should not be construed as limiting the scope of the invention.

Examples

The following examples are intended to illustrate embodiments of the invention and are not intended to be construed in a limiting manner.

Abbreviations

AT3375=(3R,4R,5S)-5-(difluoromethyl)piperidine-3,4-diol
BABS=Bis-Acetal-Based Substrate
BHQ®2-NHS=2,5-dioxopyrrolidin-1-yl 4-((4-((E)-(2,5-dimethoxy-4-((E)-(4-nitrophenyl)diazenyl)phenyl)diazenyl)phenyl)(methyl)amino)butanoate
BODIPY®-NHS=4,4-difluoro-5-(2-pyrrolyl)-4-bora-3a,4a-diaza-s-indacene-3-propionic acid, succinimidyl ester
CBE=conduritol B epoxide
DABCYL-NHS=4-((4-(dimethylamino)phenyl)azo)benzoic acid, succinimidyl ester
DAPI=4',6-diamidino-2-phenylindole
DCM=dichloromethane
DIPEA=diisopropylethylamine
DMEM=Dulbecco's Modified Eagle's medium
DMF=N,N-dimethylformamide
DMSO=dimethylsulfoxide
EDANS=5-((2-aminoethyl)amino)naphthalene-1-sulfonic acid
EDANS-azide=5-((2-azidoethyl)amino)naphthalene-1-sulfonic acid
EMEM=Eagle's Minimum Essential Medium
EtOAc=ethyl acetate
FBS=fetal bovine serum
Glyco-BABS=Glycoside Bis-Acetal-Based Substrate
HEPES=4-(2-hydroxyethyl)-1-piperazineethanesulfonic acid
MEM=minimum essential media
MeOH=methanol
4-MUGlc=4-methylumbelliferyl-beta-D-glucopyranoside
4-MU=4-methylumbelliferone
PBS=phosphate buffered saline
TAMRA=Carboxytetramethylrhodamine fluorophore
TFA=2,2,2-trifluoroacetic acid
THF=tetrahydrofuran
General Procedures and Conditions
General Information Chemical synthesis methods: Unless stated otherwise, chemical reactions were performed under an Argon atmosphere. Glassware was oven-dried or flame-dried under vacuum. Anhydrous solvents were used for reactions (either commercial or dried and distilled following standard procedures) and reagent grade solvents were used for workup and purification. Reactions were monitored using thin-layer chromatography (TLC) on pre-coated aluminum sheets (ALUGRAM Xtra SIL G/UV254, Macherey-Nagel). After elution, TLC plates were inspected under UV light and developed by treatment with sulfuric acid stain (10% $H_2SO_4$ in $EtOH/H_2O$), Hanessian's stain (Cerium Ammonium Molybdate), $KMnO_4$ stain or Orcinol stain. Silica gel column chromatography was performed under positive pressure using 230-400 Mesh silica (grade 60, Fischer Scientific). HPLC (Agilent 1100 series) was performed using Eclipse XDB-C18 columns (3.5 µm, 3.0×150 mm for analytical runs and 5.0 µm, 9.4×250 mm for semi-preparative scale purifications) using HPLC grade solvents. NMR spectra were recorded at 293 K, using either Bruker AVANCE III (400 or 500 MHz) or Bruker AVANCE II 600 MHz (TCI or QNP cryoprobes) spectrometers. Chemical shifts (ppm) were reported relative to deuterated solvents (Cambridge Isotope Laboratories Inc.) residual peaks. Abbreviations used to describe the observed peaks: s, singlet; d, doublet; t, triplet; q, quadruplet; m, multiplet and bs, broad singlet. Complete signal attribution was based on 1D and 2D NMR (COSY, HSQC and HMBC). High resolution mass spectra were recorded using a Bruker MicrOTOF or a Bruker maXis Impact spectrometer using positive or negative electrospray ionization (ESI). Percentage yields for chemical reactions are quoted only for those compounds that were purified by recrystallization or by column chromatography, and for which the purity was assessed verified by $^1$H NMR spectroscopy and/or HPLC. Chemicals and solvents were obtained from Sigma-Aldrich and used without further purification unless otherwise noted.

In Vitro Kinetic Assays

For some experiments, fluorescence kinetic assays were performed using a Varian Cary Eclipse Spectrophotometer set for 335/493 nm excitation/emission wavelengths. Slits were set at 10 nm and the detector was set on Medium voltage. Enzymatic reactions with human OGA were carried out in PBS at 37° C. and were started by addition of hOGA (WT, Full-length, expressed in *E. coli.* as previously described) in a total volume of 160 μL (Starna sub-micro Fluorometer cuvette). For measurements of rates using different concentrations of substrates, a hOGA concentration of 100 nM was used. For hOGA titration, 25 μM of Glyco-BABS were added to various concentration of hOGA. For interrupted assay, reaction was started by addition of hOGA (680 nM final) in solutions of GlcNAc-BABS in PBS. Fluorescence acquisition was paused after 1 minute and a solution of Thiamet-G in PBS (2 mM) was quickly added (final concentration of 100 μM) and data acquisition was immediately resumed. For hemiacetal breakdown rate measurements, data after Thiamet-G addition was extracted and fitted using Prism software. EDANS standard curve was established using endpoint fluorescence measurements of serial dilutions of EDANS in the relevant buffer using the same instrument parameters. Inner-Filter effect measurements were carried out in cuvette by measuring fluorescence of several concentrations of EDANS in presence of various concentrations of GlcNAc-BABS. Kinetics with Glc-BABS and GBA enzymes (GBA1 and GBA3 purchased from R&D Systems), kinetics with GALC (R&D systems) and Gal-BABS, pH stability, quenching efficiency, some inner-filter effect experiments and lysates experiments were carried out using a Molecular Devices SpectraMax i3x plate reader. Emission/Excitation wavelengths were set at 350 and 490 nm respectively for EDANS/DABCYL Glyco-BABS and at 565 and 610 nm respectively for TAMRA/BHQ2 Glyco-BABS. Fluorescence measurements were performed using Costar 96-well black plates or Nunc 384-well black plates after sample preparation in 96-well mixing plates. For GBA1, the continuous assay was performed in citrate buffer (50 mM, pH 5.5) in the presence of 0.1% Triton, 1 mg/mL BSA and 0.14% taurodeoxycholate at 25° C. For GBA2, the continuous assay was performed in McIlvaine buffer (pH 5.5) in the presence of 1% C10E6 detergent. For GBA3, the continuous assay was performed in Tris-HCl buffer (10 mM, pH 7.1, 100 mM NaCl). For GALC, the continuous assay was performed in citrate buffer (50 mM, pH 4.5, 125 mM NaCl) in the presence 0.5% Triton.

For cell lysates experiments, SK-N-SH cells were cultured in EMEM media supplemented with 10% FBS and Penicillin/Streptomycin antibiotics. Cells were collected, washed with PBS and lyzed using ice-cold NP-40 lysis buffer (TRIS-HCl 50 mM pH 7.4, NP-40 1%, NaCl 150 mM). After centrifugation, the supernatant was diluted in PBS. The quantity of lysate used in each measurement well (384-well plate) was equivalent to 25000 cells. Various concentration of hOGA were added in the presence of inhibitor Thiamet-G (200 μM) or vehicle (DMSO). Reactions were started by adding the substrate at a final concentration of 20 μM. This experiment was carried out in quadruplicates and the rates were determined by establishing a standard curve for EDANS fluorescence in the SK-N-SH lysate.

Cell Culture

SK-N-SH cells were cultured, except where indicated otherwise, in EMEM supplemented with 10% FBS and 1% penicillin-streptomycin at 37° C. and 5% $CO_2$. The media was replaced every 3-4 days and the cells passaged after reaching 70-80% confluency, which occurred approximately every week. For imaging experiments, cells were seeded in triplicate into the central 60 wells of a sterile 96-well plate (Corning 4680) at a density of 10000 cells/well.

Live Cell Imaging

Fluorescence measurements in live cells was performed using a Molecular Devices ImageXpress XLS High-Content Imaging system (HCI). Live cells were plated in a 96-well or 384-well Corning plates. Cells were left to adhere and incubated at 37° C. in 5% $CO_2$ for at least 12 h in EMEM supplemented with 10% FBS and 1% penicillin-streptomycin before any treatment. Cells were then washed with warm (37° C.) EMEM (with no phenol red and FBS). A mixture of vehicle, substrate dissolved in DMSO (0.1% final concentration of DMSO), or substrate and inhibitor mixture, were added to the imaging media (EMEM with no phenol red or FBS supplemented with DAPI) which was then added to these cells and incubated at 37° C. and 5% $CO_2$ in the dark for the times specified (typically 2 h). After that incubation cells can be washed using Life Cell Imaging Media (Life Technologies) supplemented with 1 g/L glucose. The plate was then imaged in the Molecular Devices High-Content Imaging microscope, using a 40× objective. For each well, 9 sites were imaged at predefined regions of each well and 2 to 3 channel were recorded (DAPI, FITC, TRITC). The data was analyzed using the MetaXpress software suite. by determining the Mean Integrated Intensity obtained using the TRITC channel and dividing by the number of cells (determined thanks to DAPI staining).

Examples

Example 1

GlcNAc-Br-BABS(EDANS/DABCYL): 5-((2-((2R,3R)-3-(((2S,3R,4R,5S,6R)-3-acetamido-4,5-dihydroxy-6-(hydroxymethyl)tetrahydro-2H-pyran-2-yl)oxy)-2-bromo-3-(2-(2-(4-((4-((E)-(4-(dimethylamino)phenyl)diazenyl)benzamido)methyl)-1H-1,2,3-triazol-1-yl)ethoxy)ethoxy)-2-methylpropanamido)ethyl)amino)naphthalene-1-sulfonic Acid

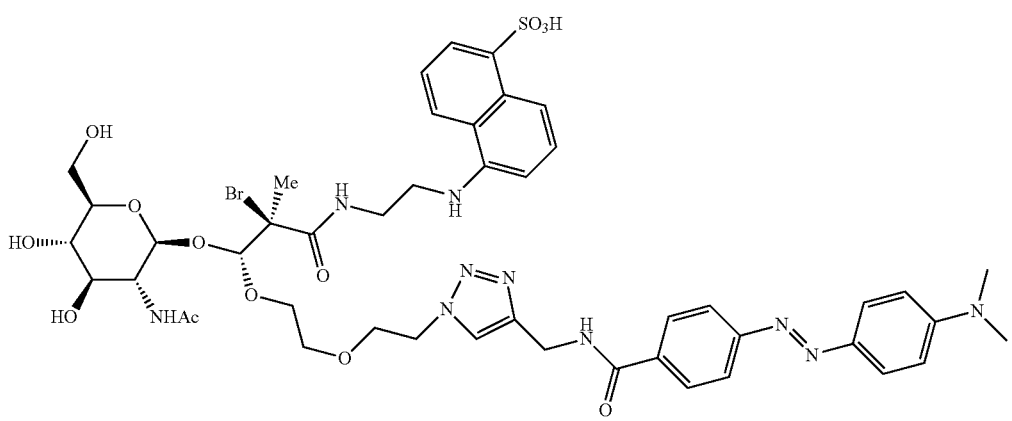

A 50 mL round-bottom flask containing (2R,3S,4R,5R,6R)-5-acetamido-2-(acetoxymethyl)-6-chlorotetrahydro-2H-pyran-3,4-diyl diacetate (1.63 g, 4.45 mmoles) was flushed with argon. Formic acid (15 mL) was added and the suspension was cooled to 0° C. using an ice bath. Under vigorous stirring, AgNO$_3$ (831 mg, 4.89 mmoles, 1.1 eq) powder was added in three portions over 5 mins. After 30 mins., the ice bath was removed and the mixture (white suspension) was stirred at r.t. for 45 mins. The crude mixture was then filtered through a plug of celite. The flask and filter were washed with CHCl$_3$ (250 mL). The filtrate was then slowly poured into 500 mL of saturated NaHCO$_3$. The organic layer was washed with saturated NaHCO$_3$ three times, then with brine. The organic layer was dried over Na$_2$SO$_4$ and concentrated to yield 1.136 g (66%) of (2R,3S,4R,5R,6S)-5-acetamido-2-(acetoxymethyl)-6-(formyloxy)tetrahydro-2H-pyran-3,4-diyl diacetate as a white foam. R$_f$=0.20 (DCM:EtOAc, 1:1). $^1$H NMR (500 MHz, CDCl$_3$) δ 8.07 (s, 1H, OC(O)H), 5.84 (d, J=8.7 Hz, 1H, H-1), 5.70 (d, J=9.3 Hz, 1H, AcNH), 5.21 (t, J=9.7 Hz, 1H, H-3), 5.14 (t, J=9.7 Hz, 1H, H-4), 4.33-4.24 (m, 2H, H-2, H-6a), 4.16-4.08 (m, 1H, H-6b), 3.85 (ddd, J=9.7 Hz, J=4.3 Hz, J=1.9 Hz, 1H, H-5), 2.09 (s, 3H, CH$_3$CO-6), 2.05 (s, 3H, CH$_3$CO-3), 2.04 (s, 3H, CH$_3$CO-4), 1.94 (s, 3H, CH$_3$CONHR). ppm. $^{13}$C NMR (125 MHz, CDCl$_3$) δ 171.3, 170.8, 170.4, 169.4, 92.1, 73.2, 72.4, 67.8, 61.7, 53.2, 23.3, 20.8, 20.75, 20.71 ppm. HR-ESI-MS calcd for C$_{15}$H$_{22}$NO$_{10}$ [M+H]$^+$ 376.1238, found 376.1239; calcd for C$_{15}$H$_{25}$N$_2$O$_{10}$ [M+NH$_4$]$^+$ 393.1504, found 393.1502; calcd for C$_{15}$H$_{21}$NNaO$_{10}$ [M+Na]$^+$ 398.1058, found 398.1063.

Preparation of Phosphorane Solution:

A 100 mL round-bottom flask containing methyl-2-bromo-propionate (4 g, 24 mmoles) was flushed with argon and 20 mL of anhydrous toluene were added. Under stirring at r.t., 5.9 mL of PBu$_3$ were added dropwise over 15 mins. The mixture was stirred overnight and then concentrated under vacuum to yield the phosphonium bromide salt. This salt can be stored at −20° C. for future use. The phosphorane was generated by dissolving 6.2 g of the phosphonium salt in 75 mL of DCM and vigorously washing this organic layer with a 10% solution of NaOH (100 mL). Drying (Na$_2$SO$_4$) and concentration yielded 5.40 g of the phosphorane which was kept under argon and dissolved in 32 mL of anhydrous toluene. Wittig reaction: A 100 mL round-bottom flask containing (2R,3S,4R,5R,6S)-5-acetamido-2-(acetoxymethyl)-6-(formyloxy)tetrahydro-2H-pyran-3,4-diyl diacetate (1.6 g, 4.26 mmoles) was flushed with argon. Anhydrous toluene (15 mL) was added followed by a freshly prepared solution of the phosphorane in toluene (13.6 mL, 0.5 M, 1.6 eq.). The mixture was then heated to 80° C. for 2 h before TLC showed complete conversion of the starting material. The crude mixture was then concentrated under vacuum. Silica gel column chromatography (Et$_2$O:EtOAc, 8:2) yielded 1.047 g of (2R,3S,4R,5R,6R)-5-acetamido-2-(acetoxymethyl)-6-(((E)-3-methoxy-2-methyl-3-oxoprop-1-en-1-yl)oxy)tetrahydro-2H-pyran-3,4-diyl diacetate and 511 mg of the Z-isomer (82% overall, E/Z: 2/1) as white foams. R$_f$=0.31 (DCM:EtOAc, 1:1). $^1$H NMR (400 MHz, CDCl$_3$) δ 7.41 (d, J=1.3 Hz, 1H, OCH=C$^{IV}$), 5.82 (d, J=8.7 Hz, 1H, AcNH), 5.33 (dd, J=10.4 Hz, J=9.4 Hz, 1H, H-3), 5.11 (t, J=9.4 Hz, 1H, H-4), 5.06 (d, J=8.3 Hz, 1H, H-1), 4.28 (dd, J=12.4 Hz, J=4.7 Hz, 1H, H-6a), 4.13 (dd, J=12.4 Hz, J=2.4 Hz, 1H, H-6b), 4.04 (dt, J=10.4 Hz, J=8.3 Hz, 1H, H-2), 3.82 (ddd, J=9.4 Hz, J=4.7 Hz, J=2.4 Hz, 1H, H-5), 3.70 (s, 3H, OCH$_3$), 2.08 (s, 3H, CH$_3$CO-6), 2.04 (s, 3H, CH$_3$CO-3), 2.03 (s, 3H, CH$_3$CO-4), 1.94 (s, 3H, CH$_3$CONHR), 1.73 (d, J=1.3 Hz, 3H, CH$_3$) ppm. $^{13}$C NMR (100 MHz, CDCl$_3$) δ 170.9, 170.8, 170.4, 169.4, 168.7, 153.3, 110.0, 101.0, 72.6, 71.7, 68.2, 61.9, 54.4, 51.6, 23.4, 20.84, 20.79, 20.7, 9.6 ppm. HR-ESI-MS calcd for C$_{19}$H$_{28}$NO$_{11}$ [M+H]+ 446.1657, found 446.1671; calcd for C$_{19}$H$_{31}$N$_2$O$_{11}$ [M+NH$_4$]$^+$ 463.1922, found 463.1934; calcd for C$_{19}$H$_{27}$NNaO$_{11}$ [M+Na]$^+$ 468.1476, found 468.1490; calcd for C$_{38}$H$_{54}$N$_2$NaO$_{22}$ [2M+Na]$^+$ 913.3060, found 913.3085.

A 5 mL round-bottom flask containing (2R,3S,4R,5R,6R)-5-acetamido-2-(acetoxymethyl)-6-(((E)-3-methoxy-2-methyl-3-oxoprop-1-en-1-yl)oxy)tetrahydro-2H-pyran-3,4-diyl diacetate (200 mg, 0.449 mmoles) and 2-(2-Azidoethoxy)ethanol (1.177 g, 8.98 mmoles, 20 eq.) was flushed with argon. Anhydrous DCM was added (500 μL) followed by N-bromosuccinimide (88 mg, 0.494 mmoles, 1.1 eq). The mixture was stirred at r.t., and, after 2 h, TLC (DCM:EtOAc, 7:3) showed complete conversion of the starting material. The crude mixture was concentrated and purified through silica gel column chromatography (Et$_2$O: EtOAc, 7:3). Because the product was still contaminated with the spacer, the pure product was obtained through precipitation using Et$_2$O:Hexanes to afford (2R,3S,4R,5R, 6S)-5-acetamido-2-(acetoxymethyl)-6-((1R,2R)-1-(2-(2-azidoethoxy)ethoxy)-2-bromo-3-methoxy-2-methyl-3-oxopropoxy)tetrahydro-2H-pyran-3,4-diyl diacetate (168 mg, 57%). R$_f$=0.16 (DCM:EtOAc, 7:3). $^1$H NMR (400 MHz, CDCl$_3$) δ 5.58 (d, J=9.3 Hz, 1H, AcNH), 5.18 (dd, J=10.6 Hz, J=9.6 Hz, 1H, H-3), 5.15 (s, 1H, OCH(OR)R), 5.07 (t, J=9.6 Hz, 1H, H-4), 4.81 (d, J=8.4 Hz, 1H, H-1), 4.25 (dd, J=12.2 Hz, J=2.4 Hz, 1H, H-6a), 4.22-4.10 (m, 2H, H-6b, H-2), 4.00 (dt, J=10.9 Hz, J=4.0 Hz, 1H, ½ OCH$_2$CH$_2$O), 3.79 (s, 3H, OCH$_3$), 3.74 (ddd, J=9.6 Hz, J=5.3 Hz, J=2.4 Hz, 1H, H-5), 3.70-3.63 (m, 1H, ½ OCH$_2$CH$_2$O), 3.61-3.52 (m, 4H, CH$_2$OCH$_2$), 3.33 (td, J=4.7 Hz, J=1.1 Hz, 2H, CH$_2$N$_3$), 2.06 (s, 3H, CH$_3$CO-6), 2.04 (s, 6H, CH$_3$CO-(3, 4)), 1.96 (s, 3H, CH$_3$CONHR), 1.83 (s, 3H, CH$_3$) ppm. $^{13}$C NMR (100 MHz, CDCl$_3$) δ 171.2, 170.6, 170.2, 169.44, 169.43, 105.1, 101.5, 72.5, 72.2, 70.2, 70.1, 69.2, 68.5, 62.2, 61.2, 54.1, 53.3, 50.9, 23.7, 20.82, 20.76, 19.7 ppm. HR-ESI-MS calcd for C$_{23}$H$_{36}$BrN$_4$O$_{13}$ [M+H]$^+$ 655.1457, found 655.1452; calcd for C$_{23}$H$_{39}$BrN$_5$O$_{13}$ [M+NH$_4$]$^+$ 672.1722, found 672.1730; calcd for C$_{23}$H$_{35}$BrN$_4$NaO$_{13}$ [M+Na]$^+$ 677.1276, found 677.1279; calcd for C$_{23}$H$_{35}$BrKN$_4$O$_{13}$ [M+K]$^+$ 693.1016, found 693.1014.

A 50 mL round-bottom flask containing (2R,3S,4R,5R, 6S)-5-acetamido-2-(acetoxymethyl)-6-((1R,2R)-1-(2-(2-azidoethoxy)ethoxy)-2-bromo-3-methoxy-2-methyl-3-oxopropoxy)tetrahydro-2H-pyran-3,4-diyl diacetate (96 mg, 0.146 mmoles) was flushed with argon. A mixture of THF and water (1:1) was added (10 mL). LiOH.H$_2$O was then added (61 mg, 10 eq.) in one portion and the mixture was stirred at r.t. overnight. The mixture was then diluted with methanol and the base was neutralized using Amberlite IR-120 (H$^+$-form) resin. After filtration and concentration under vacuum, the crude was dissolved under argon in 10 mL of pyridine. 4 mL of acetic anhydride were then added and the mixture was stirred at r.t. for 3 h. The mixture was then concentrated, co-evaporated with toluene 3 times and the crude residue was then re-dissolved in THF (40 mL) and water (5 mL) After 30 minutes of stirring, the mixture was concentrated and co-evaporated with toluene. The crude product was then purified using silica gel column chromatography (1: DCM, 2: DCM+5% methanol, 3: DCM+10% methanol) to afford (2R,3R)-3-(((2S,3R,4R,5S,6R)-3-acetamido-4,5-diacetoxy-6-(acetoxymethyl)tetrahydro-2H-pyran-2-yl)oxy)-3-(2-(2-azidoethoxy)ethoxy)-2-bromo-2-methylpropanoic acid (58 mg, 62%). R$_f$=0.18 (DCM: MeOH, 95:5). $^1$H NMR (500 MHz, MeOD) δ 5.31 (dd, J=10.5 Hz, J=9.5 Hz, 1H, H-3), 5.17 (s, 1H, OCH(OR)R), 4.99 (t, J=9.5 Hz, 1H, H-4), 4.95 (d, J=8.4 Hz, 1H, H-1), 4.30-4.14 (m, 2H, H-6a, H-6b), 4.11-4.03 (m, 1H, ½ OCH$_2$CH$_2$O), 3.98 (dd, J=10.5 Hz, J=8.5 Hz, 1H, H-2), 3.90 (ddd, J=10.1 Hz, J=4.8 Hz, J=2.6 Hz, 1H, H-5), 3.76-3.68 (m, 1H, ½ OCH$_2$CH$_2$O), 3.67-3.55 (m, 4H, CH$_2$OCH$_2$), 3.36-3.33 (m, 2H, CH$_2$N$_3$), 2.07 (s, 3H, CH$_3$CO-6), 2.02 (s, 3H, CH$_3$CO-4), 1.99 (s, 3H, CH$_3$CO-3), 1.93 (s, 3H, CH$_3$CONHR), 1.76 (s, 3H, CH$_3$) ppm. $^{13}$C NMR (125 MHz, MeOD) 173.6, 172.2, 171.8, 171.3, 107.3, 102.4, 73.7, 72.9, 71.1, 71.0, 70.5, 70.4, 63.3, 55.4, 51.8, 23.2, 20.9, 20.7, 20.60, 20.56 ppm. HR-ESI-MS calcd for C$_{22}$H$_{34}$BrN$_4$O$_{13}$ [M+H]$^+$ 641.1300, found 641.1302; calcd for C$_{22}$H$_{37}$BrN$_5$O$_{13}$ [M+NH$_4$]$^+$ 658.1566, found 658.1565; calcd for C$_{22}$H$_{33}$BrN$_4$NaO$_{13}$ [M+Na]$^+$ 663.1120, found 663.1112.

A 10 mL round-bottom flask containing (2R,3R)-3-(((2S, 3R,4R,5S,6R)-3-acetamido-4,5-diacetoxy-6-(acetoxymethyl)tetrahydro-2H-pyran-2-yl)oxy)-3-(2-(2-azidoethoxy)ethoxy)-2-bromo-2-methylpropanoic acid (17 mg, 0.026 mmoles) and EDANS-NH$_2$ (10 mg, 0.037 mmoles, 1.4 eq.) was flushed with argon. Anhydrous DMF (2 mL) was then added, followed by DIPEA (18 μL, 0.106 mmoles, 4 eq.) and HBTU (20 mg, 0.053 mmoles, 2 eq.). The mixture was then stirred at r.t. overnight. After concentration and co-evaporation with toluene, the crude mixture was filtered over a plug of silica gel (DCM then DCM:MeOH, 9:1). This intermediate (18 mg) was transferred into a 50 mL round-bottom flask containing DABCYL-Alkyne (7.4 mg, 0.024 mmoles, 1.2 eq.). After flushing with argon, 4 mL of anhydrous DCM were added followed by DIPEA (13 μL, 0.08 mmoles, 4 eq.) and Cu(MeCN)$_4$PF$_6$ (1.5 mg, 0.004 mmoles, 0.2 eq.). The mixture was stirred at r.t. overnight. After concentration, the crude mixture was diluted in methanol and neutralized using Amberlite IR-120 (Na$^+$-form) resin. Purification through silica gel column chromatography (DCM:MeOH, 9:1) provided 5-((2-((2R,3R)-3-(((2S, 3R,4R,5S,6R)-3-acetamido-4,5-diacetoxy-6-(acetoxymethyl)tetrahydro-2H-pyran-2-yl)oxy)-2-bromo-3-(2-(2-(4-((4-((E)-(4-(dimethylamino)phenyl)diazenyl)benzamido)methyl)-1H-1,2,3-triazol-1-yl)ethoxy)ethoxy)-2-methylpropanamido)ethyl)amino)naphthalene-1-sulfonic acid (20 mg, 64% over 2 steps). R$_f$=0.43 (DCM:MeOH, 85:15). $^1$H NMR (600 MHz, MeOD) δ 8.15 (d, J=8.6 Hz, 1H, CH-edans), 8.14-8.09 (m, 2H, CH-edans), 8.01-7.97 (m, 2H, CH-dabcyl), 7.89-7.82 (m, 4H, CH-dabcyl), 7.76 (bs, 1H, H-triaz), 7.38-7.33 (m, 2H, CH-edans), 6.86-6.81 (m, 2H, CH-dabcyl), 6.64 (d, J=7.7 Hz, 1H, CH-edans), 5.29 (dd, J=10.7 Hz, J=9.2 Hz, 1H, H-3), 5.11 (s, 1H, OCH(OR)), 4.96 (dd, J=10.2 Hz, J=9.2 Hz, 1H, H-4), 4.90-4.87* (m, 1H, H-1), 4.64-4.55 (m, 2H, CH$_2$NHC(O)-dabcyl), 4.26 (t, J=5.0 Hz, 2H, CH$_2$-Ntriaz), 4.14 (d, J=3.7 Hz, 2H, H-6), 4.01 (dd, J=10.7 Hz, J=8.4 Hz, 1H, H-2), 3.85-3.78 (m, 2H, H-5, ½ OCH$_2$CH$_2$O), 3.66-3.60 (m, 1H, ½ CH$_2$CH$_2$NH-edans), 3.56-3.52 (m, 1H, ½ CH$_2$CH$_2$NH-edans), 3.51-3.47 (m, 1H, ½ OCH$_2$CH$_2$O), 3.43 (t, J=5.1 Hz, 2H, CH$_2$CH$_2$N-triaz), 3.39 (t, J=5.8 Hz, 2H, CH$_2$CH$_2$NH-edans), 3.20-3.14 (m, 2H, OCH$_2$CH$_2$O), 3.11 (s, 6H, N(CH$_3$)$_2$), 1.98, 1.98, 1.93 (3s, 9H, 3×CH$_3$CO), 1.92 (s, 3H, CH$_3$CONHR), 1.81 (s, 3H, CH$_3$) ppm. $^{13}$C NMR (150 MHz, MeOD) δ 173.5, 172.1, 171.8, 171.3, 169.5, 156.6, 154.7, 145.4, 144.9, 141.8, 135.3, 131.5, 129.6, 128.7, 126.8, 126.5, 125.6, 125.5, 125.1, 123.7, 123.0, 116.3, 112.6, 107.0, 105.1, 102.2, 73.6, 72.8, 70.8, 70.3, 70.2, 70.0, 63.5, 63.1, 55.3, 51.2, 44.9, 40.4, 40.2, 36.2, 23.7, 21.7, 20.7, 20.6, 20.5 ppm. HR-ESI-MS calcd for C$_{52}$H$_{64}$BrN$_{10}$O$_{16}$S [M+H]$^+$ 1195.3400, found 1195.3388; calcd for C$_{52}$H$_{63}$BrN$_{10}$NaO$_{16}$S [M+Na]$^+$ 1217.3220, found 1217.3212; calcd for C$_{52}$H$_{65}$BrN$_{10}$O$_{16}$S [M+2H]$^{2+}$ 598.1736, found 598.1741; calcd for C$_{52}$H$_{63}$BrN$_{10}$Na$_2$O$_{16}$S [M+2Na]$^{2+}$ 620.1556, found 620.1560.

A 10 mL round-bottom flask containing 5-((2-((2R,3R)-3-(((2S,3R,4R,5S,6R)-3-acetamido-4,5-diacetoxy-6-(acetoxymethyl)tetrahydro-2H-pyran-2-yl)oxy)-2-bromo-3-(2-(2-(4-((4-((E)-(4-(dimethylamino)phenyl)diazenyl) benzamido)methyl)-1H-1,2,3-triazol-1-yl)ethoxy)ethoxy)-2-methylpropanamido)ethyl)amino)naphthalene-1-sulfonic acid (24 mg) was flushed with argon. Anhydrous methanol (2 mL) was then added. Sodium methoxide (ca. 5 mg) was added and the mixture was stirred at r.t. overnight. The crude was then concentrated and dissolved in water (6 mL). One fourth of this crude was purified thanks to semi-preparative scale HPLC (C-18, H$_2$O:MeCN, 15 to 55% MeCN gradient over 30 minutes, 2 mL·min$^{-1}$). Lyophilisation of the fractions containing the pure product provided 5-((2-((2R,3R)-3-(((2S,3R,4R,5S,6R)-3-acetamido-4,5-dihydroxy-6-(hydroxymethyl)tetrahydro-2H-pyran-2-yl)oxy)-2-bromo-3-(2-(2-(4-((4-((E)-(4-(dimethylamino)phenyl)diazenyl) benzamido)methyl)-1H-1,2,3-triazol-1-yl)ethoxy)-

2-methylpropanamido)ethyl)amino)naphthalene-1-sulfonic acid 1 (2.0 mg) as an orange fluffy powder. HPLC retention time=19.9 mins (C18 Semi-Prep, H$_2$O:MeCN, 90:10 to 45:55 over 30 minutes, 2 mL·min$^{-1}$)$^1$H NMR (600 MHz, MeOD) δ 8.20-8.10 (m, 3H, CH-edans), 8.03-7.96 (m, 2H, CH-dabcyl), 7.89-7.82 (m, 4H, CH-dabcyl), 7.77 (s, 1H, H-triaz), 7.41-7.33 (m, 2H, CH-edans), 6.87-6.80 (m, 2H, CH-dabcyl), 6.63 (d, J=7.8 Hz, 1H, CH-edans), 5.10 (s, 1H, OCH(OR)), 4.65 (s, 2H, CH$_2$NHC(O)-dabcyl), 4.62 (d, J=8.4 Hz, 1H, H-1), 4.25 (t, J=5.1 Hz, 2H, CH$_2$-Ntriaz), 3.91-3.88 (m, 1H, ½ OCH$_2$CH$_2$O), 3.88-3.84 (m, 1H, H-6a), 3.81 (dd, J=10.5 Hz, J=8.4 Hz, 1H, H-2), 3.65 (dd, J=11.8 Hz, J=5.4 Hz, 1H, H-6b), 3.63-3.59 (m, 1H, ½ CH$_2$CH$_2$NH-edans), 3.58-3.53 (m, 2H, ½ OCH$_2$CH$_2$O, ½ CH$_2$CH$_2$NH-edans), 3.50 (dd, J=10.5 Hz, J=8.0 Hz), 1H, H-3), 3.43 (t, J=4.9 Hz, 2H, CH$_2$CH$_2$N-triaz), 3.39 (t, J=5.9 Hz, 2H, CH$_2$CH$_2$NH-edans), 3.36-3.31 (m, 2H, H-4, H-5), 3.18-3.12 (m, 2H, OCH$_2$CH$_2$O), 3.11 (s, 6H, N(CH$_3$)$_2$), 1.97 (s, 3H, CH$_3$CONHR), 1.82 (s, 3H, CH$_3$) ppm. $^{13}$C NMR (150 MHz, MeOD) δ173.7, 172.2, 169.5, 156.5, 154.7, 146.1, 145.4, 144.9, 142.1, 135.5, 131.5, 129.5, 128.6, 126.7, 126.4, 125.6, 125.5, 125.0, 123.7, 123.0, 116.4, 112.6, 106.6, 105.0, 103.0, 78.1, 75.5, 72.1, 70.9, 70.0, 69.9, 63.7, 62.8, 57.1, 51.1, 44.7, 40.4, 40.1, 36.3, 23.4, 22.2 ppm. HR-ESI-MS calcd for C$_{46}$H$_{58}$BrN$_{10}$O$_{13}$S [M+H]$^+$ 1069.3083, found 1069.3063; calcd for C$_{46}$H$_{59}$BrN$_{10}$O$_{13}$S [M+2H]$^{2+}$ 535.1578, found 535.1576; calcd for C$_{46}$H$_{57}$BrN$_{10}$Na$_2$O$_{13}$S [M+2Na]$^{2+}$ 557.1397, found 557.1391.

Example 2

GlcNAc-OH-BABS(EDANS/DABCYL): 5-((2-((2R,3R)-3-(((2S,3R,4R,5S,6R)-3-acetamido-4,5-dihydroxy-6-(hydroxymethyl)tetrahydro-2H-pyran-2-yl)oxy)-3-(2-(2-(4-((4-((E)-(4-(dimethylamino)phenyl)diazenyl)benzamido)methyl)-1H-1,2,3-triazol-1-yl)ethoxy)ethoxy)-2-hydroxy-2-methylpropanamido)ethyl)amino)naphthalene-1-sulfonic Acid A 50 mL round-bottom flask containing (2R,3S,4R,5R,6R)-5-acetamido-2-(acetoxymethyl)-6-(((E)-3-methoxy-2-methyl-3-oxoprop-1-en-1-yl)oxy)tetrahydro-2H-pyran-3,4-diyl diacetate (357 mg, 0.801 mmoles) was flushed with argon. Anhydrous toluene and DCM (5+5 mL) were added and the mixture was cooled to 0° C. mCPBA was added in one portion (207 mg, 1.202 mmoles, 1.5 eq.) under stirring. The mixture was allowed to warm up to r.t. overnight. Completion of the reaction was monitored by running NMR on an aliquot of the crude mixture. The mixture was diluted in EtOAc and washed with Na$_2$S$_2$O$_3$ sat., NaHCO$_3$ sat., water and brine. The organic layer was dried (Na$_2$SO$_4$) and concentrated. Silica gel column chromatography (Hexanes:EtOAc, 3:7) provided (2R,3S,4R,5R,6S)-5-acetamido-2-(acetoxymethyl)-6-(((2S,3R)-3-(methoxycarbonyl)-3-methyloxiran-2-yl)oxy)tetrahydro-2H-pyran-3,4-diyl diacetate (248 mg, 67%) as a white foam. R$_f$=0.26 (Hex:EtOAc, 2:8). $^1$H NMR (500 MHz, CDCl$_3$) δ 5.67 (d, J=9.3 Hz, 1H, AcNH), 5.18 (t, J=10.0 Hz, 1H, H-3), 5.15 (s, 1H, OCH(O)C(CH$_3$)CO$_2$Me), 5.10 (t, J=9.6 Hz 1H, H-4), 4.86 (d, J=8.5 Hz, 1H, H-1), 4.26 (dd, J=12.4 Hz, J=4.6 Hz, 1H, H-6a), 4.20-4.04 (m, 2H, H-2, H-6b), 3.82-3.68 (m, 4H, H-5, CO$_2$CH$_3$), 2.09 (s, 3H, CH$_3$CO-6), 2.03 (s, 6H, CH$_3$CO-(3, 4)), 1.93 (s, 3H, CH$_3$CONHR), 1.53 (s, 3H, CH$_3$) ppm. $^{13}$C NMR (125 MHz, CDCl$_3$) δ 171.2, 170.8, 170.3, 169.40, 169.37, 99.3, 81.3, 72.5, 72.2, 68.2, 61.9, 59.1, 53.8, 53.1, 23.4, 20.9, 20.8, 20.7, 12.6 ppm. HR-ESI-MS calcd for C$_{19}$H$_{28}$N$_1$O$_{12}$ [M+H]$^+$ 462.1606, found 462.1602; calcd for C$_{19}$H$_{27}$N$_1$NaO$_{12}$ [M+Na]$^+$ 484.1425, found 484.1429; calcd for C$_{19}$H$_{27}$KN$_1$O$_{12}$ [M+K]$^+$ 500.1165, found 500.1147.

A 5 mL round-bottom flask containing (2R,3S,4R,5R,6S)-5-acetamido-2-(acetoxymethyl)-6-(((2S,3R)-3-(methoxycarbonyl)-3-methyloxiran-2-yl)oxy)tetrahydro-2H-pyran-3,4-diyl diacetate (210 mg, 0.455 mmoles) and 2-(2-Azidoethoxy)ethanol (1.192 g, 9.10 mmoles, 20 eq.) was flushed with argon. About 200 mg of flame-dried molecular sieves (4 Å) and anhydrous DCM were then added (2 mL). Camphorsulfonic acid (53 mg, 0.23 mmoles, 0.5 eq.) was then added. The mixture was stirred at r.t. for 3 h. The reaction was quenched using Et$_3$N (100 μL) and the mixture was filtered through a plug of celite (DCM). The crude mixture was concentrated and purified through silica gel column chromatography (Hexanes:EtOAc, 6:4 until all linker has been eluted then pure EtOAc) to afford (2R,3S,4R,5R,6S)-5-acetamido-2-(acetoxymethyl)-6-((1R,2R)-1-(2-(2-azidoethoxy)ethoxy)-2-hydroxy-3-methoxy-2-methyl-3-oxopropoxy)tetrahydro-2H-pyran-3,4-diyl

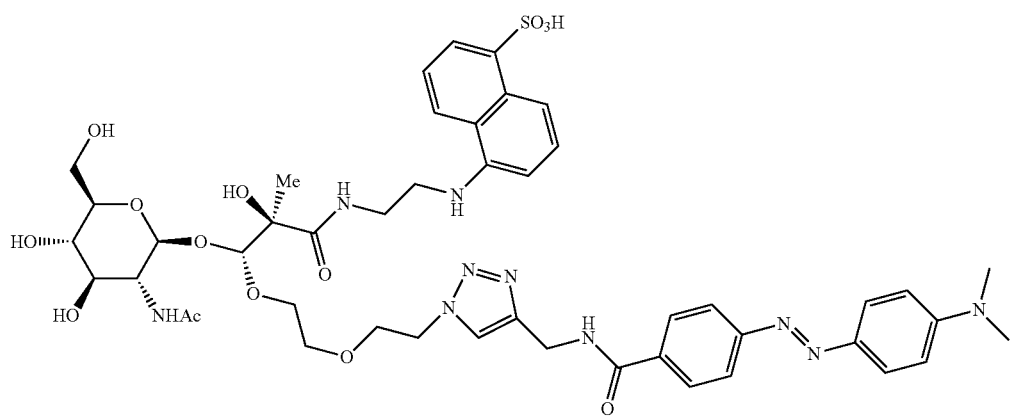

2 diacetate (178 mg, 66%). R$_f$=0.35 (EtOAc). $^1$H NMR (500 MHz, CDCl$_3$) δ 6.36 (d, J=9.2 Hz, 1H, AcNH), 5.14 (t, J=9.8 Hz, 1H, H-3), 5.04 (d, J=8.7 Hz, 1H, H-1), 4.97 (t, J=9.8 Hz, 1H, H-4), 4.87 (s, 1H, OCH(OR)R), 4.20-4.06 (m, 3H, H-6a, H-6b, H-2), 4.01-3.93 (m, 1H, ½ OCH$_2$CH$_2$O), 3.82-3.63 (m, 9H, OCH$_3$, H-5, ½ OCH$_2$CH$_2$O, CH$_2$OCH$_2$), 3.62-3.46 (m, 2H, CH$_2$N$_3$), 2.12 (s, 3H, CH$_3$CO-6), 2.02 (s, 3H, CH$_3$CO-4), 2.01 (s, 3H, CH$_3$CO-3), 1.93 (s, 3H, CH$_3$CONHR), 1.39 (s, 3H, CH$_3$) ppm. $^{13}$C NMR (125 MHz, CDCl$_3$) δ 173.8, 171.0, 170.8, 170.4, 169.6, 103.0, 94.8, 77.0, 73.4, 72.2, 70.8, 70.1, 69.8 (C-4), 68.5, 63.0, 54.0, 53.0, 50.8, 23.2, 21.2, 20.80, 20.77 ppm. HR-ESI-MS calcd for C$_{23}$H$_{37}$N$_4$O$_{14}$ [M+H]$^+$ 593.2301, found 593.2304; calcd for C$_{23}$H$_{40}$N$_5$O$_{14}$ [M+NH$_4$]$^+$ 610.2566, found 610.2572; calcd for C$_{23}$H$_{36}$N$_4$NaO$_{14}$ [M+Na]$^+$ 615.2120, found 615.2121.

A 50 mL round-bottom flask containing (2R,3S,4R,5R,6S)-5-acetamido-2-(acetoxymethyl)-6-((1R,2R)-1-(2-(2-azidoethoxy)ethoxy)-2-hydroxy-3-methoxy-2-methyl-3-oxopropoxy)tetrahydro-2H-pyran-3,4-diyl diacetate (27 mg, 0.045 mmoles) was flushed with argon. A mixture of THF and water (1:1) was added (5 mL). LiOH.H$_2$O was then added (19 mg, 10 eq.) in one portion and the mixture was stirred at r.t. overnight. The mixture was then diluted with methanol and the base was neutralized using Amberlite IR-120 (H$^+$-form) resin. After filtration and concentration under vacuum, the crude was dissolved under argon in 4 mL of pyridine. 1 mL of acetic anhydride was then added and the mixture was stirred at r.t. overnight. The mixture was then concentrated, co-evaporated with toluene 3 times and the crude residue was then re-dissolved in THF (5 mL) and water (2 mL). After 30 minutes of stirring, the mixture was concentrated and co-evaporated with toluene. The crude product was then purified using silica gel column chromatography (1: DCM, 2: DCM+5% methanol, 3: DCM+10% methanol) to afford (2R,3R)-3-(((2S,3R,4R,5S,6R)-3-acetamido-4,5-diacetoxy-6-(acetoxymethyl)tetrahydro-2H-pyran-2-yl)oxy)-2-acetoxy-3-(2-(2-azidoethoxy)ethoxy)-2-methylpropanoic acid (16 mg, 57%). R$_f$=0.15 (DCM:MeOH, 90:10). $^1$H NMR (500 MHz, MeOD) δ 5.42 (dd, J=10.4 Hz, J=9.3 Hz, 1H, H-3), 5.02-4.96 (m, 2H, H-4, H-1), 4.89 (s, 1H, OCH(OR)R), 4.25 (d, J=3.7 Hz, 2H, H-6a, H-6b), 4.00-3.94 (m, 1H, ½ OCH$_2$CH$_2$O), 3.88 (dt, J=10.1 Hz, J=3.7 Hz, 1H, H-5), 3.82 (dd, J=10.4 Hz, J=8.5 Hz, 1H, H-2), 3.73-3.67 (m, 1H, ½ OCH$_2$CH$_2$O), 3.67-3.58 (m, 4H, CH$_2$OCH$_2$), 3.39-3.34 (m, 2H, CH$_2$N$_3$), 2.10, 2.06, 2.02, 2.00 (4s, 12H, 4×CH$_3$CO), 1.90 (s, 3H, CH$_3$CONHR), 1.49 (s, 3H, CH$_3$) ppm. $^{13}$C NMR (125 MHz, CDCl$_3$) δ 174.1, 173.2, 172.2, 171.8, 171.36, 171.35, 105.5, 100.7, 84.9, 73.5, 72.9, 71.1, 71.0, 70.5, 69.8, 63.3, 55.9, 51.8, 23.0, 21.3, 20.7, 20.60, 20.57, 14.8 ppm. HR-ESI-MS calcd for C$_{24}$H$_{37}$N$_4$O$_{15}$ [M+H]$^+$ 621.2250, found 621.2243; calcd for C$_{24}$H$_{40}$N$_5$O$_{15}$ [M+NH$_4$]$^+$ 638.2515, found 638.2515; calcd for C$_{24}$H$_{36}$N$_4$NaO$_{15}$ [M+Na]$^+$ 643.2069, found 643.2068.

A 50 mL round-bottom flask containing (2R,3R)-3-(((2S,3R,4R,5S,6R)-3-acetamido-4,5-diacetoxy-6-(acetoxymethyl)tetrahydro-2H-pyran-2-yl)oxy)-2-acetoxy-3-(2-(2-azidoethoxy)ethoxy)-2-methylpropanoic acid (43 mg, 0.069 mmoles) and EDANS-NH$_2$ (26 mg, 0.097 mmoles, 1.4 eq.) was flushed with argon. Anhydrous DMF (2 mL) was then added, followed by DIPEA (46 µL, 0.276 mmoles, 4 eq.) and HBTU (31 mg, 0.083 mmoles, 1.2 eq.). The mixture was then stirred at r.t. overnight. After filtration through a plug of celite (DCM), the crude mixture was concentrated and co-evaporated with toluene. This crude mixture was then was transferred into a 50 mL round-bottom flask containing DABCYL-Alkyne (46 mg, 0.152 mmoles, 2.2 eq.). After flushing with argon, 5 mL of anhydrous DCM were added followed by DIPEA (46 µL, 0.276 mmoles, 4 eq.) and Cu(MeCN)$_4$PF$_6$ (10.2 mg, 0.028 mmoles, 0.4 eq.). The mixture was stirred at r.t. overnight. After concentration, the crude mixture was diluted in methanol and neutralized using Amberlite IR-120 (Na$^+$-form) resin. Purification through silica gel column chromatography (DCM then DCM:MeOH, 95:5 then DCM:MeOH, 90:10) provided the 5-((2-((2R,3R)-3-(((2S,3R,4R,5S,6R)-3-acetamido-4,5-diacetoxy-6-(acetoxymethyl)tetrahydro-2H-pyran-2-yl)oxy)-2-acetoxy-3-(2-(2-(4-((4-((E)-(4-(dimethylamino)phenyl)diazenyl)benzamido)methyl)-1H-1,2,3-triazol-1-yl)ethoxy)ethoxy)-2-methylpropanamido)ethyl)amino)naphthalene-1-sulfonic acid (66 mg, 81% over 2 steps). R$_f$=0.53 (DCM:MeOH, 90:10). $^1$H NMR (600 MHz, MeOD) δ 8.19 (d, J=8.6 Hz, 1H, CH-edans), 8.12 (dd, J=7.2 Hz, J=1.2 Hz, 1H, CH-edans), 8.08 (d, J=8.6 Hz, 1H, CH-edans), 8.03-7.98 (m, 2H, CH-dabcyl), 7.87-7.83 (m, 5H, H-triaz, CH-dabcyl), 7.38-7.33 (m, 2H, CH-edans), 6.85 (d, J=9.2 Hz, 2H, CH-dabcyl), 6.63 (d, J=7.6 Hz, 1H, CH-edans), 5.42 (dd, J=10.6 Hz, J=9.2 Hz, 1H, H-3), 4.94 (dd, J=10.2 Hz, J=9.2 Hz, 1H, H-4), 4.92 (d, J=8.4 Hz, 1H, H-1), 4.86 (s, 1H, OCH(OR)), 4.65 (bs, 2H, CH$_2$NHC(O)-dabcyl), 4.33 (bs, 2H, CH$_2$-Ntriaz), 4.16 (dd, J=12.3 Hz, J=4.9 Hz, 1H, H-6a), 4.12 (dd, J=12.3 Hz, J=2.6 Hz, 1H, H-6b), 3.85-3.78 (m, 2H, H-2, H-5), 3.78-3.74 (m, 1H, ½ OCH$_2$CH$_2$O), 3.63-3.55 (m, 1H, ½ CH$_2$CH$_2$NH-edans), 3.55-3.48 (m, 1H, ½ CH$_2$CH$_2$NH-edans), 3.50-3.44 (m, 2H, CH$_2$CH$_2$N-triaz), 3.43-3.38 (m, 1H, ½ OCH$_2$CH$_2$O), 3.38-3.33 (m, 2H, CH$_2$CH$_2$NH-edans), 3.25-3.17 (m, 2H, OCH$_2$CH$_2$O), 3.12 (s, 6H, N(CH$_3$)$_2$), 2.10 (s, 3H, CH$_3$CO), 1.99-1.98 (m, 6H, CH$_3$CO), 1.91 (s, 3H, CH$_3$CO), 1.90 (s, 3H, CH$_3$CONHR), 1.55 (s, 3H, CH$_3$) ppm. $^{13}$C NMR (150 MHz, MeOD) δ173.2, 172.9, 172.1, 171.8, 171.4, 171.3, 154.8, 145.3, 144.7, 142.2, 135.4, 131.5, 129.6, 128.6, 126.7, 125.6, 125.3, 123.7, 122.9, 116.7, 112.9, 105.3, 104.8, 100.7, 84.6, 73.5, 72.8, 70.6, 70.4, 70.0, 69.4, 63.0, 55.8, 51.3, 45.1, 40.5, 39.8, 36.3, 23.0, 21.4, 20.7, 20.6, 20.5, 14.5 ppm. HR-ESI-MS calcd for C$_{54}$H$_{67}$N$_{10}$O$_{18}$S [M+H]$^+$ 1175.4350, found 1175.4301; calcd for C$_{54}$H$_{66}$N$_{10}$NaO$_{18}$S [M+Na]$^+$ 1197.4169, found 1197.4120; calcd for C$_{54}$H$_{68}$N$_{10}$O$_{18}$S [M+2H]$^{2+}$ 588.2211, found 588.2223; calcd for C$_{54}$H$_{66}$N$_{10}$Na$_2$O$_{18}$S [M+2Na]$^{2+}$ 610.2031, found 610.2034.

A 10 mL round-bottom flask containing 5-((2-((2R,3R)-3-(((2S,3R,4R,5S,6R)-3-acetamido-4,5-diacetoxy-6-(acetoxymethyl)tetrahydro-2H-pyran-2-yl)oxy)-2-acetoxy-3-(2-(2-(4-((4-((E)-(4-(dimethylamino)phenyl)diazenyl)benzamido)methyl)-1H-1,2,3-triazol-1-yl)ethoxy)ethoxy)-2-methylpropanamido)ethyl)amino)naphthalene-1-sulfonic acid (20 mg) was flushed with argon. Anhydrous methanol (3 mL) was then added. Sodium methoxide (ca. 5 mg) was added and the mixture was stirred at r.t. overnight. The crude was then concentrated and dissolved in water (2 mL). This crude was purified thanks to semi-preparative scale HPLC (C-18, H$_2$O:MeCN, 15 to 55% MeCN gradient over 30 minutes, 2 mL·min$^{-1}$). Lyophilisation of the fractions containing the pure product provided 5-((2-((2R,3R)-3-(((2S,3R,4R,5S,6R)-3-acetamido-4,5-dihydroxy-6-(hydroxymethyl)tetrahydro-2H-pyran-2-yl)oxy)-3-(2-(2-(4-((4-((E)-(4-(dimethylamino)phenyl)diazenyl)benzamido)methyl)-1H-1,2,3-triazol-1-yl)ethoxy)ethoxy)-2-hydroxy-2-methylpropanamido)ethyl)amino)naphthalene-1-sulfonic acid 2 (12.9 mg) as an orange fluffy powder. HPLC retention time=18.5 mins (C18 Semi-Prep, H$_2$O:MeCN, 95:5 to 40:60 over 30 minutes, 2 mL·min$^{-1}$). $^1$H NMR (600 MHz, MeOD) δ 8.25-8.16 (m, 2H, CH-edans), 8.13 (dd, J=7.2 Hz, J=1.2 Hz, 1H, CH-edans), 8.03-7.95 (m, 2H, CH-dabcyl), 7.88 (s, 1H, H-triaz), 7.87-7.82 (m, 4H, CH-dabcyl), 7.42-7.34 (m, 2H, CH-edans), 6.85-6.80 (m, 2H, CH-dabcyl), 6.64 (d, J=7.7 Hz, 1H, CH-edans), 4.68 (s, 3H, OCH(OR), CH$_2$NHC(O)-dabcyl), 4.53 (d, J=8.4 Hz, 1H, H-1), 4.44-4.35 (m, 2H, CH$_2$-Ntriaz), 3.87-3.80 (m, 2H, ½ OCH$_2$CH$_2$O, H-6a), 3.74 (dd, J. 10.4 Hz, J. 8.4 Hz, 1H, H-2), 3.72-3.68 (m, 1H, ½ CH$_2$CH$_2$NH-edans), 3.64-3.56 (m, 4H, H-6b, ½ OCH$_2$CH$_2$O, CH$_2$CH$_2$N-triaz), 3.49-3.44 (m, 1H, ½ CH$_2$CH$_2$NH-edans), 3.44-3.41 (m, 1H, H-3), 3.39-3.32 (m, 4H, CH$_2$CH$_2$NH-edans, OCH$_2$CH$_2$O), 3.28-3.25 (m, 2H, H-5, H-4), 3.10 (s, 6H, N(CH$_3$)$_2$), 1.97 (s, 3H, CH$_3$CONHR), 1.26 (s, 3H, CH$_3$) ppm. $^{13}$C NMR (150 MHz, MeOD) δ176.7, 174.2, 169.5, 156.5, 154.7, 146.2, 145.5, 144.8, 142.1, 135.5, 131.5, 129.5, 128.5, 126.7, 126.4, 125.6, 125.5, 125.1, 123.7, 123.0, 116.5, 112.6, 107.1, 105.1, 102.0, 78.1, 77.8, 75.7, 72.1, 71.2, 70.2, 69.6, 62.8, 57.5, 51.2, 45.0, 40.4, 39.7, 36.3, 23.4, 22.1 ppm. HR-ESI-MS calcd for C$_{46}$H$_{59}$N$_{10}$O$_{14}$S [M+H]$^+$ 1007.3927. found 1007.3911; calcd for C$_{46}$H$_{58}$N$_{10}$NaO$_{14}$S [M+Na]$^+$ 1029.3747, found 1029.3724; calcd for C$_{46}$H$_{60}$N$_{10}$O$_{14}$S [M+2H]$^{2+}$ 504.2000, found 504.2001; calcd for C$_{46}$H$_{58}$N$_{10}$Na$_2$O$_{14}$S [M+2Na]$^{2+}$ 526.1819, found 526.1813.

Example 3

GlcNAc-OH-BABS(TAMRA/BHQ2): 5-((6-((2R,3R)-3-(((2S,3R,4R,5S,6R)-3-acetamido-4,5-dihydroxy-6-(hydroxymethyl)tetrahydro-2H-pyran-2-yl)oxy)-3-(2-(2-(4-((4-((E)-(2,5-dimethoxy-4-((E)-(4-nitrophenyl)diazenyl)phenyl)diazenyl)phenyl)(methyl)amino)butanamido)methyl)-1H-1,2,3-triazol-1-yl)ethoxy)ethoxy)-2-hydroxy-2-methylpropanamido)hexyl)carbamoyl)-2-(6-(dimethylamino)-3-(dimethyliminio)-3H-xanthen-9-yl)benzoate

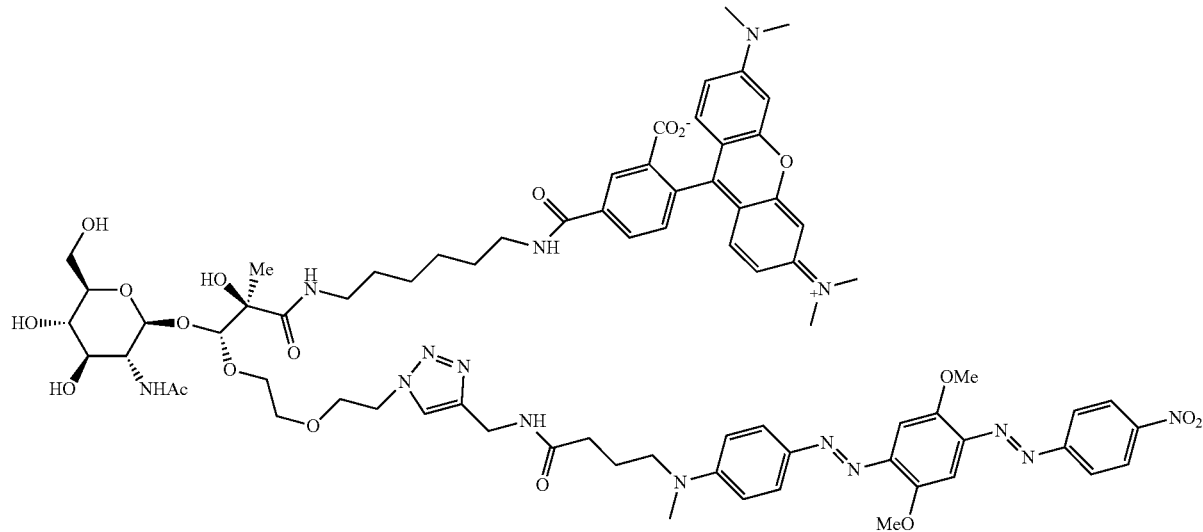

3

Compound 3 was synthesized according to procedures analogous to the synthesis of compound 2.

HR-ESI-MS calcd for C$_{75}$H$_{93}$N$_{15}$O$_{19}$ [M+2H]$^{2+}$ 753.8381, found 753.8376; calcd for C$_{75}$H$_{91}$N$_{15}$Na$_2$O$_{19}$ [M+2Na]$^{2+}$ 775.8200, found 775.8196.

Example 4

Gal-Br-BABS(EDANS/DABCYL): 5-((2-((2R,3R)-2-bromo-3-(2-(2-(4-((4-((E)-(4-(dimethylamino)phenyl)diazenyl)benzamido)methyl)-1H-1,2,3-triazol-1-yl)ethoxy)ethoxy)-2-methyl-3-(((2S,3R,4S,5R,6R)-3,4,5-trihydroxy-6-(hydroxymethyl)tetrahydro-2H-pyran-2-yl)oxy)propanamido)ethyl)amino)naphthalene-1-sulfonic Acid

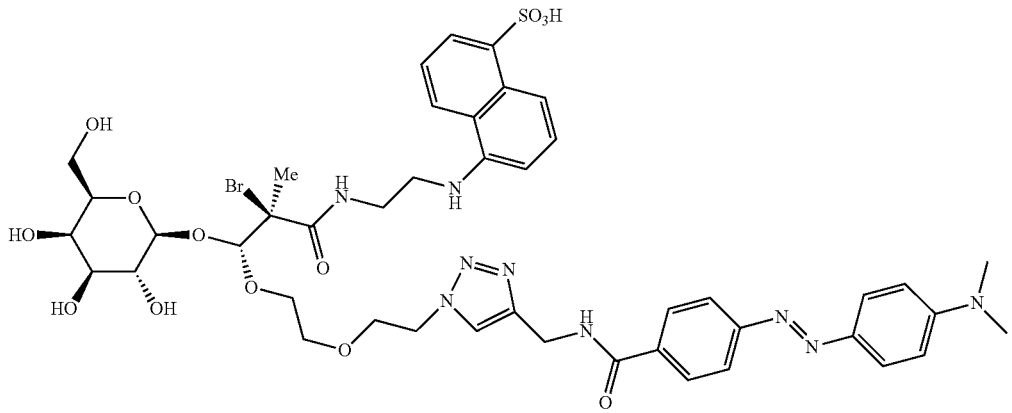

4

Compound 4 was synthesized according to procedures analogous to the synthesis of compound 1.

$^1$H NMR (600 MHz, MeOD) δ 8.17 (app d, J=8.6 Hz, 1H, CH-edans), 8.12 (app t, J=7.5 Hz, 2H, CH-edans), 7.99 (d, J=8.5 Hz, 2H, CH-dabcyl), 7.87-7.84 (m, 4H, CH-dabcyl, CH-dabcyl), 7.83 (s, 1H, H-triaz), 7.41 (app dd, J=8.4 Hz, J=7.3 Hz, 1H, CH-edans), 7.36 (app t, J=8.1 Hz, 1H, CH-edans), 6.83 (d, J=9.2 Hz, 2H, CH-dabcyl), 6.65 (app d, J=7.7 Hz, 1H, CH-edans), 4.97 (s, 1H, OCH(OR)), 4.65 (s, 2H, triaz-CH$_2$NHC(O)), 4.34 (d, J=7.8 Hz, 1H, H-1), 4.32 (t, J=5.0 Hz, 2H, OCH$_2$CH$_2$N-triaz), 3.96 (dt, J=9.3 Hz, J=4.4 Hz, 1H, ½ OCH$_2$CH$_2$O), 3.77 (d, J=3.2 Hz, 1H, H-4), 3.68-3.64 (m, 2H, H-6a, H-6b), 3.62-3.49 (m, 6H, H-2, ½ OCH$_2$CH$_2$O, OCH$_2$CH$_2$N-triaz, CH$_2$-12), 3.46-3.38 (m, 2H, CH$_2$-11), 3.36-3.33 (m, 2H, H-3, H-5), 3.30-3.26 (m, 2H, Acetal-OCH$_2$CH$_2$O), 3.10 (s, 6H, N(CH$_3$)$_2$), 1.88 (s, 3H, CH$_3$) ppm. $^{13}$C NMR (150 MHz, MeOD) δ172.3, 169.5, 156.5, 154.7, 146.1, 145.5, 144.8, 142.1, 135.4, 131.5, 129.5, 128.6, 126.8, 126.4, 125.6, 125.4, 125.1, 123.8, 123.0, 116.5, 112.6, 106.4, 105.2, 104.4, 76.9, 74.7, 72.6, 70.9, 70.15, 70.13, 70.07, 64.7, 62.4, 51.3, 44.7, 40.5, 40.4, 36.3, 24.1 ppm. HR-ESI-MS calcd for C$_{44}$H$_{55}$BrN$_9$O$_{13}$S [M+H]$^+$ 1028.2818, found 1028.2818; calcd for C$_{44}$H$_{54}$BrN$_9$NaO$_{13}$S [M+Na]$^+$ 1050.2637, found 1050.2645.

Example 5

Gal-OH-BABS(EDANS/DABCYL): 5-((2-((2R,3R)-3-(2-(2-(4-((4-((E)-(4-(dimethylamino)phenyl)diazenyl)benzamido)methyl)-1H-1,2,3-triazol-1-yl)ethoxy)ethoxy)-2-hydroxy-2-methyl-3-(((2S,3R,4S,5R,6R)-3,4,5-trihydroxy-6-(hydroxymethyl)tetrahydro-2H-pyran-2-yl)oxy)propanamido)ethyl)amino)naphthalene-1-sulfonic Acid

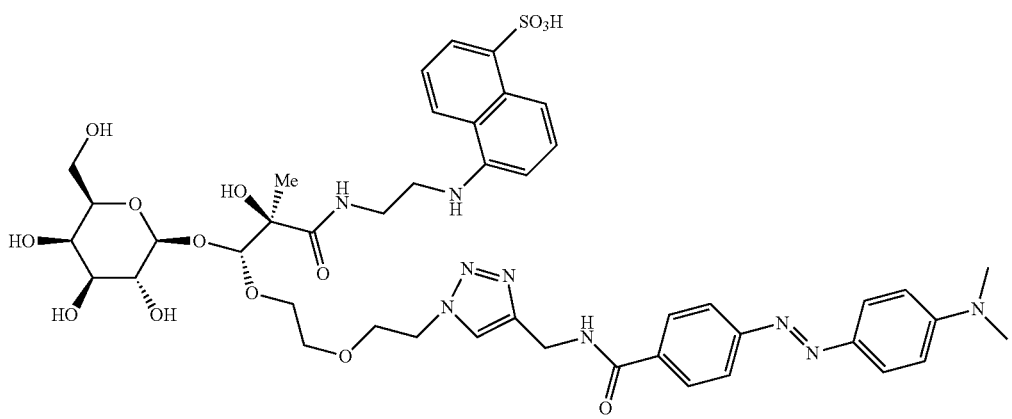

5

Compound 5 was synthesized according to procedures analogous to the synthesis of compound 2.

$^1$H NMR (600 MHz, MeOD) δ 8.17 (app d, J=8.6 Hz, 1H, CH-edans), 8.13 (app dd, J=7.5 Hz, J=5.5 Hz, 2H, CH-edans), 7.98 (d, J=8.7 Hz, 2H, CH-dabcyl), 7.96 (s, 1H, H-triaz), 7.90-7.73 (m, 4H, CH-dabcyl), 7.42-7.31 (m, 2H, CH-edans), 6.82 (d, J=9.3 Hz, 2H, CH-dabcyl), 6.63 (app d, J=7.7 Hz, 1H, CH-edans), 4.84*(bs, 1H, OCH(OR)), 4.72-4.63 (m, 2H, triaz-CH$_2$NHC(O)), 4.52-4.36 (m, 2H, OCH$_2$CH$_2$N-triaz), 4.20 (d, J=7.8 Hz, 1H, H-1), 3.90 (dt, J=11.6 Hz, J=4.5 Hz, 1H, ½ OCH$_2$CH$_2$O), 3.73 (t, J=5.0 Hz, 2H, OCH$_2$CH$_2$N-triaz), 3.69 (d, J=3.3 Hz, 1H, H-4), 3.67-3.60 (m, 2H, H-6a, H-6b, ½ OCH$_2$CH$_2$O, ½ CH$_2$-12), 3.57-3.52 (m, 1H, 1 CH$_2$-12), 3.51-3.46 (m, 3H, H-2, Acetal-OCH$_2$CH$_2$O), 3.39 (app t, J=5.7 Hz, 2H, CH$_2$-11), 3.22-3.14 (m, 2H, H-3, H-5), 3.10 (s, 6H, N(CH$_3$)$_2$), 1.31 (s, 3H, CH$_3$) ppm. $^{13}$C NMR (150 MHz, MeOD) δ 177.1, 169.6, 156.5, 154.7, 146.2, 145.5, 144.9, 142.1, 135.5, 131.4, 129.5, 128.6, 126.7, 126.4, 125.6, 125.4, 125.3, 123.8, 123.0, 116.4, 112.6, 105.9, 105.2, 103.5, 78.5, 76.7, 74.4, 72.6, 71.3, 70.17, 70.13, 69.9, 62.5, 51.4, 45.4, 40.4, 39.7, 36.3, 24.1 ppm. HR-ESI-MS calcd for C$_{44}$H$_{56}$N$_9$O$_{14}$S [M+H]$^+$ 966.3662, found 966.3661; calcd for C$_{44}$H$_{55}$N$_9$NaO$_{14}$S [M+Na]$^+$ 988.3481, found 988.3476.

Example 6

Glc-OH-BABS(EDANS/DABCYL): 5-((2-((2R,3R)-3-(2-(2-(4-((4-((E)-(4-(dimethylamino)phenyl)diazenyl)benzamido)methyl)-1H-1,2,3-triazol-1-yl)ethoxy)ethoxy)-2-hydroxy-2-methyl-3-(((2S,3R,4S,5S,6R)-3,4,5-trihydroxy-6-(hydroxymethyl)tetrahydro-2H-pyran-2-yl)oxy)propanamido)ethyl)amino)naphthalene-1-sulfonic Acid

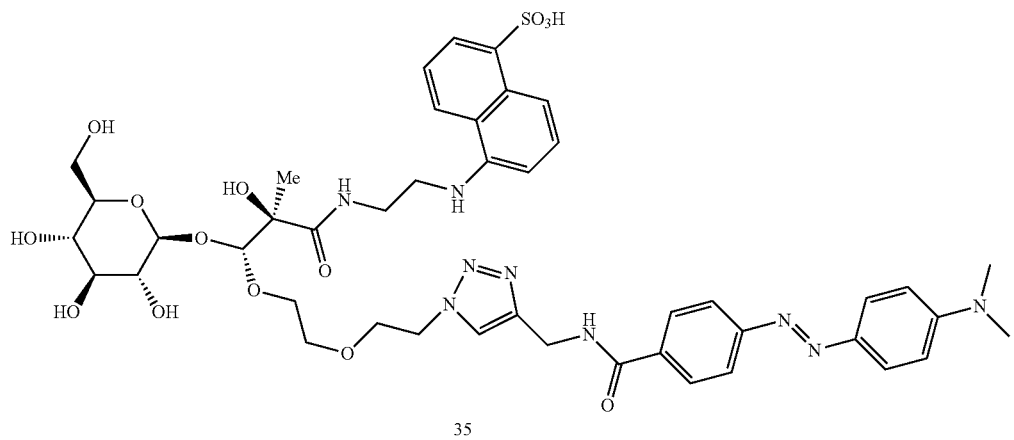

Compound 6 was synthesized according to procedures analogous to the synthesis of compound 2.

HR-ESI-MS calcd for C$_{44}$H$_{56}$N$_9$O$_{14}$S [M+H]$^+$ 966.3662, found 966.3644.

Example 7

Glc-H-BABS(EDANS/DABCYL): 5-((2-(3-(2-(2-(4-((4-((E)-(4-(dimethylamino)phenyl)diazenyl)benzamido)methyl)-1H-1,2,3-triazol-1-yl)ethoxy)ethoxy)-3-(((2S,3R,4S,5S,6R)-3,4,5-trihydroxy-6-(hydroxymethyl)tetrahydro-2H-pyran-2-yl)oxy)propanamido)ethyl)amino)naphthalene-1-sulfonic Acid

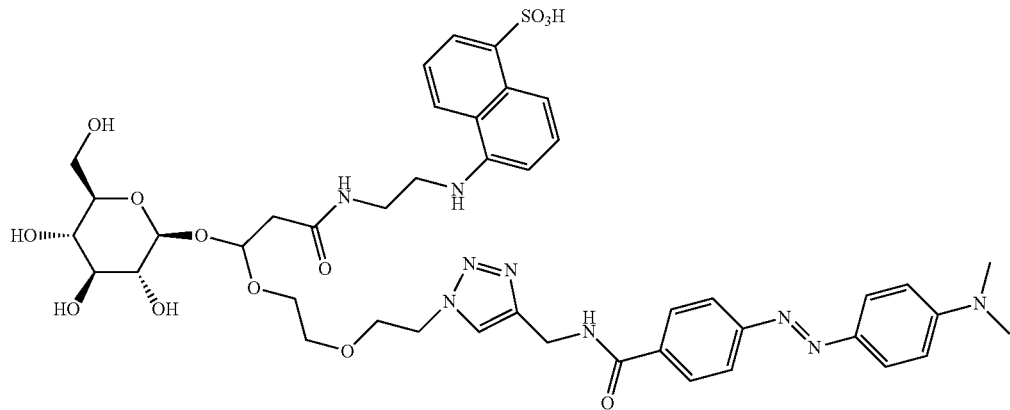

Preparation of Phosphorane Solution:

A 50 mL round-bottom flask containing ethyl 2-bromoacetate (500 µL, 4.5 mmoles) was flushed with argon and 5 mL of anhydrous toluene were added. Under stirring at r.t., 1.12 mL of PBu$_3$ were added dropwise over 15 mins. The mixture was stirred overnight and then concentrated under vacuum to yield the phosphonium bromide salt. The phosphorane was generated by dissolving 1.3 g of the phosphonium salt in 50 mL of DCM and vigorously washing this organic layer with a 10% solution of NaOH (75 mL). Drying (Na$_2$SO$_4$) and concentration yielded the phosphorane which was kept under argon and dissolved in 10 mL of anhydrous toluene. Wittig reaction: A 50 mL round-bottom flask containing (2R,3R,4S,5R,6S)-2-(acetoxymethyl)-6-(formyloxy)tetrahydro-2H-pyran-3,4,5-triyl triacetate (847 mg, 2.25 mmoles) was flushed with argon. Anhydrous toluene (5 mL) was added followed by a freshly prepared solution of the phosphorane in toluene (10 mL, 2 eq.). The mixture was then heated to 90° C. for 1.5 h before TLC showed complete conversion of the starting material. The crude mixture was then concentrated under vacuum. Silica gel column chromatography (Hexanes:EtOAc, 6:4) yielded 629 mg of the (2R,3R,4S,5R,6R)-2-(acetoxymethyl)-6-(((E)-3-ethoxy-3-oxoprop-1-en-1-yl)oxy)tetrahydro-2H-pyran-3,4,5-triyl triacetate (63%) as a white foam. R$_f$=0.22 (Hex:EtOAc, 6:4). $^1$H NMR (500 MHz, CDCl$_3$) δ 7.48 (d, J=12.4 Hz, 1H, OCH=CHCO$_2$Et), 5.47 (d, J=12.4 Hz, 1H, OCH=CHCO$_2$Et), 5.24 (t, J=9.4 Hz, 1H, H-3), 5.17-5.08 (m, 2H, H-2, H-4), 4.90 (d, J=7.8 Hz, 1H, H-1), 4.27 (dd, J=12.4 Hz, J=5.1 Hz, 1H, H-6a), 4.20-4.11 (m, 3H, H-6b, OCH$_2$CH$_3$), 3.81 (ddd, J=10.0 Hz, J=5.1 Hz, J=2.3 Hz, 1H, H-5), 2.09, 2.05, 2.03, 2.01 (4s, 4×3H, OAc), 1.26 (t, J=7.1 Hz, 3H, OCH$_2$CH$_3$) ppm. $^{13}$C NMR (125 MHz, CDCl$_3$) δ 170.7, 170.3, 169.4, 169.2, 166.9, 158.5, 102.3, 100.0, 72.8, 72.5, 70.8, 67.9, 61.7, 60.3, 20.8, 20.7, 14.4 ppm. HR-ESI-MS calcd for C$_{19}$H$_{27}$O$_{12}$ [M+H]$^+$ 447.1497, found 447.1500; calcd for C$_{19}$H$_{26}$NaO$_{12}$ [M+Na]$^+$ 469.1316, found 469.1324.

A 5 mL round-bottom flask containing (2R,3R,4S,5R,6R)-2-(acetoxymethyl)-6-(((E)-3-ethoxy-3-oxoprop-1-en-1-yl)oxy)tetrahydro-2H-pyran-3,4,5-triyl triacetate (125 mg, 0.28 mmoles) and 2-(2-Azidoethoxy)ethanol (734 mg, 5.6 mmoles, 20 eq.) was flushed with argon. Anhydrous DCM was added (500 µL) followed by N-bromosuccinimide (60 mg, 0.336 mmoles, 1.2 eq) at 0° C. The mixture was stirred at 0° C., and, after 3 h, the mixture was diluted in EtOAc. The organic layer was washed with H$_2$O (5 times) and brine. The organic layer was dried over Na$_2$SO$_4$. The crude mixture was concentrated and purified through 2 successive silica gel column chromatography (Hex:EtOAc, 6:4; then DCM:EtOAc, 95:5) to afford (2R,3R,4S,5R,6S)-2-(acetoxymethyl)-6-(1-(2-(2-azidoethoxy)ethoxy)-2-bromo-3-ethoxy-3-oxopropoxy)tetrahydro-2H-pyran-3,4,5-triyl triacetate (102 mg, 55%). R$_f$=0.37 (DCM:EtOAc, 9:1). $^1$H NMR (500 MHz, CDCl$_3$) δ 5.23 (t, J=9.5 Hz, 1H, H-3), 5.12-4.98 (m, 3H, H-2, H-4, OCH(OR)R), 4.87 (d, J=8.0 Hz, 1H, H-1), 4.30-4.19 (m, 4H, H-6a, CHBrCO$_2$Et, OCH$_2$CH$_3$), 4.15 (dd, J=12.2 Hz, J=5.7 Hz, 1H, H-6b), 3.97-3.88 (m, 1H, ½ OCH$_2$CH$_2$O), 3.78-3.72 (m, 2H, H-5, ½ OCH$_2$CH$_2$O), 3.71-3.67 (m, 2H, OCH$_2$CH$_2$N$_3$), 3.64-3.57 (m, 2H, OCH$_2$CH$_2$O), 3.44-3.37 (m, 2H, OCH$_2$CH$_2$N$_3$), 2.07, 2.04, 2.03, 2.00 (4s, 4×3H, CH$_3$CO), 1.29 (t, J=7.1 Hz, 3H, OCH$_2$CH$_3$) ppm. $^{13}$C NMR (125 MHz, CDCl$_3$) δ 170.6, 170.3, 169.5, 169.4, 167.5, 102.9, 98.7, 72.8, 72.1, 71.1, 70.2, 70.1, 68.7, 68.6, 62.3, 62.2, 61.9, 50.9, 45.7, 20.9, 20.8, 20.7, 14.02 ppm. HR-ESI-MS calcd for C$_{23}$H$_{34}$BrN$_3$NaO$_{14}$ [M+Na]$^+$ 678.1116, found 678.1121.

The (2R,3R,4S,5R,6S)-2-(acetoxymethyl)-6-(1-(2-(2-azidoethoxy)ethoxy)-2-bromo-3-ethoxy-3-oxopropoxy)tetrahydro-2H-pyran-3,4,5-triyl triacetate (75 mg, 0.11 mmoles) was dissolved in degassed t-BuOH (2.1 mL). At room temperature, NaBH$_3$CN (14.3 mg, 0.23 mmoles, 2 eq.) was added, followed by addition of Bu$_3$SnCl (6 µL, 0.023 mmoles, 0.2 eq.) and AIBN (3.7 mg, 0.023 mmoles, 2 eq.). The reaction mixture was sparged with Ar. The reaction mixture was illuminated with 365 nm light from a UV lamp for 4 h while maintaining vigorous stirring. The crude mixture was then concentrated and purified by silica flash chromatography (Hex:EtOAc, 6:4 to 1:1) to afford (2R,3R,4S,5R,6S)-2-(acetoxymethyl)-6-(1-(2-(2-azidoethoxy)ethoxy)-3-ethoxy-3-oxopropoxy)tetrahydro-2H-pyran-3,4,5-triyl triacetate as a clear viscous oil (56.9 mg, 87%). R$_f$=0.25 (DCM:EtOAc, 9:1). $^1$H NMR (500 MHz, CDCl$_3$) δ 5.25-5.17 (m, 2H, OCH(OR)R, H-3), 5.10-4.97 (m, 2H, H-2, H-4), 4.84 (d, J=8.1 Hz, 1H, H-1), 4.28-4.07 (m, 4H, OCH$_2$CH$_2$O), 3.86 (ddd, J=10.7 Hz, J=5.5 Hz, J=3.6 Hz, 1H, H-6a), 3.74 (ddd, J=10.2 Hz, J=5.4 Hz, J=2.8 Hz, 1H, H-5), 3.71-3.58 (m, 3H, H-6b, CH$_2$CH$_2$N$_3$), 3.39 (td, J=4.9 Hz, J=2.9 Hz, 2H, OCH$_2$CH$_2$N$_3$), 2.72 (ddd, J=10.3 Hz, J=6.7 Hz, J=3.0 Hz, 2H, OCHCH$_2$CO), 2.09, 2.03, 2.03, 2.00 (4s, 4×3H, CH$_3$CO), 1.26 (t, J=7.2 Hz, 3H, OCH$_2$CH$_3$) ppm. $^{13}$C NMR (150 MHz, CDCl$_3$) δ 170.6, 170.2, 169.4, 169.4, 169.2, 100.7, 96.4, 73.0, 72.0, 71.2, 70.2, 70.1, 68.5, 67.1, 62.1, 60.7, 50.7, 40.6, 20.7, 20.6, 14.17 ppm. HR-ESI-MS calcd for C$_{23}$H$_{35}$N$_3$NaO$_{14}$ [M+Na]$^+$ 600.2017, found 600.2028; calcd for C$_{23}$H$_{35}$KN$_3$O$_{14}$ [M+K]$^+$ 616.1756, found 616.1749.

A 25 mL round-bottom flask containing (2R,3R,4S,5R,6S)-2-(acetoxymethyl)-6-(1-(2-(2-azidoethoxy)ethoxy)-3-ethoxy-3-oxopropoxy)tetrahydro-2H-pyran-3,4,5-triyl triacetate (37 mg, 0.064 mmoles) was flushed with argon. A mixture of THF and water (1:1) was added (5 mL). LiOH.H$_2$O was then added (27 mg, 10 eq.) in one portion and the mixture was stirred at r.t. overnight. The mixture was then diluted with methanol and the base was neutralized using Amberlite IR-120 (H$^+$-form) resin. After filtration and concentration under vacuum, the crude was dissolved under argon in 4 mL of pyridine. 1 mL of acetic anhydride was then added and the mixture was stirred at r.t. for 3 h. The mixture was then concentrated, co-evaporated with toluene 3 times and the crude residue was then re-dissolved in THF (5 mL) and water (0.5 mL). After 30 minutes of stirring, the mixture was concentrated and co-evaporated with toluene. The crude product was then purified using silica gel column chromatography (DCM:EtOAc, 7:3 then DCM:MeOH, 97:3) to afford 3-(2-(2-azidoethoxy)ethoxy)-3-(((2S,3R,4S,5R,6R)-3,4,5-triacetoxy-6-(acetoxymethyl)tetrahydro-2H-pyran-2-yl)oxy)propanoic acid (14 mg, 40%). R$_f$=0.22 (DCM:MeOH, 96:4). $^1$H NMR (400 MHz, CDCl$_3$) δ 5.25-5.14 (m, 2H), 5.09-4.95 (m, 2H), 4.85 (d, J=8.1 Hz, 1H), 4.17 (d, J=4.0 Hz, 2H), 4.07-4.02 (m, 1H), 3.93-3.83 (m, 1H), 3.81-3.61 (m, 5H), 3.44-3.34 (m, 2H), 2.82-2.76 (m, 2H), 2.08 (s, 3H), 2.03 (s, 3H), 2.02 (s, 3H), 2.00 (s, 3H) ppm. LR-ESI-MS calcd for C$_{21}$H$_{31}$N$_3$NaO$_{14}$ [M+Na]$^+$ 572.17, found 572.17.

A 50 mL round-bottom flask containing 3-(2-(2-azidoethoxy)ethoxy)-3-(((2S,3R,4S,5R,6R)-3,4,5-triacetoxy-6-(acetoxymethyl)tetrahydro-2H-pyran-2-yl)oxy)propanoic acid (17 mg, 0.031 mmoles) and EDANS-NH$_2$ (11.2 mg, 0.042 mmoles, 1.3 eq.) was flushed with argon. Anhydrous DMF (0.7 mL) was then added, followed by DIPEA (22 µL, 0.13 mmoles, 4 eq.) and HBTU (13 mg, 0.036 mmoles, 1.1 eq.). The mixture was then stirred at r.t. overnight. After filtration through a plug of celite (DCM), the crude mixture was concentrated and co-evaporated with toluene. This crude mixture was then transferred into a 25 mL round-bottom flask containing DABCYL-Alkyne (22 mg, 0.071 mmoles, 2.2 eq.). After flushing with argon, 3 mL of anhydrous DCM were added followed by DIPEA (22 μL, 0.13 mmoles, 4 eq.) and Cu(MeCN)$_4$PF$_6$ (4.8 mg, 0.013 mmoles, 0.4 eq.). The mixture was stirred at r.t. overnight. After concentration, the crude mixture was diluted in methanol and neutralized using Amberlite IR-120 (Na$^+$-form) resin. Purification through silica gel column chromatography (DCM then DCM:MeOH, 96:4 then DCM:MeOH, 92:8) provided 5-((2-(3-(2-(2-(4-((4-((E)-(4-(dimethylamino)phenyl)diazenyl)benzamido)methyl)-1H-1,2,3-triazol-1-yl)ethoxy)ethoxy)-3-(((2S,3R,4S,5R,6R)-3,4,5-triacetoxy-6-(acetoxymethyl)tetrahydro-2H-pyran-2-yl)oxy)propanamido)ethyl)amino)naphthalene-1-sulfonic acid (13 mg, 39% over 2 steps). $R_f$=0.50 (DCM:MeOH, 90:10). HR-ESI-MS calcd for $C_{51}H_{62}N_9O_{17}S$ [M+H]$^+$ 1104.3979, found 1104.3977; calcd for $C_{51}H_{61}N_9NaO_{17}S$ [M+Na]$^+$ 1126.3798, found 1126.3811; calcd for $C_{51}H_{63}N_9O_{17}S$ [M+2H]$^2$+552.7026, found 552.7007.

A 5 mL round-bottom flask containing 5-((2-(3-(2-(2-(4-((4-((E)-(4-(dimethylamino)phenyl)diazenyl)benzamido)methyl)-1H-1,2,3-triazol-1-yl)ethoxy)ethoxy)-3-(((2S,3R,4S,5R,6R)-3,4,5-triacetoxy-6-(acetoxymethyl)tetrahydro-2H-pyran-2-yl)oxy)propanamido)ethyl)amino)naphthalene-1-sulfonic acid (12.9 mg) was flushed with argon. Anhydrous methanol (1.5 mL) was then added. Sodium methoxide (ca. 2 mg) was added and the mixture was stirred at r.t. overnight. The crude was then concentrated and dissolved in water (2 mL). A fraction of this crude mixture was purified thanks to semi-preparative scale HPLC (C-18, H$_2$O:MeCN, 15 to 60% MeCN gradient over 30 minutes, 2 mL·min$^{-1}$). Lyophilisation of the fractions containing the pure product provided 5-((2-(3-(2-(2-(4-((4-((E)-(4-(dimethylamino)phenyl)diazenyl)benzamido)methyl)-1H-1,2,3-triazol-1-yl)ethoxy)ethoxy)-3-(((2S,3R,4S,5S,6R)-3,4,5-trihydroxy-6-(hydroxymethyl)tetrahydro-2H-pyran-2-yl)oxy)propanamido)ethyl)amino)naphthalene-1-sulfonic acid 7 (4.4 mg) as an orange fluffy powder. HPLC retention time=17.2 mins (C18 Semi-Prep, H$_2$O:MeCN, 90:10 to 45:55 over 30 minutes, 2 mL·min$^{-1}$). $^1$H NMR (600 MHz, MeOD) δ 8.18 (d, J=8.8 Hz, 1H, CH-edans), 8.15-8.08 (m, 2H, CH-edans), 8.01-7.96 (m, 2H, CH-dabcyl), 7.90 (s, 1H, H-triaz), 7.87-7.82 (m, 4H, CH-dabcyl), 7.41-7.33 (m, 2H, CH-edans), 6.85-6.79 (m, 2H, CH-dabcyl), 6.63 (d, J=7.5 Hz, 1H, CH-edans), 5.08 (t, J=5.6 Hz, 1H, OCH(OR), 4.65 (s, 2H, CH$_2$NHC(O)-dabcyl), 4.44 (d, J=7.9 Hz, 1H, H-1), 4.41 (dt, J=5.4 Hz, J=4.1 Hz, 2H, CH$_2$-Ntriaz), 3.90 (dt, J=11.2 Hz, J=4.4 Hz, 1H, ½ OCH$_2$CH$_2$O), 3.83 (dd, J=11.8 Hz, J=2.3 Hz, 1H, H-6a), 3.68-3.63 (m, 2H, CH$_2$CH$_2$N-triaz), 3.59-3.49 (m, 4H, H-6b, ½ OCH$_2$CH$_2$O, CH$_2$CH$_2$NH-edans), 3.39 (t, J=4.7 Hz, 2H, OCH$_2$CH$_2$O), 3.37 (t, J=5.9 Hz, 2H, CH$_2$CH$_2$NH-edans), 3.34-3.27 (m, 1H, H-3), 3.23 (ddd, J=9.3 Hz, J=6.7 Hz, J=2.4 Hz, 1H, H-5), 3.17 (dd, J=9.3 Hz, J=7.9 Hz, 1H, H-2), 3.14-3.10 (m, 1H, H-4), 3.10 (s, 6H, N(CH$_3$)$_2$), 2.67 (dd, J=14.3 Hz, J=5.9 Hz, 1H, CH$_2$C(O)NHCH$_2$R), 2.56 (dd, J=14.3 Hz, J=5.3 Hz, 1H, CH$_2$C(O)NHCH$_2$R) ppm. $^{13}$C NMR (150 MHz, MeOD) δ 172.7, 169.5, 156.5, 154.7, 146.1, 145.5, 144.9, 142.1, 135.5, 131.5, 129.5, 128.5, 126.7, 126.4, 125.7, 125.4, 125.1, 123.7, 123.0, 116.6, 112.6, 105.2, 102.2, 99.8, 78.13, 78.09, 74.9, 71.8, 71.0, 70.1, 68.3, 62.8, 51.3, 45.0, 43.5, 40.4, 39.7, 36.3 ppm. HR-ESI-MS calcd for $C_{43}H_{54}N_9O_{13}S$ [M+H]$^+$±936.3556, found 936.3561; calcd for $C_{43}H_{53}N_9NaO_{13}S$ [M+Na]$^+$ 958.3376, found 958.3383.

Example 8

Glc-H-BABS(TAMRA/BHQ2): 5-((6-(3-(2-(2-(4-((4-((4-((E)-(2,5-dimethoxy-4-((E)-(4-nitrophenyl)diazenyl)phenyl)diazenyl)phenyl)(methyl)amino)butanamido)methyl)-1H-1,2,3-triazol-1-yl)ethoxy)ethoxy)-3-(((2S,3R,4S,5S,6R)-3,4,5-trihydroxy-6-(hydroxymethyl)tetrahydro-2H-pyran-2-yl)oxy)propanamido)hexyl)carbamoyl)-2-(6-(dimethylamino)-3-(dimethyliminio)-3H-xanthen-9-yl)benzoate

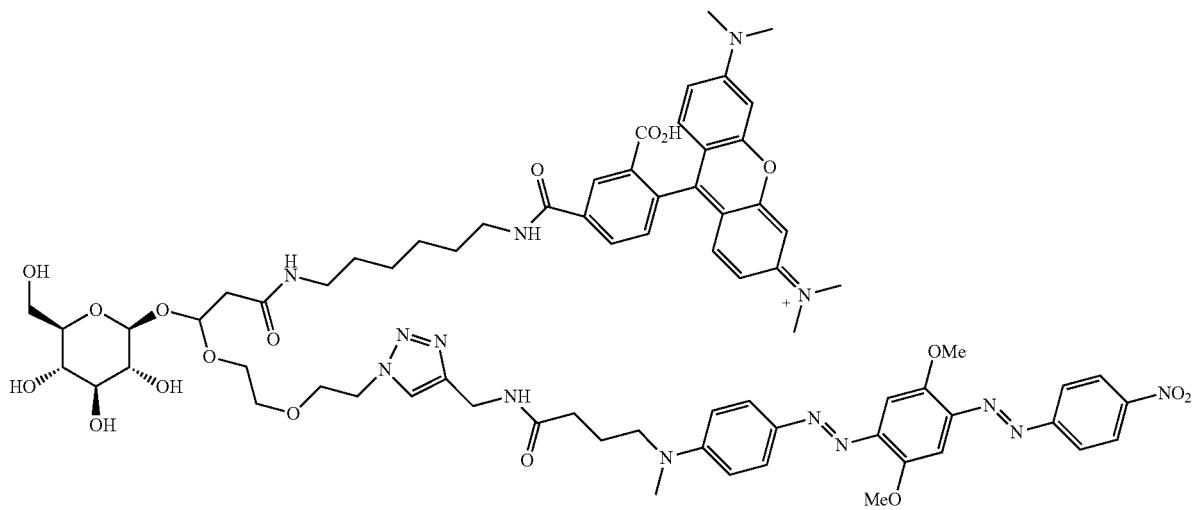

Compound 8 was synthesized according to procedures analogous to the synthesis of compound 7.

$R_f$=0.20 (EtOAc:MeOH, 1:1). $^1$H NMR (400 MHz, MeOD) δ 8.49 (d, J=1.8 Hz, 1H), 8.43-8.36 (m, 2H), 8.12-8.03 (m, 3H), 7.97 (s, 1H), 7.78 (d, J=9.1 Hz, 2H), 7.49 (d, J=7.9 Hz, 1H), 7.40 (d, J=15.5 Hz, 2H), 7.15 (d, J=9.5 Hz, 2H), 6.85 (dd, J=9.5, 2.5 Hz, 2H), 6.83-6.73 (m, 4H), 5.14 (t, J=5.7 Hz, 1H), 4.63-4.50 (m, 3H), 4.47 (s, 2H), 4.04 (s, 3H), 4.03-3.99 (m, 1H), 3.96 (s, 3H), 3.92 (dd, J=11.8, 2.2 Hz, 1H), 3.87 (t, J=5.0 Hz, 2H), 3.71-3.57 (m, 4H), 3.53-3.44 (m, 4H), 3.41-3.36 (m, 1H), 3.29-3.22 (m, 5H), 3.20 (s, 14H), 3.10 (s, 3H), 2.69 (dd, J=14.2, 6.2 Hz, 1H), 2.56 (dd, J=14.2, 5.2 Hz, 1H), 2.33 (t, J=7.2 Hz, 2H), 1.97 (q, J=7.4 Hz, 2H), 1.69 (d, J=7.4 Hz, 2H), 1.54 (d, J=6.6 Hz, 2H), 1.45 (d, J=4.6 Hz, 4H) ppm. HR-ESI-MS calcd for $C_{72}H_{87}N_{14}O_{18}$ [M+H]$^+$ 1435.6317, found 1435.6272; calcd for $C_{72}H_{86}N_{14}NaO_{18}$ [M+Na]$^+$ 1457.6137, found 1457.6070; calcd for $C_{72}H_{88}N_{14}O_{18}$ [M+2H]$^{2+}$ 718.3195, found 718.3185.

Examples 9 to 14, as indicated in Table 1, are synthesized according to procedures analogous to the schemes and examples outlined herein.

Example 15

Fluorescence Quenching Efficiency of Glyco-BABS 1, 2, 6 and 7

Figure 3:
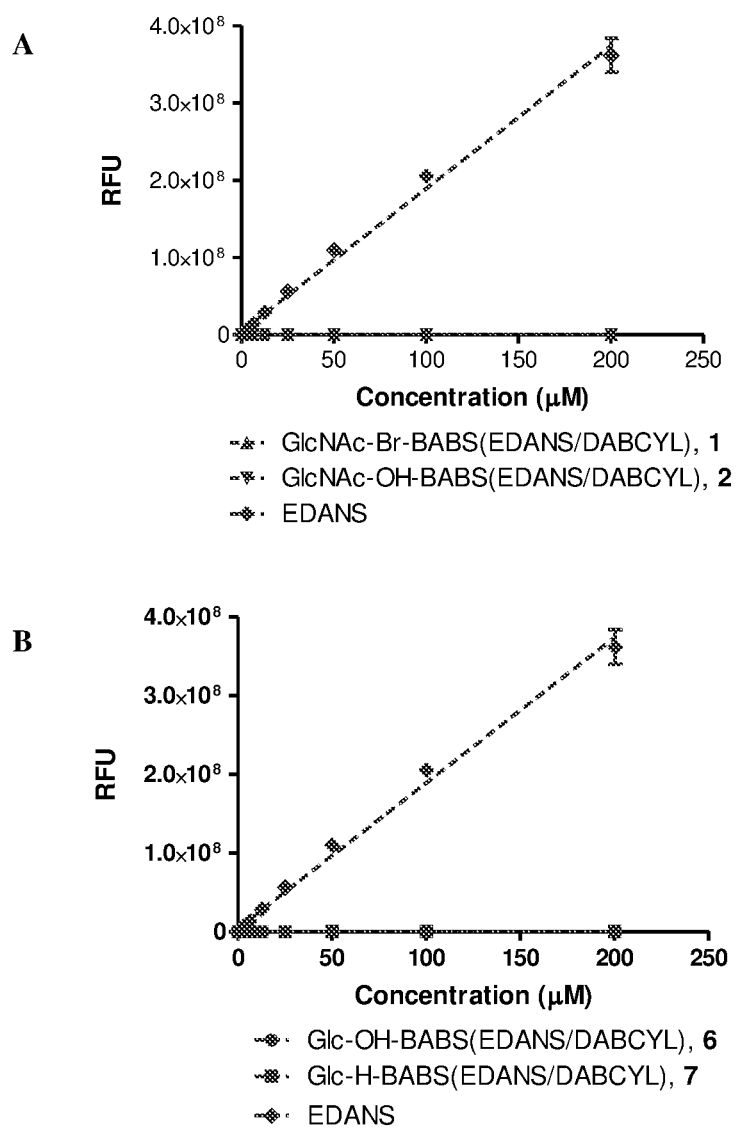
FIGS. 3A-B are graphs showing the determination of quenching efficiency of Glyco-BABS 1, 2, 6 and 7.

Determination of the quenching efficiencies for Glyco-BABS 1, 2, 6 and 7 using concentration dependent variation in the fluorescence emission of the Glyco-BABS and its corresponding fluorophore EDANS: The quenching efficiencies was determined by measuring the residual fluorescence of different concentration of Glyco-BABS in PBS (45 μL) and comparing it with the fluorescence of equivalent concentrations of EDANS. Fluorescence was measured in quadruplicates (384-well plates) using a SpectraMax i3x plate reader. The quenching efficiency was measured as the ratio of slopes. FIG. 3 shows the plot of the fluorescence emission intensity versus concentration of Glyco-BABS 1, 2, 6 and 7 and EDANS. The data show efficient quenching of EDANS fluorescence in all Glyco-BABS. The measured quenching efficiency are 99.93% for GlcNAc-Br-BABS 1, 99.89% for GlcNAc-OH-BABS 2, 99.95% for Glc-OH-BABS 6 and 99.87% for Glc-H-BABS 7.

Example 16

In Vitro Kinetic Assay for GlcNAc-BABS 1 and 2 with hOGA

Figure 4:
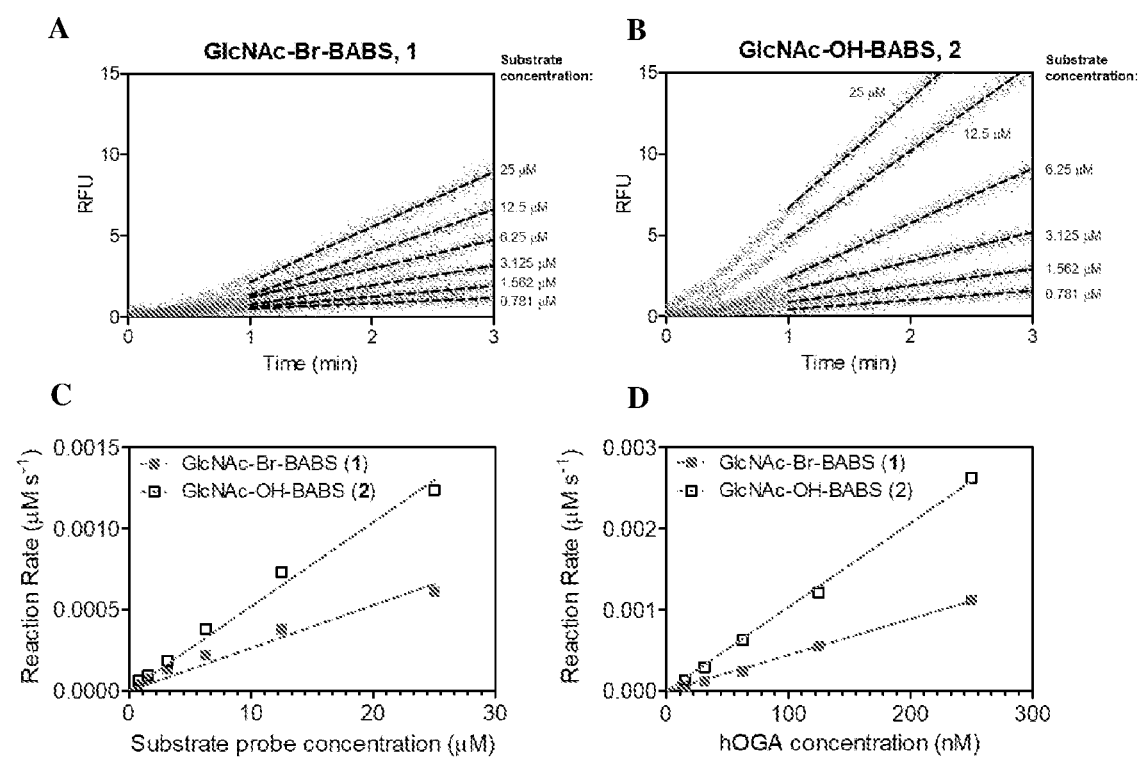
FIGS. 4A-D are graphs showing the in vitro kinetic assays for GlcNAc-BABS 1 and 2 with the human O-GlcNAcase (hOGA)

GlcNAc-BABS probes are turned over by hOGA (FIG. 4). Continuous assays were performed in 160 μL fluorometer cuvettes at 37° C. in PBS. Reactions were initiated by the addition of com recombinant hOGA and the reaction was monitored continuously. Standard curves were constructed using EDANS using the same buffer conditions. hOGA catalyzed hydrolysis of GlcNAc-Br-BABS 1 and GlcNAc-OH-BABS 2 revealed $k_{cat}/K_m$ values of 263 and 519 M$^{-1}$ s$^{-1}$, respectively. Interestingly, these values are comparable to the second order rate constant measured for methyl β-D-N-acetylglucopyranoside[39] (440 M$^{-1}$ s$^{-1}$) and about 50-fold higher than the rate constants measured for O-GlcNAc-modified protein substrates.[40] We also confirmed that the observed rates were linearly dependent on hOGA concentrations. FIG. 4A shows evolution of fluorescence (RFU) for different concentrations of GlcNAc-BABS 1 and 2 in presence of hOGA. Dotted lines represent the linear rates reached at steady state. FIG. 4B shows rates of hOGA catalyzed hydrolysis of different concentrations of GlcNAc-BABS. FIG. 4C shows rates of hydrolysis of GlcNAc-BABS depend on the concentrations of hOGA.

Example 17

Interrupted Assay for Determination of Hemiacetal Breakdown

Figure 5:
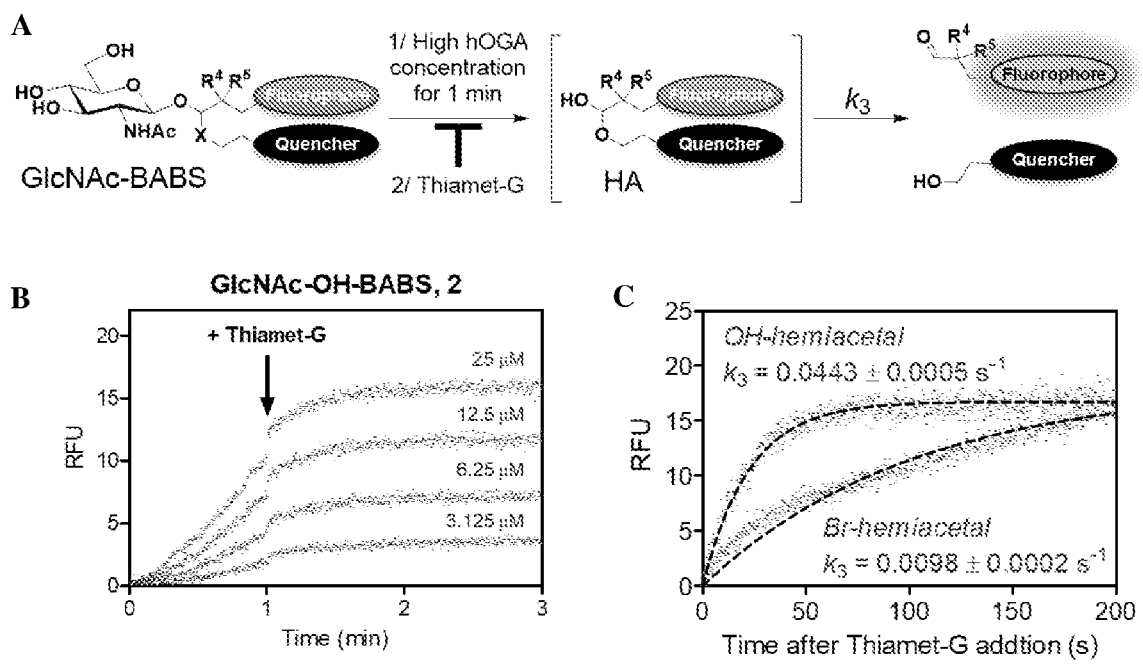
FIG. 5A is a schematic showing the hemiacetal breakdown assay design containing high hOGA concentration, stopped after 1 minute by addition of Thiamet-G.
FIGS. 5B-C are graphs showing in vitro measurements of the hemiacetal intermediate breakdown for GlcNAc-BABS 1 and 2.

During in vitro kinetic assays with GlcNAc-BABS 1 and 2 and one can noticed a short (~1 min) initial lag in the initial rate experiments (FIG. 4). We speculated that this lag stemmed from an approach to steady state conditions whereupon the concentration of a hemiacetal (HA) intermediate would increase and then remain constant. To test this idea and determine the first order rate constant for decomposition of these hemiacetals (HA), we developed an assay in which we can rapidly halt enzyme activity (FIG. 5). The assay was initiated by addition of a high concentration of hOGA, allowed to proceed for one minute, and the enzymatic reaction was then rapidly stopped by addition of a high concentration of the tight binding hOGA inhibitor Thiamet-G (100 μM; 50000×$K_i$; $K_i$=2 nM). We could then monitor the decomposition of any accumulated hemiacetal (HA). Interestingly, we found that the hemiacetal (HA) generated from GlcNAc-OH-BABS 2 broke down 4.5 times faster than the one generated from GlcNAc-Br-BABS 1, with an observed first order rate constant ($k_3$) of 4.4×10$^{-2}$ and 1×10$^{-2}$ s$^{-1}$ respectively. FIG. 5A shows the hemiacetal breakdown assay design containing high hOGA concentration. Stopped after 1 minute by addition of Thiamet-G. FIG. 5B shows evolution of fluorescence for the hemiacetal breakdown assay with different concentrations of GlcNAc-OH-BABS. FIG. 5C shows measurement of first-order rate constants for the breakdown of hemiacetal after addition of Thiamet-G.

Example 18

In Vitro Kinetic Assay for Glc-BABS 6 and 7 with Human GBA Enzymes

Figure 6:
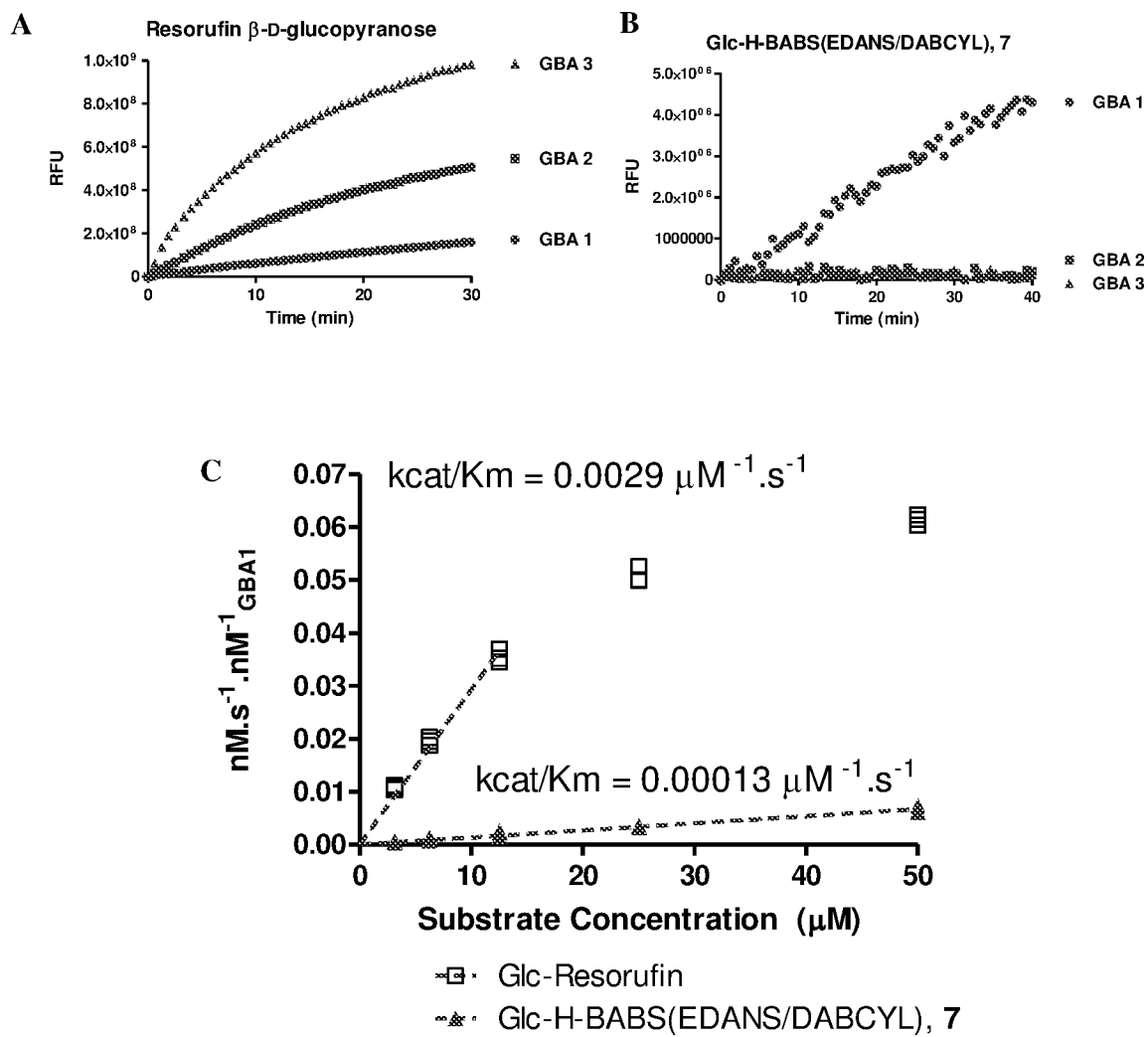
FIGS. 6A-C are graphs showing the in vitro kinetic assays for Glc-BABS 7 with the exo-glycosidases GBA1, GBA2 and GBA3.

Glc-H-BABS 7 is turned over specifically by GBA1 but not by GBA2 or 3. Activity of GBA1, GBA2 and GBA3 enzymes (at 50 nM) was checked using 20 μM Resorufin β-D-glucopyranoside (Glc-resorufin, Sigma) (FIG. 6). Using similar conditions, we observed that Glc-OH-BABS (EDANS/DABCYL) 6 is not turned over by any of the GBA enzymes but Glc-H-BABS(EDANS/DABCYL) 7 was turned over by GBA1 only. Measurements of initial rates using 20 nM GBA1 and different concentrations of Glc-resorufin and Glc-H-BABS 7 allowed us to determine second order rate constants $k_{cat}/K_m$ of 0.0029 μM$^{-1}$ s$^{-1}$ and 0.00013 μM$^{-1}$ s$^{-1}$ respectively (FIG. 6).

Example 19

In Vitro Kinetic Assay for Gal-BABS 4 and 5 with Human GALC

Figure 7:
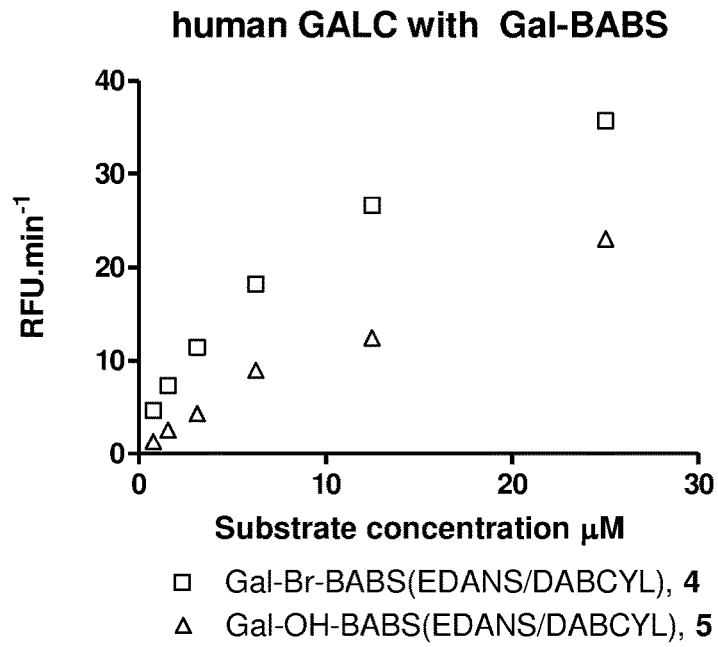
FIG. 7 is a graph showing the in vitro kinetic assays for Gal-BABS 4 and 5 with the human galactosylceramidase (hGALC)

Gal-Br-BABS 4 and Gal-OH-BABS 5 are turned over human Galactosylceramidase (GALC). Continuous assay was started by the addition of 5 nM of commercial recombinant human GALC in different concentrations of Gal- BABS 4 and 5. FIG. 7 shows linear increase of activity with the concentration of Gal-BABS.

Example 20 pH Stability of GlcNAc-BABS 1 and 2 and Glc-BABS 6 and 7

Figure 8:
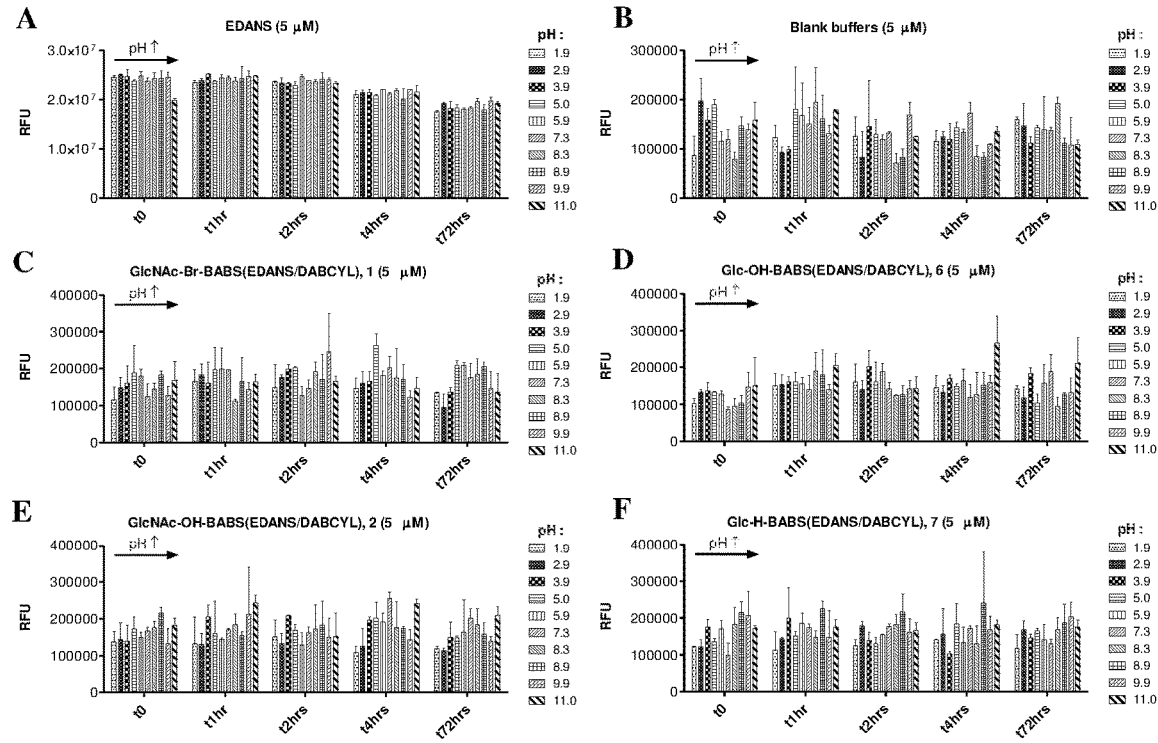
FIGS. 8A-F are graphs showing the stability of Glyco-BABS compound 1, 2, 6 and 7 across a wide range of pH.

One concern with the Glyco-BABS design was the known lability of acetals under acidic conditions that has been exploited in pH-sensitive prodrugs or linkers for drug delivery.[41,42] However, we recognized that carbohydrate anomeric acetals are chemically distinct from regular acetals. Due to stabilization by the endocyclic oxygen, we expected these bis-acetals would show stability across a range of physiological pH values. We therefore assessed the stability of the bis-acetal motif toward acid and base hydrolysis (FIG. 8). To do so, we tested the pH stability of 5 μM of GlcNAc-Br-BABS 1, GlcNAc-OH-BABS 2, Glc-OH-BABS 6 and Glc-H-BABS 7 at different pH over time. We prepared solutions at various pH by mixing 0.2 M KCl+0.1 M HCl with 0.2 M KCl+0.1 M KOH. Fluorescence of EDANS and Glyco-BABS solutions (5 μM, 45 μL) at different pH was measured at different time points in Nunc 384-well plates using a SpectraMax i3x plate reader. Data (triplicates) support the highly efficient quenching and the stability of these substrates over a wide range of pH. Indeed, no significant increase of fluorescence was observed for all Glyco-BABS even after 72 h at pH as low a 2 and as high a 10

Example 21 hOGA can Cleave GlcNAc-BABS 2 within SK-N-SH Lysate

Figure 9:
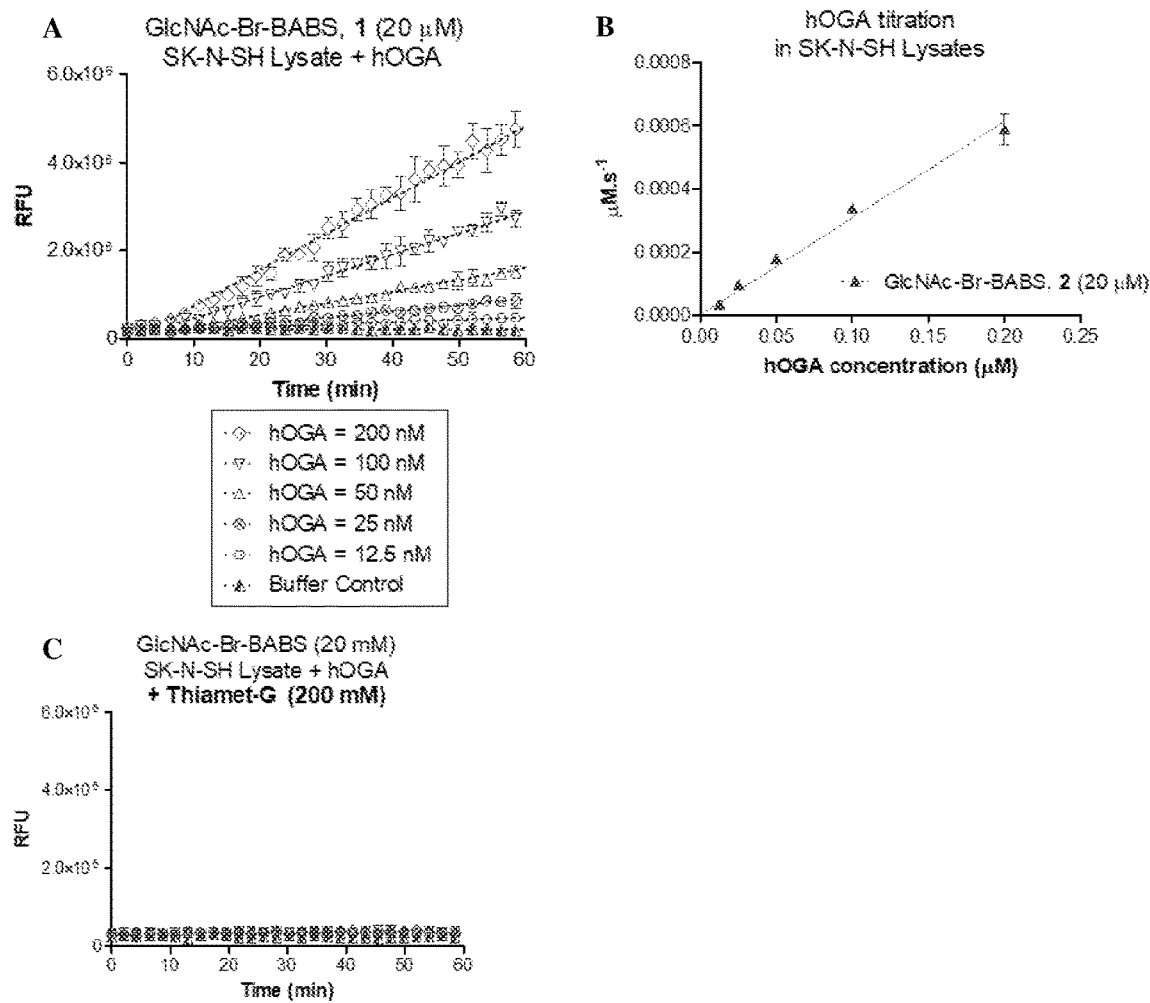
FIGS. 9A-C are graphs showing the ability of hOGA to cleave GlcNAc-BABS 1 within SK-N-SH lysate.

To evaluate the compatibility of the BABS design with complex cellular extracts, we also measured the turnover of GlcNAc-Br-BABS in SK-N-SH cell lysate in the presence of increasing concentrations of hOGA (FIG. 9). We found that this substrate is efficiently processed within lysates, at rates that are comparable to buffer alone. FIG. 9A shows fluorescence measured at 25° C. in 384-well plates using 20 μM of GlcNAc-Br-BABS 1 in SK-N-SH lysate and increasing concentrations of recombinant hOGA. Buffer control consists of PBS supplemented to lysis buffer. FIG. 9B shows rates of GlcNAc-Br-BABS in lysates are linearly dependent on hOGA concentration and are similar to rates observed in buffer alone. These data highlight the compatibility of GlcNAc-Br-BABS 1 with the complex milieu of a cellular extract. FIG. 9C shows that addition of the potent and selective hOGA inhibitor Thiamet-G (200 μM) completely inhibits the substrate's turnover, demonstrating the specificity of the observed signal. Error bars represent standard deviation over quadruplicate.

Example 22

Evaluation of Glc-BABS 8 in SK-N-SH Live Cells

Figures 10, 11:
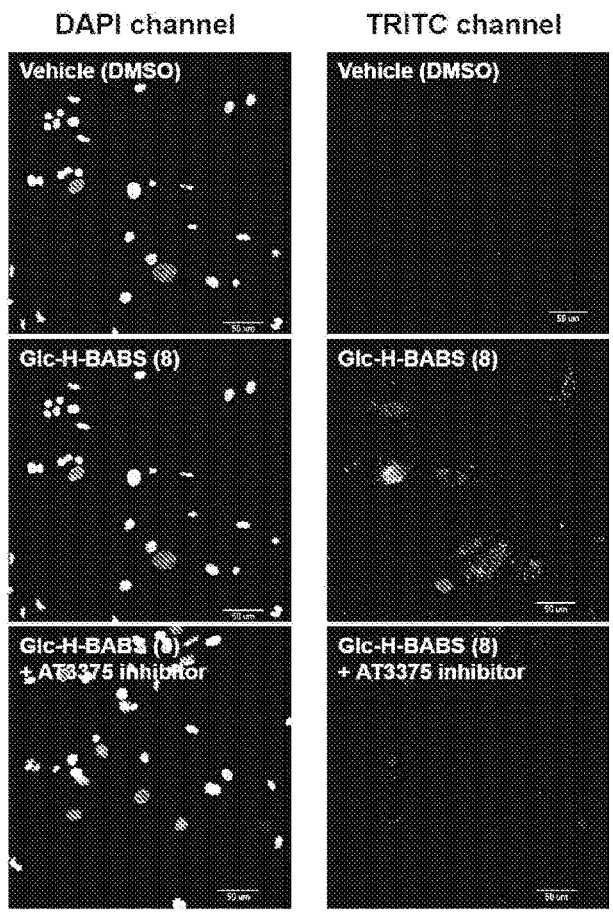
FIG. 10 shows processing of fluorescence quenched Glc-BABS 8 occurs in live cells (triplicates for each condition, 9 sites per well). Vehicle are cells treated with DMSO (1%). Fluorescence is measured for the DAPI channel (to stain nuclei) and the TRITC channel (TAMRA fluorescence). Treatment with the GBA1 inhibitor almost completely abolish the fluorescent signal, supporting specific turnover of the Glc-BABS 8 by the GBA1 enzyme.
FIG. 11 shows representative images of one of the 9 sites imaged for each well a 96-well plate. Vehicle are cells treated with DMSO (1%). Fluorescence is measured for the DAPI channel (to stain nuclei) and the TRITC channel (TAMRA fluorescence). Glc-BABS 8-treated cells show punctuated signal supporting the lysosomal localization of the processing of the substrate. Glc-BABS 8 and AT3375 inhibitor-treated cells show clear decrease of the signal with a residual signal similar to the background noise observed for vehicle-treated cells, suggesting specific turnover of Glc-BABS 8 by GBA1 and efficient inhibition of the enzyme by AT3375. Scale bars represent 50 μm.
Figure 12:
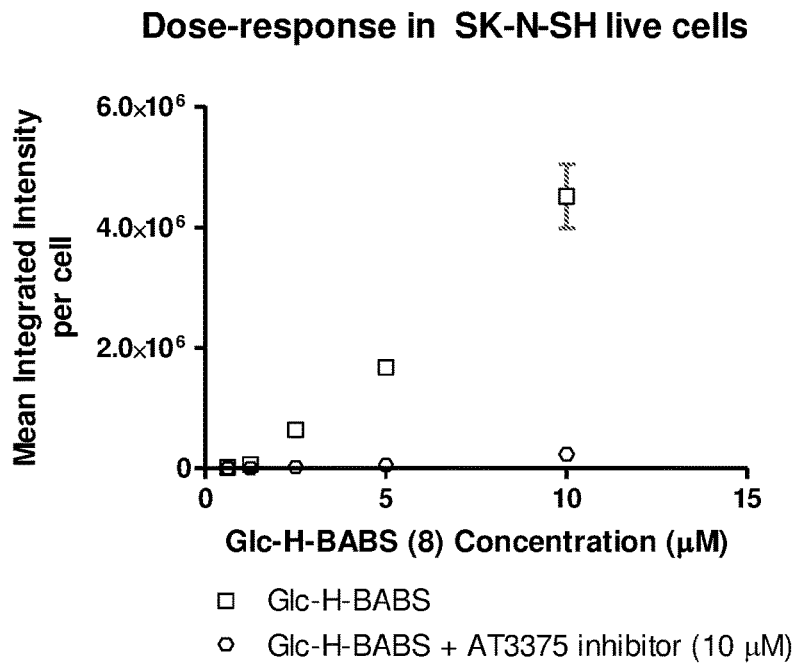
FIG. 12 shows that Glc-H-BABS 8 shows dose dependent increases in fluorescence upon incubation with human SK-N-SH cells. Treatment with GBA1 inhibitor AT3375 confirms the specificity of Glc-BABS 8 towards GBA1. From the images, the total mean integrated intensity was measured for the TRITC channel and divided by the number of cells within the imaging site as determined by the DAPI staining. Measurements at various concentrations of Glc-BABS 8 reveals a linear increase in fluorescence as a function of substrate concentration. Error bars represent the standard deviation obtained from triplicates (3 separate wells, 9 sites imaged in each well)
Figure 13:
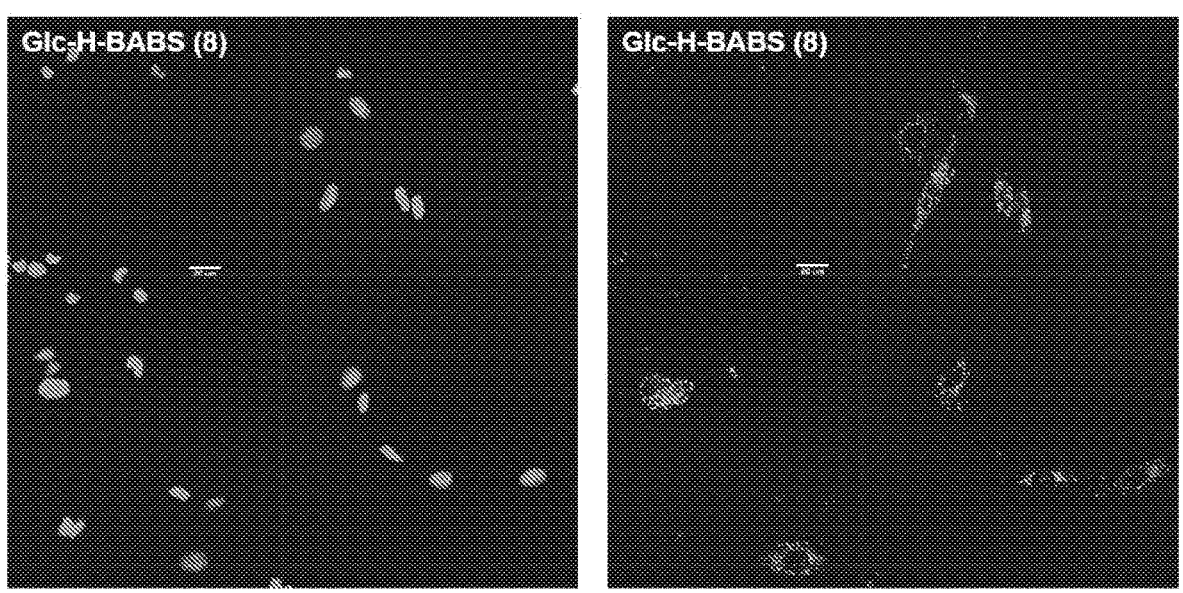
FIG. 13 shows a representative zoom on images from Glc-H-BABS treated cells (5 μM, 2 h incubation time). This image shows punctuated fluorescence and low background noise. Scale bars represent 20 μm.

The Glc-H-BABS(TAMRA/BHQ2) 8 was also evaluated in the human neuronal cell culture model cells SK-N-SH. High content imaging of SK-N-SH cells treated with DAPI, to stain nuclei, and 5 μM of Glc-BABS 8 revealed fluorescence in a punctuate pattern consistent with a lysosomal distribution (FIG. 10, FIG. 11). Cells plated in a 96-well clear-bottom Corning plate were treated with vehicle, 5 μM of Glc-BABS 8 alone or 5 μM of Glc-BABS 8 with 10 μM of the GBA1 inhibitor AT3375. After incubation at 37° C. and 5% $CO_2$ for 1 to 2 h, the media was removed and the cells were washed. The plate was then imaged using a Molecular Devices ImageXpress XLS High-Content Imager Importantly, cells treated with the inhibitor showed a significant reduction of the punctuated fluorescent signal (FIG. 13). By integrating the fluorescence intensity from randomly selected fields, it was possible to observe a quantitative increase in fluorescence with increasing concentrations of the Glc-BABS 8. Next, it was established that there is a dose-dependent cellular fluorescence where a linear increase in fluorescence was observed that depended on the concentration of Glc-BABS 8 (FIG. 12). These data reveal Glc-BABS 8 is processed in cells to result in the fluorescent product, and the observed fluorescence is dependent on GBA1 activity.

FIG. 10 shows the images for the triplicate treatments of live SK-N-SH cells. Within each well, 9 sites were imaged for DAPI fluorescence and TAMRA fluorescence (TRITC channel). FIG. 11 shows a representative site for each treatment conditions. Images intensity for each channel are scaled similarly. FIG. 12 shows the Mean Integrated Intensity of the TAMRA fluorescence divided by the number of cells in each well in function of the Glc-H-BABS 8 concentration. This data shows a linear dose-response relationship.

Example 23

Measurement of a GBA1 Inhibitor IC50 in SK-N-SH Live Cells

Figure 14:
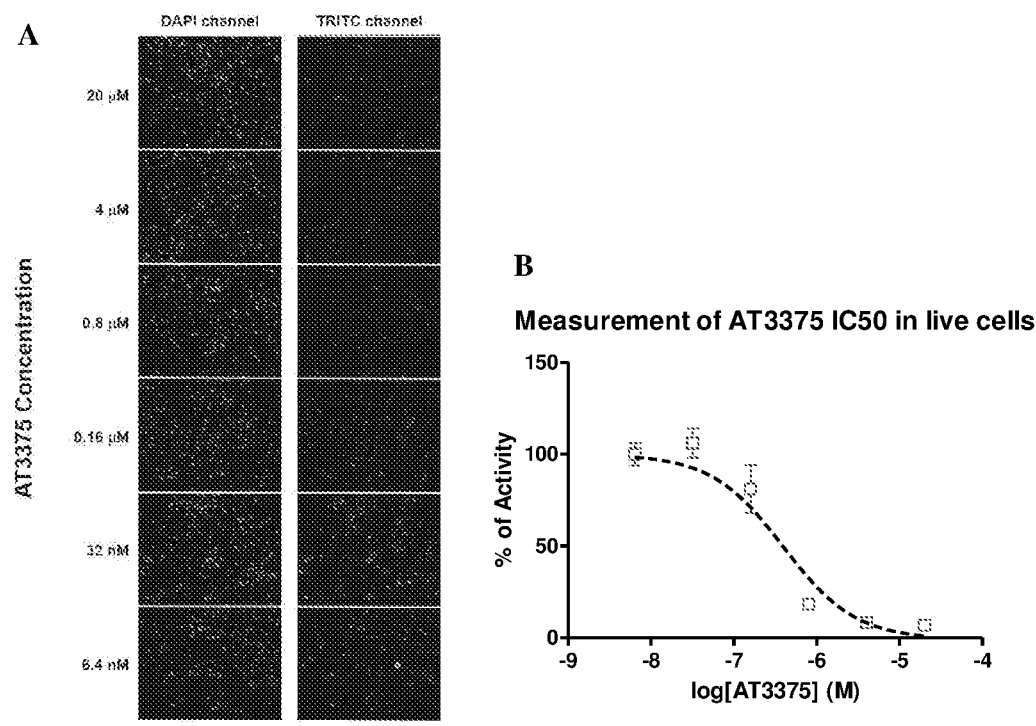
FIG. 14A shows representative images of live SK-N-SH cells treated with Glc-H-BABS (5 μM) and different concentrations of the GBA1 inhibitor AT3375 (2 h incubation time). Integration of the fluorescence and determination of the mean integrated intensity per cell allows to determine a percentage of activity for each inhibitor concentration treatments (no inhibitor control is used to determine 100% activity)
FIG. 14B shows a plot of the percentage of activity against the log of AT3375 concentration allows to determine the inhibitor's IC50 in live cells.
Figure 15:
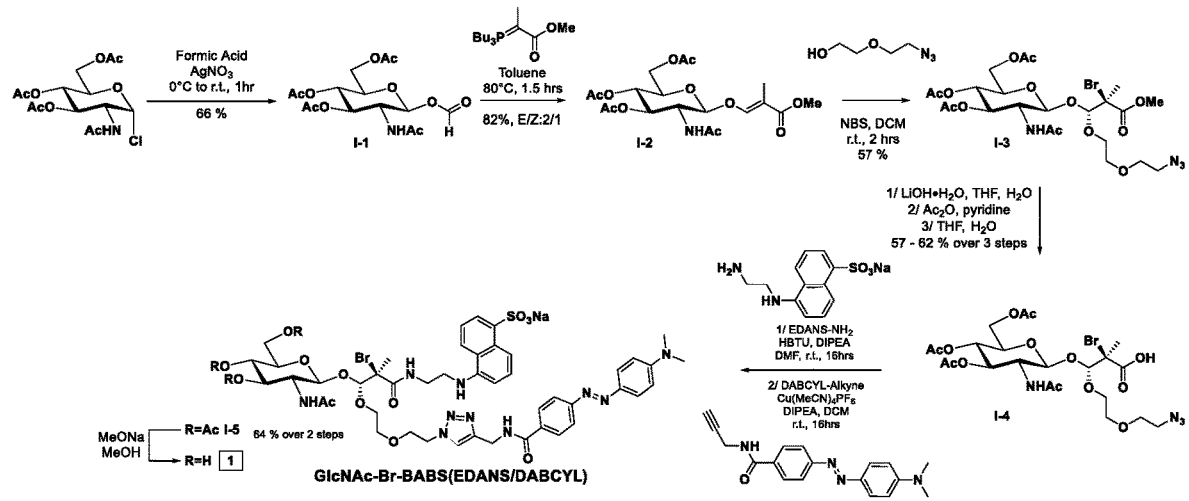
FIG. 15 shows the synthetic route used to prepare GlcNAc-Br-BABS(EDANS/DABCYL) (Compound 1, Table 1)
Figure 16:
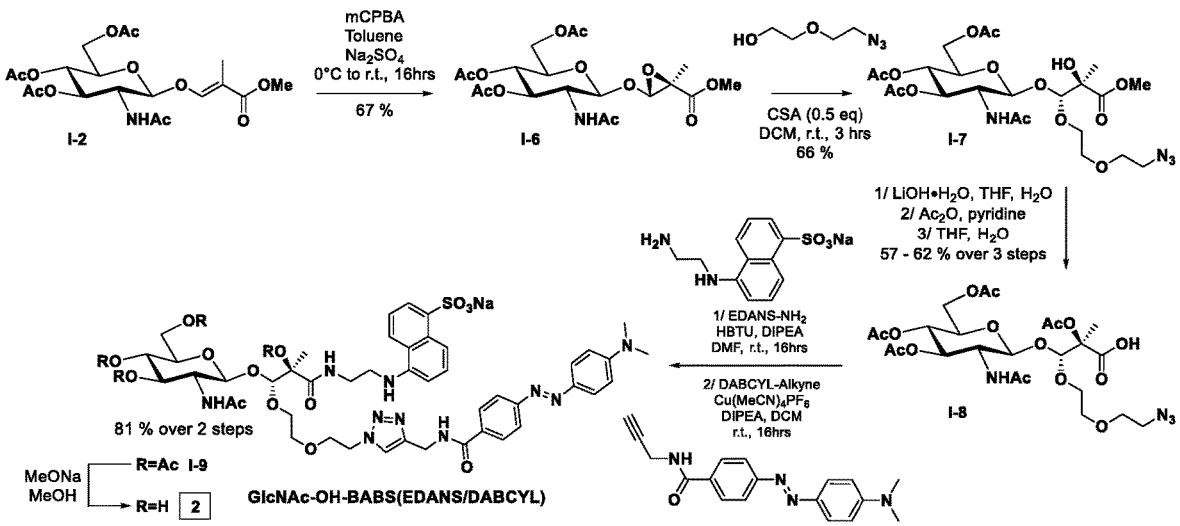
FIG. 16 shows the synthetic route used to prepare GlcNAc-OH-BABS(EDANS/DABCYL) (Compound 2, Table 1)
Figure 17:
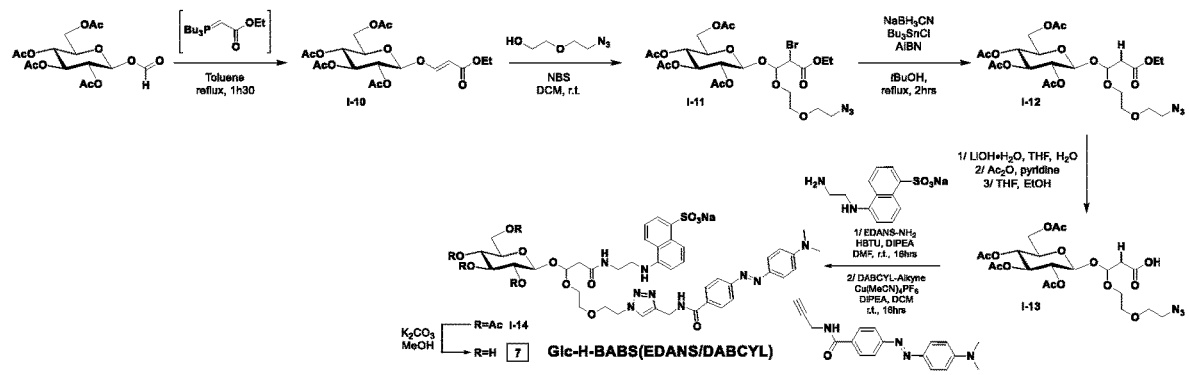
FIG. 17 shows the synthetic route used to prepare Glc-H-BABS(EDANS/DABCYL) (Compound 7, Table 1)
Figure 18:
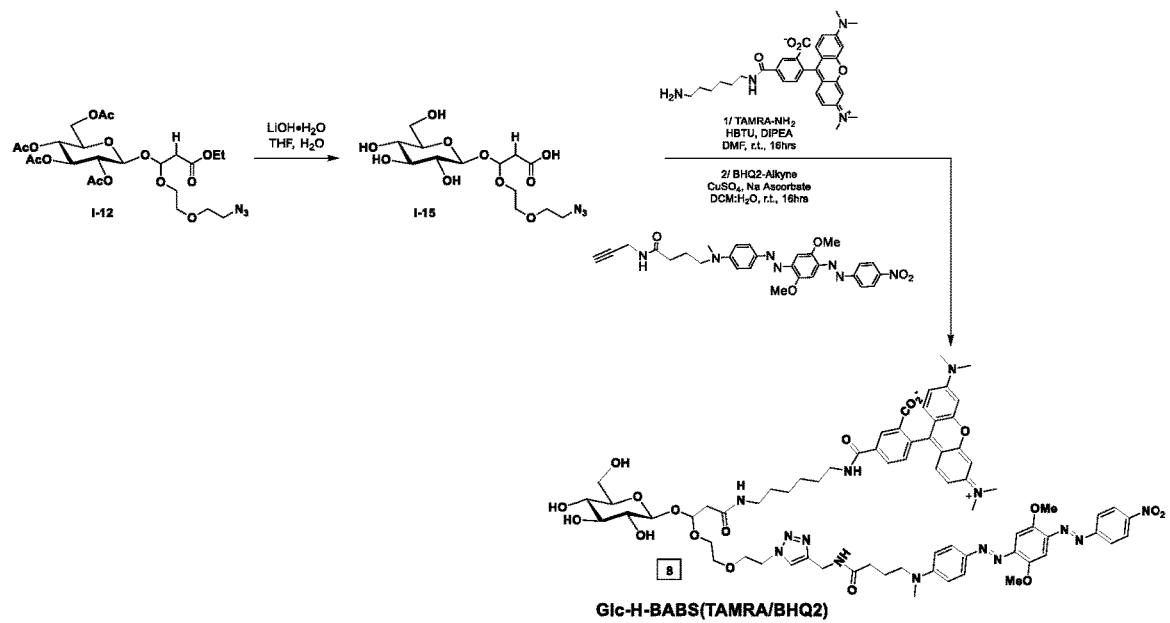
FIG. 18 shows the synthetic route used to prepare Glc-H-BABS(TAMRA/BHQ2) (Compound 8, Table 1).

Glc-H-BABS(TAMRA/BHQ2) 8 can be used to measure the potency of a GBA1 inhibitor in live cells. High content imaging of SK-N-SH cells incubated for 2 h with DAPI, to stain nuclei, 5 μM of Glc-BABS 8 and varying concentrations of the GBA1 inhibitor AT3375 revealed decreasing fluorescence signal with increasing inhibitor concentration (FIG. 14). Cells were plated in a 96-well clear-bottom Corning plate and treated with vehicle, 5 μM of Glc-BABS 8 alone or 5 μM of Glc-BABS 8 with different concentrations of the GBA1 inhibitor AT3375 (triplicates). After incubation at 37° C. and 5% $CO_2$ for 2 h, the media was removed and the cells were washed. The plate was then imaged using a Molecular Devices ImageXpress XLS High-Content Imager. Integration of the mean fluorescence intensity per cell from randomly selected fields (9 sites per well), the percentage of activity (no inhibitor as a 100% activity control) was plotted against the log of the AT3375 inhibitor concentration to determine the IC50 in cells. These data reveal Glc-H-BABS 8 can be used to measure the effect of an inhibitor on an exo-glycosidase activity in live cells.

Collectively, Examples 1 to 23 demonstrate the synthesis and utility of novel fluorescence quenched substrates for exo-glycosidase. These Glyco-Bis-Acetal-based substrates are very efficiently quenched when intact, but give rise to fluorescence when hydrolytically cleaved by exo-glycosidases. Several Glyco-BABS show greater than 99.9% quenching efficiency, which enables direct visualization of exo-glycosidase activity in live cells.

The present invention has been described with regard to one or more embodiments. However, it will be apparent to persons skilled in the art that a number of variations and modifications can be made without departing from the scope of the invention as defined in the claims.

REFERENCES

1. V. Lombard, et al., *Nucleic Acids Research* 2014, 42, D490-D495.
2. R. E. Boyd, et al., *Journal of Medicinal Chemistry* 2013, 56, 2705-2725.
3. E. Sidransky, G. Lopez, *The Lancet Neurology* 2012, 11, 986-998.
4. S. A. Yuzwa, D. J. Vocadlo, *Chemical Society Reviews* 2014, 43, 6839-6858.
5. L. He, et al., *Nat. Commun.* 2011, 2, 307.
6. R. O. Brady, et al., *J Clin Invest* 1966, 45, 1112-5.
7. T. Cox, et al., *Lancet* 2000, 355, 1481-5.
8. J. Q. Fan, et al., *Nat Med* 1999, 5, 112-5.
9. A. R. Sawkar, et al., *Proc Natl Acad Sci USA* 2002, 99, 15428-33.
10. F. Richter, et al., *Neurotherapeutics* 2014, 11, 843-856.
11. G. J. Kornhaber, et al., *Chembiochem* 2008, 9, 2643-9.
12. A. McNeill, et al., *Brain* 2014, 137, 1481-95.
13. M. B. Tropak, et al., *Chembiochem* 2008, 9, 2650-62.
14. D. J. Vocadlo, *Current Opinion in Chemical Biology* 2012, 16, 488-497.
15. M. Garland, J. J. Yim, and M. Bogyo, *Cell Chemical Biology* 2016, 23, 122-136.
16. H.-Y. Hu, et al., *Angew. Chem., International Edition in English* 2014, 53, 7669-7673.
17. M. Whitney, et al., *Angew. Chem., International Edition in English* 2013, 52, 325-330.
18. M. J. Evans, B. F. Cravatt, *Chemical Reviews* 2006, 106, 3279-3301.
19. L. E. Edgington, M. Verdoes, and M. Bogyo, *Curr Opin Chem Biol* 2011, 15, 798-805.
20. V. Cortez-Retamozo, et al., *J Clin Invest* 2008, 118, 4058-66.
21. A. Watzke, et al., *Angew Chem Int Ed Engl* 2008, 47, 406-9.
22. D. S. Folk, et al., *Angew Chem Int Ed Engl* 2012, 51, 10795-9.
23. H. M. Burke, et al., *Chemical Communications* 2015, 51, 10576-10588.
24. F. K. Harlan, et al., *PLoS One* 2016, 11, e0156312.
25. T. Komatsu, et al., *Journal of the American Chemical Society* 2006, 128, 15946-15947.
26. J. Han, M. S. Han, and C.-H. Tung, *Molecular BioSystems* 2013, 9, 3001-3008.
27. N.-H. Ho, R. Weissleder, and C.-H. Tung, *ChemBioChem* 2007, 8, 560-566.
28. M. Kamiya, et al., *Journal of the American Chemical Society* 2011, 133, 12960-12963.
29. M. Sakabe, et al., *Journal of the American Chemical Society* 2013, 135, 409-414.
30. A. K. Yadav, et al., *Journal of the American Chemical Society* 2015, 137, 1181-1189.
31. M. D. Witte, et al., *Nat Chem Biol* 2010, 6, 907-13.
32. J. D. McCarter, M. J. Adam, and S. G. Withers, *Biochemical Journal* 1992, 286, 721-727.
33. M. N. Namchuk, S. G. Withers, *Biochemistry* 1995, 34, 16194-16202.
34. A. Trapero, A. Llebaria, *Future Medicinal Chemistry* 2014, 6, 975-978.
35. T. M. Gloster, D. J. Vocadlo, *Nature Chemical Biology* 2012, 8, 683-694.
36. S. Patnaik, et al., *Journal of Medicinal Chemistry* 2012, 55, 5734-5748.
37. G. Parenti, *Embo Molecular Medicine* 2009, 1, 268-279.
38. J. Q. Fan, *Trends in Pharmacological Sciences* 2003, 24, 355-360.
39. I. R. Greig, et al., *Journal of the American Chemical Society* 2009, 131, 13415-13422.
40. D. L. Shen, et al., *Journal of Biological Chemistry* 2012, 287, 15395-15408.
41. E. R. Gillies, et al., *Bioconjugate Chemistry* 2004, 15, 1254-1263.
42. B. Liu, et al. *Journal of the American Chemical Society* 2017, 139, 2306-2317.

What is claimed is:
1. A compound of Formula (I) or a salt thereof:

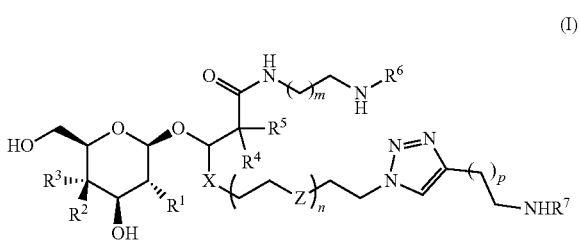

(I)

wherein
X is O or S;
Z is O or $CH_2$;
$R^1$ is OH or $NHC(O)CH_3$;
$R^2$ is OH and $R^3$ is H, or $R^2$ is H and $R^3$ is OH;
$R^4$ is H or $CH_3$;
$R^5$ is H, OH, or halo;
$R^6$ is a fluorophore and $R^7$ is a quencher, or $R^6$ is a quencher and $R^7$ is a fluorophore;
m is an integer from 1 to 5;
n is an integer from 0 to 2; and
p is an integer from 0 to 5.

2. The compound of claim 1 wherein:
X is O;
Z is O;
$R^1$ is OH or $NHC(O)CH_3$;
$R^2$ is OH and $R^3$ is H, or $R^2$ is H and $R^3$ is OH;
$R^4$ is H or $CH_3$;
$R^5$ is H, OH, or halo;
$R^6$ is 5-sulfonaphthalen-1-yl or (2-(6-(dimethylamino)-3-(dimethyliminio)-3H-xanthen-9-yl)benzoate)-5-carbonyl;
$R^7$ is (E)-4-((4-(dimethylamino)phenyl)diazenyl)benzoyl or 4-((4-((E)-(2,5-dimethoxy-4-((E)-(4-nitrophenyl)diazenyl)phenyl)diazenyl)phenyl)(methyl)amino)-butanoyl;
m is an integer from 1 to 5;
n is 1; and
p is 0.

3. The compound of claim 1 wherein the compound is selected from the following group:
5-((2-((2R,3R)-3-(((2S,3R,4R,5S,6R)-3-acetamido-4,5-dihydroxy-6-(hydroxymethyl)tetrahydro-2H-pyran-2-yl)oxy)-2-bromo-3-(2-(2-(4-((4-((E)-(4-(dimethylamino)phenyl)diazenyl)benzamido)methyl)-1H-1,2,3-triazol-1-yl)ethoxy)ethoxy)-2-methylpropanamido)ethyl)amino)naphthalene-1-sulfonic acid;
5-((2-((2R,3R)-3-(((2S,3R,4R,5S,6R)-3-acetamido-4,5-dihydroxy-6-(hydroxymethyl)tetrahydro-2H-pyran-2-yl)oxy)-3-(2-(2-(4-((4-((E)-(4-(dimethylamino)phenyl)diazenyl)benzamido)methyl)-1H-1,2,3-triazol-1-yl)

ethoxy)ethoxy)-2-hydroxy-2-methylpropanamido)
ethyl)amino)naphthalene-1-sulfonic acid
5-((6-((2R,3R)-3-(((2S,3R,4R,5S,6R)-3-acetamido-4,5-dihydroxy-6-(hydroxymethyl)tetrahydro-2H-pyran-2-yl)oxy)-3-(2-(2-(4-((4-((E)-(2,5-dimethoxy-4-((E)-(4-nitrophenyl)diazenyl)phenyl)diazenyl)phenyl)(methyl)amino)butanamido)methyl)-1H-1,2,3-triazol-1-yl)ethoxy)ethoxy)-2-hydroxy-2-methylpropanamido)hexyl)carbamoyl)-2-(6-(dimethylamino)-3-(dimethyliminio)-3H-xanthen-9-yl)benzoate;
5-((2-((2R,3R)-2-bromo-3-(2-(2-(4-((4-((E)-(4-(dimethylamino)phenyl)diazenyl)benzamido)methyl)-1H-1,2,3-triazol-1-yl)ethoxy)ethoxy)-2-methyl-3-(((2S,3R,4S,5R,6R)-3,4,5-trihydroxy-6-(hydroxymethyl)tetrahydro-2H-pyran-2-yl)oxy)propanamido)ethyl)amino)naphthalene-1-sulfonic acid;
5-((2-((2R,3R)-3-(2-(2-(4-((4-((E)-(4-(dimethylamino)phenyl)diazenyl)benzamido)methyl)-1H-1,2,3-triazol-1-yl)ethoxy)ethoxy)-2-hydroxy-2-methyl-3-(((2S,3R,4S,5R,6R)-3,4,5-trihydroxy-6-(hydroxymethyl)tetrahydro-2H-pyran-2-yl)oxy)propanamido)ethyl)amino)naphthalene-1-sulfonic acid;
5-((2-((2R,3R)-3-(2-(2-(4-((4-((E)-(4-(dimethylamino)phenyl)diazenyl)benzamido)methyl)-1H-1,2,3-triazol-1-yl)ethoxy)ethoxy)-2-hydroxy-2-methyl-3-(((2S,3R,4S,5S,6R)-3,4,5-trihydroxy-6-(hydroxymethyl)tetrahydro-2H-pyran-2-yl)oxy)propanamido)ethyl)amino)naphthalene-1-sulfonic acid;
5-((2-(3-(2-(2-(4-((4-((E)-(4-(dimethylamino)phenyl)diazenyl)benzamido)methyl)-1H-1,2,3-triazol-1-yl)ethoxy)ethoxy)-3-(((2S,3R,4S,5S,6R)-3,4,5-trihydroxy-6-(hydroxymethyl)tetrahydro-2H-pyran-2-yl)oxy)propanamido)ethyl)amino)naphthalene-1-sulfonic acid; or
5-((6-(3-(2-(2-(4-((4-((E)-(2,5-dimethoxy-4-((E)-(4-nitrophenyl)diazenyl)phenyl)diazenyl)phenyl)(methyl)amino)butanamido)methyl)-1H-1,2,3-triazol-1-yl)ethoxy)ethoxy)-3-(((2S,3R,4S,5S,6R)-3,4,5-trihydroxy-6-(hydroxymethyl)tetrahydro-2H-pyran-2-yl)oxy)propanamido)hexyl)carbamoyl)-2-(6-(dimethylamino)-3-(dimethyliminio)-3H-xanthen-9-yl)benzoate;
or an acceptable salt of any of the foregoing compounds.

4. The compound of claim 1 wherein the compound is a fluorescence-quenched substrate for an exo-glycosidase.

5. The compound of claim 4 wherein the exo-glycosidase is a mammalian exo-glycosidase.

6. A method for determining exo-glycosidase activity in a cell, the method comprising:
a) providing a test cell and a control cell;
b) contacting the test cell with a compound of Formula (I), or an acceptable salt thereof:

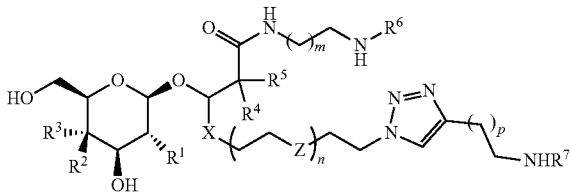

(I)

wherein
X is O or S;
Z is O or CH$_2$;
R$^1$ is OH or NHC(O)CH$_3$;
R$^2$ is OH and R$^3$ is H, or R$^2$ is H and R$^3$ is OH;
R$^4$ is H or CH$_3$;
R$^5$ is H, OH, or halo;
R$^6$ is a fluorophore and R$^7$ is a quencher, or R$^6$ is a quencher and R$^7$ is a fluorophore;
m is an integer from 1 to 5;
n is an integer from 0 to 2; and
p is an integer from 0 to 5; and
c) determining fluorescence intensity in the test cell and the control cell, wherein an increase in fluorescence intensity of the test cell when compared to the control cell is indicative of exo-glycosidase activity.

7. A method for localizing exo-glycosidase activity within a cell, the method comprising:
a) providing a test cell and a control cell;
b) contacting the test cell with a compound of claim 1, or an acceptable salt thereof; and
c) visualizing fluorescence intensity in the test cell and the control cell, wherein an increase in fluorescence intensity in a location in the test cell when compared to the fluorescence intensity in a corresponding location in the control cell is indicative of exo-glycosidase activity.

8. The method of claim 7 wherein the location is the endoplasmic reticulicum, cytosol, nucleus, Golgi apparatus, mitochondria or lysosomal compartment.

9. A method for determining the effect of an exo-glycosidase modulator in a cell, the method comprising:
a) providing a test cell and a control cell;
b) contacting the test cell with an exo-glycosidase modulator;
c) contacting the test cell and the control cell with a compound of claim 1, or an acceptable salt thereof; and
d) determining fluorescence intensity in the test cell and the control cell, wherein a difference in fluorescence intensity of the test cell when compared to the control cell is indicative of exo-glycosidase modulation.

10. The method of claim 9 wherein the exo-glycosidase modulator is an exo-glycosidase inhibitor or an exo-glycosidase activator or an exo-glycosidase chaperone.

11. A method for determining the efficacy of an exo-glycosidase-directed therapy, the method comprising:
a) providing a test cell, wherein the test cell is obtained from a subject treated with an exo-glycosidase-directed therapy, and a control cell, wherein the control cell is obtained from a subject not treated with an exo-glycosidase-directed therapy;
b) contacting the test cell and the control cell with a compound of claim 1, or an acceptable salt thereof; and
c) measuring fluorescence intensity in the test cell and the control cell, wherein a difference in fluorescence intensity of the test cell when compared to the control cell is representative of the efficacy of the exo-glycosidase-directed therapy.

12. The method of claim 6 wherein the cells are fibroblasts or PBMCs.

13. The method claim 6 wherein the cells are derived from a tissue.

14. The method of claim 13 wherein the tissue is a skin punch.

15. A method of screening for an exo-glycosidase activity enhancer, the method comprising:
a) providing a test cell and a control cell;
b) contacting the test cell with a test compound;

c) contacting the test cell and the control cell with a compound of Formula (I), or an acceptable salt thereof claim 1, or an acceptable salt thereof; and d) determining fluorescence intensity for the test cell and the control cell, wherein an increase in fluorescence intensity in the test cell when compared to the control cell indicates that the test compound is an exo-glycosidase activity enhancer.

16. The method of claim 6 wherein:
X is O;
Z is O;
$R^1$ is OH or NHC(O)CH$_3$;
$R^2$ is OH and $R^3$ is H, or $R^2$ is H and $R^3$ is OH;
$R^4$ is H or CH$_3$;
$R^5$ is H, OH, or halo;
$R^6$ is 5-sulfonaphthalen-1-yl or (2-(6-(dimethylamino)-3-(dimethyliminio)-3H-xanthen-9-yl)benzoate)-5-carbonyl;
$R^7$ is (E)-4-((4-(dimethylamino)phenyl)diazenyl)benzoyl or 4-((4-((E)-(2,5-dimethoxy-4-((E)-(4-nitrophenyl)diazenyl)phenyl)diazenyl)phenyl)(methyl)amino)-butanoyl;
m is an integer from 1 to 5;
n is 1; and
p is 0.

17. The compound of claim 2 wherein the compound is a fluorescence-quenched substrate for an exo-glycosidase.

18. The compound of claim 3 wherein the compound is a fluorescence-quenched substrate for an exo-glycosidase.

19. The method of claim 6 wherein the compound is selected from the following group:

5-((2-((2R,3R)-3-(((2S,3R,4R,5S,6R)-3-acetamido-4,5-dihydroxy-6-(hydroxymethyl)tetrahydro-2H-pyran-2-yl)oxy)-2-bromo-3-(2-(2-(4-((4-((E)-(4-(dimethylamino)phenyl)diazenyl)benzamido)methyl)-1H-1,2,3-triazol-1-yl)ethoxy)ethoxy)-2-methylpropanamido)ethyl)amino)naphthalene-1-sulfonic acid;

5-((2-((2R,3R)-3-(((2S,3R,4R,5S,6R)-3-acetamido-4,5-dihydroxy-6-(hydroxymethyl)tetrahydro-2H-pyran-2-yl)oxy)-3-(2-(2-(4-((4-((E)-(4-(dimethylamino)phenyl)diazenyl)benzamido)methyl)-1H-1,2,3-triazol-1-yl)ethoxy)ethoxy)-2-hydroxy-2-methylpropanamido)ethyl)amino)naphthalene-1-sulfonic acid;

5-((6-((2R,3R)-3-(((2S,3R,4R,5S,6R)-3-acetamido-4,5-dihydroxy-6-(hydroxymethyl)tetrahydro-2H-pyran-2-yl)oxy)-3-(2-(2-(4-((4-((E)-(2,5-dimethoxy-4-((E)-(4-nitrophenyl)diazenyl)phenyl)diazenyl)phenyl)(methyl)amino)butanamido)methyl)-1H-1,2,3-triazol-1-yl)ethoxy)ethoxy)-2-hydroxy-2-methylpropanamido)hexyl)carbamoyl)-2-(6-(dimethylamino)-3-(dimethyliminio)-3H-xanthen-9-yl)benzoate;

5-((2-((2R,3R)-2-bromo-3-(2-(2-(4-((4-((E)-(4-(dimethylamino)phenyl)diazenyl)benzamido)methyl)-1H-1,2,3-triazol-1-yl)ethoxy)ethoxy)-2-methyl-3-(((2S,3R,4S,5R,6R)-3,4,5-trihydroxy-6-(hydroxymethyl)tetrahydro-2H-pyran-2-yl)oxy)propanamido)ethyl)amino)naphthalene-1-sulfonic acid;

5-((2-((2R,3R)-3-(2-(2-(4-((4-((E)-(4-(dimethylamino)phenyl)diazenyl)benzamido)methyl)-1H-1,2,3-triazol-1-yl)ethoxy)ethoxy)-2-hydroxy-2-methyl-3-(((2S,3R,4S,5R,6R)-3,4,5-trihydroxy-6-(hydroxymethyl)tetrahydro-2H-pyran-2-yl)oxy)propanamido)ethyl)amino)naphthalene-1-sulfonic acid;

5-((2-((2R,3R)-3-(2-(2-(4-((4-((E)-(4-(dimethylamino)phenyl)diazenyl)benzamido)methyl)-1H-1,2,3-triazol-1-yl)ethoxy)ethoxy)-2-hydroxy-2-methyl-3-(((2S,3R,4S,5S,6R)-3,4,5-trihydroxy-6-(hydroxymethyl)tetrahydro-2H-pyran-2-yl)oxy)propanamido)ethyl)amino)naphthalene-1-sulfonic acid;

5-((2-(3-(2-(2-(4-((4-((E)-(4-(dimethylamino)phenyl)diazenyl)benzamido)methyl)-1H-1,2,3-triazol-1-yl)ethoxy)ethoxy)-3-(((2S,3R,4S,5S,6R)-3,4,5-trihydroxy-6-(hydroxymethyl)tetrahydro-2H-pyran-2-yl)oxy)propanamido)ethyl)amino)naphthalene-1-sulfonic acid; or 5-((6-(3-(2-(2-(4-((4-((E)-(2,5-dimethoxy-4-((E)-(4-nitrophenyl)diazenyl)phenyl)diazenyl)phenyl)(methyl)amino)butanamido)methyl)-1H-1,2,3-triazol-1-yl)ethoxy)ethoxy)-3-(((2S,3R,4S,5S,6R)-3,4,5-trihydroxy-6-(hydroxymethyl)tetrahydro-2H-pyran-2-yl)oxy)propanamido)hexyl)carbamoyl)-2-(6-(dimethylamino)-3-(dimethyliminio)-3H-xanthen-9-yl)benzoate;

or an acceptable salt of any of the foregoing compounds.

* * * * *

UNITED STATES PATENT AND TRADEMARK OFFICE
CERTIFICATE OF CORRECTION

| | |
|---|---|
| PATENT NO. | : 11,396,522 B2 |
| APPLICATION NO. | : 16/622870 |
| DATED | : July 26, 2022 |
| INVENTOR(S) | : Vocadlo et al. |

It is certified that error appears in the above-identified patent and that said Letters Patent is hereby corrected as shown below:

In the Claims

Column 77, Line 2, Claim 15  after "Formula (I)"
delete ", or an acceptable salt thereof" and insert -- of --

Signed and Sealed this
Sixth Day of September, 2022

Katherine Kelly Vidal
*Director of the United States Patent and Trademark Office*